US008740962B2

(12) United States Patent
Finch et al.

(10) Patent No.: US 8,740,962 B2
(45) Date of Patent: Jun. 3, 2014

(54) PROSTHESIS FOR RETRIEVAL AND DEPLOYMENT

(75) Inventors: Matthew J. Finch, Amherst, NH (US); Edward McNamara, Chelmsford, MA (US); Stephen J. Forcucci, Winchester, MA (US); Hiroatsu Sugimoto, Cambridge, MA (US)

(73) Assignee: DC Devices, Inc., Tewksbury, MA (US)

( * ) Notice: Subject to any disclaimer, the term of this patent is extended or adjusted under 35 U.S.C. 154(b) by 159 days.

(21) Appl. No.: 12/954,541

(22) Filed: Nov. 24, 2010

(65) Prior Publication Data

US 2011/0295362 A1 Dec. 1, 2011

Related U.S. Application Data

(63) Continuation-in-part of application No. 12/719,843, filed on Mar. 8, 2010, now Pat. No. 8,157,860, and a continuation-in-part of application No. 12/447,617, filed as application No. PCT/AU2007/001704 on Nov. 7, 2007.

(60) Provisional application No. 61/240,085, filed on Sep. 4, 2009, provisional application No. 61/299,559, filed on Jan. 29, 2010.

(30) Foreign Application Priority Data

Nov. 7, 2006 (AU) ................................ 2006906202

(51) Int. Cl.
*A61F 2/06* (2013.01)
(52) U.S. Cl.
USPC ............................ 623/1.11; 623/1.24; 623/2.1
(58) Field of Classification Search
USPC .......................... 623/1.11, 1.24, 2.1
See application file for complete search history.

(56) References Cited

U.S. PATENT DOCUMENTS 4,018,228 A 4/1977 Goosen
4,705,507 A 11/1987 Boyles
(Continued)

FOREIGN PATENT DOCUMENTS

AU 2007317191 A1 5/2008
CN 102905626 A 1/2013
(Continued)

OTHER PUBLICATIONS

European Application Serial No. 10772411.4, European Search Opinion and Supplementary European Search Report mailed Mar. 16, 2012, 5 pages.

(Continued)

*Primary Examiner* — Thomas J Sweet
*Assistant Examiner* — Matthew Schall
(74) *Attorney, Agent, or Firm* — Shay Glenn LLP

(57) ABSTRACT

The present disclosure relates to devices and methods for implanting a prosthesis into a heart of a mammal, such as a person. The disclosure includes a prosthesis that acts as a pressure vent between the left and right atria of the heart. The disclosure also includes a mounting tool for mounting the prosthesis onto a loading tool, the loading tool useful for loading the prosthesis onto a device for delivering the prosthesis into the patient's heart. Control devices and methods for using these devices are also disclosed. The intracardiac pressure vents disclosed allow sufficient flow from the left atrium to the right atrium to relieve elevated left atrial pressure and resulting patient symptoms. The devices also limit the amount of flow from the right atrium to the left atrium to minimize the potential for thrombi or other embolic material from entering arterial circulation.

20 Claims, 46 Drawing Sheets

(56) References Cited

U.S. PATENT DOCUMENTS

| | | |
|---|---|---|
| 5,108,420 A | 4/1992 | Marks |
| 5,171,233 A | 12/1992 | Amplatz et al. |
| 5,334,217 A | 8/1994 | Das |
| 5,429,144 A | 7/1995 | Wilk |
| 5,578,045 A | 11/1996 | Das |
| 5,693,090 A | 12/1997 | Unsworth et al. |
| 5,702,412 A | 12/1997 | Popov et al. |
| 5,725,552 A | 3/1998 | Kotula et al. |
| 5,824,071 A | 10/1998 | Nelson et al. |
| 5,876,436 A | 3/1999 | Vanney et al. |
| 6,050,936 A | 4/2000 | Schweich, Jr. et al. |
| 6,077,281 A | 6/2000 | Das |
| 6,123,715 A | 9/2000 | Amplatz |
| 6,156,055 A | 12/2000 | Ravenscroft |
| 6,190,353 B1 | 2/2001 | Makower et al. |
| 6,193,734 B1 | 2/2001 | Bolduc et al. |
| 6,258,119 B1 | 7/2001 | Hussein et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,303 B1 | 10/2002 | Amplatz et al. |
| 6,527,746 B1 | 3/2003 | Oslund et al. |
| 6,626,936 B2 | 9/2003 | Stinson |
| 6,641,610 B2 | 11/2003 | Wolf et al. |
| 6,645,143 B2 | 11/2003 | VanTassel et al. |
| 6,666,885 B2 | 12/2003 | Moe |
| 6,712,836 B1 | 3/2004 | Berg et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,936,058 B2 | 8/2005 | Forde et al. |
| 6,979,343 B2 | 12/2005 | Russo et al. |
| 7,001,409 B2 | 2/2006 | Amplatz |
| 7,097,653 B2 | 8/2006 | Freudenthal et al. |
| 7,105,024 B2 | 9/2006 | Richelsoph |
| 7,159,593 B2 | 1/2007 | McCarthy et al. |
| 7,226,466 B2 | 6/2007 | Opolski |
| 7,317,951 B2 | 1/2008 | Schneider et al. |
| 7,338,514 B2 | 3/2008 | Wahr et al. |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,524,330 B2 | 4/2009 | Berreklouw |
| 7,530,995 B2 | 5/2009 | Quijano et al. |
| 7,625,392 B2 | 12/2009 | Coleman et al. |
| 7,658,747 B2 | 2/2010 | Forde et al. |
| 7,699,297 B2 | 4/2010 | Cicenas et al. |
| 7,766,966 B2 | 8/2010 | Richelsoph |
| 7,819,890 B2 | 10/2010 | Russo et al. |
| 7,842,026 B2 | 11/2010 | Cahill et al. |
| 7,871,419 B2 | 1/2011 | Devellian et al. |
| 7,927,370 B2 | 4/2011 | Webler et al. |
| 7,976,564 B2 | 7/2011 | Blaeser et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,252,042 B2 | 8/2012 | McNamara et al. |
| 8,460,372 B2 | 6/2013 | McNamara et al. |
| 2001/0029368 A1 | 10/2001 | Berube |
| 2002/0029061 A1 | 3/2002 | Amplatz et al. |
| 2002/0062135 A1 | 5/2002 | Mazzocchi et al. |
| 2002/0072765 A1 | 6/2002 | Mazzocchi et al. |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0095173 A1 | 7/2002 | Mazzocchi et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2002/0198563 A1 | 12/2002 | Gainor et al. |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0111095 A1 | 6/2004 | Gordon et al. |
| 2004/0133236 A1 | 7/2004 | Chanduszko |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | Mccarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0049692 A1 | 3/2005 | Numamoto et al. |
| 2005/0065548 A1 | 3/2005 | Marino et al. |
| 2005/0065589 A1 | 3/2005 | Schneider et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0148925 A1 | 7/2005 | Rottenberg et al. |
| 2005/0165344 A1 | 7/2005 | Dobak, III |
| 2005/0187616 A1 | 8/2005 | Realyvasquez |
| 2005/0240205 A1 | 10/2005 | Berg et al. |
| 2005/0267523 A1 | 12/2005 | Devellian et al. |
| 2005/0273075 A1 | 12/2005 | Krulevitch et al. |
| 2005/0288722 A1 | 12/2005 | Eigler et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0122646 A1 | 6/2006 | Corcoran et al. |
| 2006/0122647 A1 | 6/2006 | Callaghan et al. |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0276882 A1 | 12/2006 | Case et al. |
| 2007/0016250 A1 | 1/2007 | Blaeser et al. |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0168019 A1 | 7/2007 | Amplatz et al. |
| 2007/0185513 A1 | 8/2007 | Woolfson et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |

(56) References Cited

U.S. PATENT DOCUMENTS

| | | |
|---|---|---|
| 2008/0125861 A1 | 5/2008 | Webler et al. |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249612 A1 | 10/2008 | Osborne et al. |
| 2008/0262592 A1 | 10/2008 | Jordan et al. |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul, Jr. et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | Mcnamara |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | Mcnamara et al. |
| 2012/0130301 A1 | 5/2012 | Mcnamara et al. |
| 2012/0165928 A1 | 6/2012 | Nitzan et al. |
| 2012/0259263 A1 | 10/2012 | Celermajer et al. |
| 2012/0265296 A1 | 10/2012 | Mcnamara et al. |
| 2012/0289882 A1 | 11/2012 | Mcnamara et al. |
| 2012/0290062 A1 | 11/2012 | Mcnamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0267885 A1 | 10/2013 | Celermajer et al. |

FOREIGN PATENT DOCUMENTS

| | | |
|---|---|---|
| CN | 102908213 A | 2/2013 |
| EP | 1470785 A1 | 10/2004 |
| EP | 2528646 A2 | 12/2012 |
| EP | 2537490 A1 | 12/2012 |
| WO | 9527448 A1 | 10/1995 |
| WO | 2008/058940 | 5/2008 |
| WO | 2008055301 A1 | 5/2008 |
| WO | 2010111666 A1 | 9/2010 |
| WO | 2010128501 A1 | 11/2010 |
| WO | 2010129089 A2 | 11/2010 |
| WO | 2011093941 A2 | 8/2011 |
| WO | 2011094521 A2 | 8/2011 |
| WO | 2011093941 A3 | 10/2011 |
| WO | 2011093941 A4 | 12/2011 |
| WO | 2011094521 A3 | 12/2011 |
| WO | 2012071075 A1 | 5/2012 |
| WO | 2012109557 A2 | 8/2012 |
| WO | 2012109557 A3 | 1/2013 |
| WO | 2013096965 A1 | 6/2013 |

OTHER PUBLICATIONS

Ad et al., "A one way valved atrial septal patch: A new surgical technique and its clinical application", The Journal of Thoracic and Cardiovascular Surgery, vol. 111, Apr. 1996, pp. 841-848.

Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Design News, "Low Power Piezo Motion", http://www.designnews.com/document.asp?doc_id=229053&dfpPParams &dfpPParams=ht_13,aid_229053&dfpLayout=article, May 14, 2010, 3 pages.

European Application Serial No. EP12180631.9, European Search Report mailed Nov. 19, 2012, 5 pages.

Merchant et al., "Advances in Arrhythmia and Electrophysiology; Implantable Sensors for Heart Failure", Circ. Arrhythm. Electrophysiol., vol. 3, Dec. 2010, pp. 657-667.

Park et al., "Blade atrial septostomy: collaborative study", Circulation, Journal of the American Heart Association, vol. 66, No. 2, Aug. 1982, pp. 258-266.

International Application Serial No. PCT/AU2007/01704, International Preliminary Report on Patentability mailed Aug. 22, 2008, 5 pages.

International Application Serial No. PCT/AU2007/01704, Written Opinion mailed Jan. 16, 2008, 5 pages.

International Application Serial No. PCT/US10/58110, International Preliminary Report on Patentability mailed Nov. 27, 2012, 11 pages.

International Application Serial No. PCT/US2010/026574, International Preliminary Report on Patentability mailed Nov. 10, 2011, 7 pages.

International Application Serial No. PCT/US2010/58110, International Search Report and Written Opinion mailed Aug. 26, 2011, 14 pages.

International Application Serial No. PCT/US2011/041841, International Search Report and Written Opinion mailed Feb. 9, 2012, 12 pages.

(56) References Cited

OTHER PUBLICATIONS

International Application Serial No. PCT/US2011/22895, International Search Report & Written Opinion mailed Oct. 24, 2011, 11 pages.
International Application Serial No. PCT/US2012/024680, International Search Report and Written Opinion mailed Oct. 23, 2012, 11 pages.
Pedra et al., "Stent Implantation to Create Interatrial Communications in Patients With Complex Congenital Heart Disease", Catheterization and Cardiovascular Interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1066.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Watterson et al., "Very Small Pulmonary Arteries: Central End-to-Side Shunt", Ann. Thorac. Surg., vol. 52, No. 5, Nov. 1991, pp. 1132-1137.
International Search Report, PCT/AU2007/001704, Mailed Jan. 16, 2008, 4 pages.
Nanotechnology in Prosthetic Heart Valves, Steven R. Bailey, MD, approx. date 2005, presentation, 31 pages.
A Philosophical Approach to Mitral Valve Repair, Vincent A. Gaudiani, MD and Audrey L. Fisher, MPH, Apr. 24, 2009, presentation, 28 pages.
Direct Flow Medical—My Valve is Better, Steven F. Bolling, MD, Apr. 23, 2009, presentation, 21 pages.
No! Valve Replacement: Patient Prosthetic Mismatch Rarely Occurs, Joseph S. Coselli, MD, Apr. 25, 2009, presentation, 75 pages.
Transcatheter Aortic Valve Therapy: Summary Thoughts, Martin B. Leon, MD, Jun. 24, 2009, presentation, 19 pages.
The Good, the Bad and the Ugly of Transcatheter AVR, Jeffrey W. Moses, MD, Jul. 10, 2009, presentation, 28 pages.
Valve Implantation, Ziyad M. Hijazi, MD, May 10, 2007, presentation, 36 pages.
Transcatheter Devices for Mitral Valve Repair, Surveying the Landscape, Gregg W. Stone, MD, Jul. 10, 2009, presentation, 48 pages.
Comparative Study of in vitro Flow Characteristics between a Human Aortic Valve and a Designed Aortic Valve and Six Corresponding Types of Prosthetic Heart Valves, B. Stormer et al., Eur. Surg. Res. 8: 117-131 (1976), 15 pages.
The Use of an Artificial Foraminal Valve Prosthesis in the Closure of Interatrial and Interventricular Septal Defects, Ramon Larios et al., Dis. Chest. 1959: 36; 631-41, 12 pages.
Insertion of a Fenestrated Amplatzer Atrial Sestosotomy Device for Severe Pulmonary Hypertension, A.J. O'Loughlin et al., Heart Lung Circ. 2006, 15(4):275-77, 3 pages.
Long-Term Follow up of a Fenestrated Amplatzer Atrial Septal Occluder in Pulmonary Arterial Hypertension, T.F. Althoff, et al., Chest 2008, 133:183-85, 5 pages.
International Search Report, PCTUS2010/026574, Mailed Nov. 19, 2010, 4 pages.
PCT/US12/024680, International Application Serial No. PCT/US12/024680, International Preliminary Report on Patentability and Written Opinion mailed Aug. 22, 2013, DC Devices, Inc, 7 pages.
PCT/US2011/041841, International Application Serial No. PCT/US2011/041841, International Preliminary Report on Patentability and Written Opinion mailed Jun. 6, 2013, DC Devices, Inc. et al, 8 pages.
PCT/US2012/071588, International Application Serial No. PCT/US2012/071588, International Search Report and Written Opinion mailed Apr. 19, 2013, DC Devices, Inc., 19 pages.

PROSTHESIS FOR RETRIEVAL AND DEPLOYMENT

CROSS REFERENCE TO RELATED APPLICATIONS

This application is a continuation-in-part of U.S. patent application Ser. No. 12/719,843, filed on Mar. 8, 2010, now U.S. Pat. No. 8,157,860 entitled DEVICES, SYSTEMS AND METHODS TO TREAT HEART FAILURE, which claims priority to U.S. Provisional Application No. 61/240,085, filed on Sep. 4, 2009. This application also claims priority to U.S. Provisional Application No. 61/299,559, filed on Jan. 29, 2010, entitled SYSTEMS, METHODS, AND DEVICES FOR CATHETER-BASED DELIVERY OF IMPLANTABLE DEVICES. Each application is herein incorporated by reference in its entirety.

FIELD

The present disclosure relates generally to devices and methods for treating heart failure. In particular, the disclosure relates to interatrial pressure vents, shunts and the like, which reduce elevated pressure on one side of the heart thus mitigating the symptoms that result, as well as placement devices, systems, and methods therefore.

BACKGROUND OF THE INVENTION

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. In addition to diastolic heart failure, a number of other medical conditions, including systolic dysfunction of the left ventricle and valve disease, can lead to elevated pressures in the left atrium. Increased left atrial pressure often causes acute or chronic breathlessness amongst other problems. In addition, a variety of heart conditions can lead to "right heart failure", which can result in enlargement of the liver (hepatomegaly), fluid accumulation in the abdomen (ascites) and/or swelling of the lower limbs.

Frequently, patients with diastolic heart failure experience breathlessness due, in part, to elevated pulmonary venous pressure. These patients often feel worse when supine than when sitting or standing, implying that small changes in pulmonary venous pressure have a pronounced effect on symptoms.

In the past, strategies have been described for the relief of high pressure in the right atrium, such as the creation of hole(s) in the native or surgically created septum between the left and right atria. These have been designed for the rare conditions of pulmonary hypertension or cavopulmonary connections for certain complex congenital heart diseases.

Accordingly, there exists a need for devices and methods to treat heart failure particularly diastolic and/or systolic failure of the left ventricle and its consequences.

Furthermore, there also still exists a need for devices to relieve high pressure in the left atrium and which will prevent or minimize the chance of the passage of thrombi, especially from the right atrium to the left atrium, and the resulting risk of systemic emboli.

BRIEF SUMMARY

One embodiment is a device for implantation into an atrial septum of a patient. The device includes a cylindrical core defining a passage through the atrial septum, a flow control element comprising a valve within the passage, a first flange connected to the cylindrical core and adapted to engage a first surface of the atrial septum, wherein said first flange comprises a plurality of struts and apices, wherein each apex further comprises a bore, a plurality of retrieval legs extending from each apex and joined together, and a second flange connected to the cylindrical core and adapted to engage a second surface of the atrial septum.

Another embodiment is a device for implantation into an atrial septum of a patient. The device includes a cylindrical core defining a passage through the atrial septum, a flow control element comprising a valve within the passage, a first flange connected to the cylindrical core and adapted to engage a first surface of the atrial septum, wherein said first flange comprises a plurality of struts joined at apices. The device also includes a plurality of retrieval legs extending from each apex and joined together, a second flange connected to the cylindrical core and adapted to engage a second surface of the atrial septum, and a radiopaque or echogenic marker attached to a bore of at least the first or second flange.

Another embodiment is a device for implantation into an atrial septum of a patient. The device includes a cylindrical core defining a passage through the atrial septum, a flow control element comprising a valve within the passage, a first flange connected to the cylindrical core and adapted to engage a first surface of the atrial septum, wherein said first flange comprises a plurality of struts and apices, and further comprising a plurality of retrieval legs extending from each apex and joined together, and a second flange connected to the cylindrical core and adapted to engage a second surface of the atrial septum, wherein said second flange comprises a plurality of struts and apices, and further comprising a plurality of retrieval legs extending from each apex and joined together.

These and other patient needs are met by providing a venting device, a prosthesis, such as an interatrial pressure vent, which in some embodiments comprises a controlled opening or an extended tubular opening, between the left atrium and right atrium that allows an amount of blood to vent from the left heart to the right heart, thereby reducing left atrial pressure and the symptoms associated with diastolic heart failure.

Several unique intracardiac pressure vents, placement catheters, methods of placement and methods of treating heart failure are presented. The intracardiac pressure vents or prostheses presented allow sufficient flow from the left atrium to the right atrium to relieve elevated left atrial pressure and resulting patient symptoms but also limit the amount of flow from the right atrium to the left atrium to minimize the potential for thrombi or other embolic material from entering the arterial circulation.

In addition, the intracardiac pressure vents or prostheses presented solve the problem of controlling flow in one direction but minimizing flow in another direction with very low changes in pressure across the device.

Also, the intracardiac pressure vents presented solve the problem of reducing calcium deposition, protein deposition and thrombi formation in a low pressure environment.

Furthermore, the intracardiac pressure vents presented solve the problem of damage to the interatrial septum as well as the rest of the left atrium from excessive pressure against the wall which can cause injury to the tissue and possibly adverse reaction by the patient or compromised function to the interatrial pressure vent.

In addition, atrial arrhythmias are frequently seen in patients with heart failure and may, in part, be caused by chronically elevated left atrial pressure. Therefore, relief of elevated left atrial pressure may lead to reduction of atrial fibrillation.

The present disclosure provides prostheses, that is, interatrial pressure vents, along with placement catheters, methods for placing a device in the interatrial septum within the heart of a patient and methods for treatment of the symptoms of heart failure, particularly diastolic heart failure.

In embodiments, the interatrial pressure vent or prosthesis comprises a body assembly and a flow control element; the body assembly comprises a flexible, substantially open mesh adapted for use in a patient. The flow control element attaches to at least one point of the body assembly and the flow control element provides greater resistance to flow in one direction than it does in another direction.

In embodiments, the interatrial pressure vent comprises a body assembly and a flow control element; the body assembly comprises a flexible, substantially open mesh adapted for use in a patient. The flow control element attaches to at least one point of the body assembly and is at least partially open to flow when there is no pressure differential across the flow control element.

In embodiments, the interatrial pressure vent comprises a body assembly and a flow control element; the body assembly comprises a core segment and at least one flange segment; the flange segment is integral with, or attached to at least one point adjacent to, an end of the core segment; the flange segment extends radially outward from the center longitudinal axis of the core segment. The flow control element attaches to at least one point along the core segment and the flow control element provides greater resistance to flow in one direction than in the opposite direction.

In embodiments, the interatrial pressure vent comprises a body assembly and a flow control element; the body assembly comprises a substantially cylindrical core segment and at least one flange segment; the flange segment is integral with, or attached at least to one point adjacent to, an end of the core segment; the flange segment extending radially outward from the center longitudinal axis of the core segment. The flow control element attaches to at least one point along the core segment and the flow control element provides greater resistance to flow in one direction than another direction.

In embodiments, the interatrial pressure vent comprises a body assembly and a flow control element. The body assembly comprises a substantially cylindrical core segment and at least one flange segment integral with, or attached to at least one end of, the core segment; the flange segment extending radially outward from the axis of the core segment. The flow control element attaches to at least one point along the core segment and the flow control element is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and provides greater resistance to flow in one direction than the other direction.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element attaches to at least one point along the flange assembly and is at least partially open to flow when there is no pressure differential across the flow control element.

In embodiments, the interatrial pressure vent comprises a body assembly and a flow control element. The body assembly comprises a substantially cylindrical core segment and at least one flange segment integral with, or attached to at least one end of, the core segment and extending away from the axis of the core segment. The flow control element extends at least partly onto the flange assembly and creates a sealable contact to the atrial septum and provides greater resistance to flow in one direction than the other direction.

In embodiments, the interatrial pressure vent comprises a body assembly and a flow control element. The body assembly comprises a substantially cylindrical core segment and at least one flange segment integral with, or attached to, at least one end of the core segment and extends away from the axis of the core segment. The flow control element attaches to the flange assembly and creates a sealable connection to the atrial septum and is at least partially open to flow when there is no pressure differential across the flow control element.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element provides greater resistance to flow in one direction than it does in another direction.

In embodiments, the interatrial pressure vent comprises a body assembly with a first end and a second end and a flow control element; the body assembly comprises a core segment including at least one flange segment integral with, or attached to, at least one point adjacent to the first end of the core segment and at least one other flange segment integral with, or attached to, at least one point adjacent to the second end of the core segment; the flange segments extending radially outward from the center longitudinal axis of the core segment and the flange segments oriented so they do not oppose each other when deployed. The flow control element attaches to at least one point along the core segment and the flow control element is at least partially open to flow when there is no pressure differential across the flow control element.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments on either side of the core segment being a whole multiple of the number of leaflets.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being a whole multiple of the number of leaflets. The flow control element attaches to at least one point of the body assembly and the flow control element provides greater resistance to flow in one direction than another direction.

In embodiments, the interatrial pressure vent comprises a body assembly with a first end and a second end and a flow control element comprised of at least one leaflet; the body assembly comprises a substantially cylindrical core segment and a number of flange segments integral with, or attached to, at least one point on each side of the body segment and extending radially outward from the center longitudinal axis of the core segment; the number of flange segments being some multiple of the number of leaflets. The flow control element attaches to at least one point of the body assembly and is at least partially open to flow when there is no pressure differential across the flow control element.

In embodiments, an implant system comprises an interatrial pressure vent and placement catheter for treating heart failure. The implant system is comprised of a body assembly and a flow control element. The body assembly is comprised of a substantially cylindrical core segment and at least one flange segment integral with, or attached to, at least one end of the core segment and extending radially away from the core segment. The flow control element is attached to at least one point along the core segment and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube or sheath and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube and a handle component. The inner shaft also contains at least one lumen that extends along at least part of the length of the inner shaft. The outer shaft comprises an elongate hollow tube (or sheath) and a different handle component that slideably interfaces with the first handle component.

In embodiments, an implant system comprises and interatrial pressure vent and placement catheter for treating heart failure. The implant system is comprised of a body assembly and a flow control element. The body assembly is comprised of a substantially cylindrical core segment and at least one flange segment integral with, or attached to, at least one end of the body assembly and extending radially away from the body segment. The flow control element is attached to at least one point along a flange and provides greater resistance to flow in one direction than the other direction. The placement catheter is comprised of an inner shaft and an outer shaft. The inner shaft comprises an elongate tube with at least one flange or circumferential groove formed in the outer diameter and a handle component. The inner shaft also contains at least one lumen that extends along at least part of the length of the inner shaft. The outer shaft comprises an elongate hollow tube (or sheath) and a different handle component that slideably interfaces with the first handle component.

In other embodiments, an embodiment comprises a device for treating a heart condition in a patient comprising a body element having a core segment defining a passage, a first annular flange comprising a plurality of flange segments, and a second annular flange comprising a plurality of flange segments. In embodiments, at least a portion of one of the flange segments is either more or less flexible than the remaining portion of the flange segment or other portions of the body element, including but not limited to the cylindrical core segment.

In other embodiments, the device comprise a third or intermediate annular flange for better adherence to the septal wall.

In other embodiments, the device comprises a flow control element configured to aim the flow of blood in a desired direction. In other embodiments, the device is configured to be more easily retrieved during deployment. Such embodiments can include among other elements a at least one extended flange segment in one of the annular flanges that is able to be retained within a placement catheter when the other portions of the device are deployed.

In embodiments, the method of placing the interatrial pressure vent into position may comprise a sequence of steps to locate and gain access to a vascular channel leading to the heart, placing an introducer catheter via this channel into one of the atriums of the heart, locating the interatrial septum between the left and right atriums, creating an opening in the interatrial septum, advancing a placement catheter containing an interatrial pressure vent into one of the atriums and then through the opening created in the interatrial septum between the right and left atriums, and then controllably deploying the interatrial pressure vent so it is securably connected to the interatrial septum.

Deployment of the interatrial pressure vent preferably occurs in a series of steps comprising first advancing the placement catheter through the septal opening, second deploying a first flange, third retracting the placement catheter to position the first flange against the septal wall, and fourth deploying a second flange on the other side of the septal wall from the first flange.

In embodiments where the device disclosed herein is implanted into the atrial septum, the introducer catheter may be placed through the inferior vena cava via a femoral vein to the right atrium.

Other pathways are available including placing the introducer catheter through the superior vena cava via a jugular vein; through the aorta, via a femoral artery, past the aortic valve and into the left atrium; through the aorta, via a brachial artery, past the aortic valve and into the left atrium; through the superior vena cava via a basilica vein; through the superior vena cava via a cephalic vein; intraoperatively, through an opening created in the right atrium either for this reason or during a procedure performed for some other purpose; intraoperatively through an opening created in the left atrium either for this reason or during a procedure performed for some other reason; or via a guidewire that is positioned through the interatrial septum and located in the pulmonary artery.

Regarding the placement catheter, in some embodiments the placement catheter is designed to function as the introducer catheter and the placement catheter, eliminating the need for a catheter exchange. While in other embodiments, the introducer catheter, the placement catheter, or both are constructed to be exchanged over only part of their length to avoid the necessity of handling a guidewire that is at least twice as long as the catheter. Still in other embodiments, the introducer catheter or the placement catheter, or both has a pre-shaped curve to enable orientation of the placement catheter substantially orthogonal to the septal wall. The catheter may be curved between 30° and 45° away from the catheter axis at a point between 5 and 15 centimeters away from the distal end of the placement catheter.

In embodiments where the inventive device is to be placed in the atrial septum, an opening in the septum can be performed using the introducer catheter in a separate procedure from the interatrial pressure vent placement procedure. Access through the opening can be maintained via a wireguide positioned in the right atrium or the pulmonary artery. The opening can be formed using the placement catheter via a distal tip segment that is part of the placement catheter.

The opening may be predilated using a balloon or other dilating device either as part of the procedure described or as a separate procedure.

In another aspect, the opening is formed and dilated as part of a single, unified procedure with the interatrial pressure vent placement procedure. This may be accomplished by integrating a balloon or other dilating component as part of the placement catheter and dilating the opening as part of placing the interatrial pressure vent. For example, this could be accomplished using a balloon that can be folded to achieve a small loaded profile and will have a suitable pressure capacity and suitable durability to dilate the septum opening and the interatrial pressure vent together.

The opening that is formed in the interatrial septum may be formed by pushing a catheter tip through the septum at the location of septum primum. Because this septum is normally very thin, the distal tip may be pushed directly through without significant force.

In an alternate method, the opening in the interatrial septum can be formed with a cutting tool that is advanced through the introducer catheter or the placement catheter. The tool preferably comprises a blade and a shaft. The blade contains at least two surfaces and one edge. The edge is sharpened and formed at an angle so that the blade slices as it is advanced into and through the septum.

In yet another method, the opening in the interatrial septum can be formed with a cutting tool that is advanced through the introducer catheter or the placement catheter. The tool preferably comprises a blade and a shaft. The blade contains at least two surfaces and two separate edges that are sharpened at an angle so that the blade slices as it is advanced into and through the septum and the septum is cut generally in an x shaped opening.

In yet another method, the opening in the interatrial septum can be formed with a punching tool that is advanced through the introducer catheter or the placement catheter. The punching tool preferably comprises a cutting assembly and a shaft. The cutting assembly preferably comprises a hollow, conical shape with a sharpened edge along the base circumference. The cutting assembly is connected at least to one point on the shaft and is generally oriented so the apex of the cone is pointed away from the shaft.

In one method, the cutting assembly can be operated by advancing the conical assembly through the interatrial septum and then pulling it back to form an opening that is generally circular. In another method, the cutting assembly can be operated by advancing the conical assembly through the interatrial septum and then rotating it as it is pulled pack to create a circular cutting action against the interatrial septum.

In another embodiment, the cutting tool can be formed of at least one cutting member and one shaft. The cutting member is connected at least to one point along the shaft and the other end of the cutting member is adjustably positioned so it can lie alongside the shaft or at some angle away from the shaft. To place the cutting tool, the cutting member is placed alongside the shaft and then advanced through the septum. Then the cutting member would be adjusted to a second position, radially further away from the shaft than the first position, and the shaft would be positioned so the cutting member exerts lateral stress against the septum. The cutting member could be designed to slice the septum in this manner. In another method, the cutting tool could be rotated once the shaft and cutting member were repositioned so the slicing motion would cut a generally circular hole through the septum.

In embodiments, the cutting member is round wire. In another embodiment, the cutting member can be connected to one output of a power supply, capable of supplying a suitable signal to the cutting member, the other output of which is connected to a ground plate placed against the patient's skin. An appropriate electric potential can be placed between the cutting member and ground plate to cause a concentrated current density near the wire to aid in cutting through the septum tissue.

In another embodiment, the cutting member is a section of tubing sliced lengthwise and appropriately formed to create a cutting edge. During placement, the cutting member is controllably positioned to lie against the shaft as the shaft is advanced through the placement catheter and through the opening created in the interatrial septum. Once positioned, the placement catheter is retracted and the shaft is positioned within the septum. Once positioned in this manner, the cutting member can be controllably adjusted to a second position, radially further away from the shaft than the first position, and the shaft positioned so the cutting member exerts lateral stress against the septum.

In yet another method, an opening is created in the interatrial septum which is smaller than the diameter of the outer surface of the body of the interatrial pressure vent according to the present disclosure such that, when the interatrial pressure vent is initially deployed within the interatrial septum, there is some compression from the septum against the body of the interatrial pressure vent.

Referring now to the placement catheter used to position and controllably place the interatrial pressure vent; in one aspect, the placement catheter consists of an inner member and an outer member.

In embodiments, the outer member is comprised of a tubing member and a first handle component, the outer shaft is less than about 16 F in diameter and formed of a material suitably smooth and resilient in order to restrain the stowed interatrial pressure vent and allow smooth stowing and deployment, such as PTFE, FEP, modified ETFE fluoropolymer (such as Tefzel®), PVDF, HDPE or other suitable materials.

In embodiments, the inner member is comprised of at least one tubing member with an inner lumen through at least part of the tubing member, and a second handle component attached to the proximal end, with the second handle component slideably attached to the first handle component.

In embodiments, the handle components are interconnected via an inclined, helical lever to enable advancement of the inner member relative to the outer member by rotating the outer shaft handle while holding the inner shaft handle.

In embodiments, the handle components comprise a locking mechanism that prevents the handle component from moving in relationship to each other beyond a certain predetermined length.

In embodiments, the handle components contain at least two locking mechanisms that prevents the handle component from moving in relationship to each other beyond two different predetermined length.

In embodiments, the inner member contains a stiffening element adjacent to the distal area.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section that has a greater wall thickness than the midsection. The placement device comprises an inner shaft and an outer shaft. The inner shaft comprises an outside diameter and an internal lumen extending at least partly toward the proximal end from the distal end.

The outer shaft contains an outside diameter and an inside diameter. The inner shaft contains a necked portion or circumferential groove along at least part of its length of smaller diameter than at least a portion of the inner member distal to the necked portion; the space formed between the outside of the necked portion and the inside of the outer shaft being sufficient to contain a folded or otherwise compressed interatrial pressure vent of the present disclosure and the space formed between the outside of the non-necked portion and the inside of the outer shaft being insufficient to contain the interatrial pressure vent.

In embodiments, a system for treating heart failure in a patient consists of an interatrial pressure vent and placement device. The interatrial pressure vent comprises a body section and a flow control element. The body section comprises a core section and at least one flange segment. The flange segment comprises a midsection adjacent to the body and an end section located radially further away than the midsection and with a larger dimension in the radial direction than the midsection. The placement device comprises an inner shaft and an outer shaft. The inner shaft contains an outside diameter and an internal lumen extending at least partly toward the proximal end from the distal end. The outer shaft contains an outside diameter and an inside diameter. The inner shaft contains a first necked portion or circumferential groove comprising a length and a diameter; the diameter of the first necked portion of the inner shaft being smaller than at least a portion of the inner member distal to the necked portion and the inner shaft also containing a second necked portion, proximal to the first necked portion and of a length sufficient for containing end section of the flange segment and a diameter smaller than the first necked portion; the space formed between the outside of the first necked portion and the inside of the outer shaft being sufficient to contain the folded or otherwise compressed interatrial pressure vent of the present disclosure except for the end section of the flange segment; the space formed between the outside of the non-necked portion and the inside of the outer shaft being insufficient to contain the interatrial pressure vent and the space formed between the outside of the second necked portion and the inside of the outer shaft being sufficient to contain the end section of the flange segment.

In another aspect, the inner member comprises a first necked portion along at least part of its length of smaller diameter than at least a portion of the inner member distal to the first necked portion and second necked portion, along a second part of its length proximal to the first necked portion and smaller than the first necked portion. The space between the outside of the necked portion and the inside of the outer sheath.

Referring now to the body assembly of the interatrial pressure vent, in one aspect, the body comprises a core segment and at least one flange segment. In embodiments, the body assembly comprises a core segment; a first flange comprising at least one flange segment at one end of the core segment; and a second flange comprising at least one flange segment at the opposite end from the first flange of the core segment.

In embodiments, the body assembly comprises a core segment, comprising a self expanding mesh; a first flange, at one end of the core segment; and a second flange at the opposite end of the core segment from the first flange.

In embodiments, the body assembly is comprised of a core segment, comprising a balloon expandable mesh; a first flange at one end of the core segment; and a second flange at the opposite end of the core segment from the first flange.

In embodiments, the body assembly is comprised of a core segment; a first flange at one end of the core segment; and a second flange at the opposite end of the core segment from the first flange; each flange oriented to extend substantially radially outward relative to the center axis the flange segment.

In embodiments, the body assembly is comprised of a core segment; a first flange at one end of the core segment; and a second flange at the opposite end of the core segment from the first flange; each flange oriented to extend substantially radially outward from the core segment; and at least one flange extending beyond 90° relative to the center axis of the core segment.

In embodiments, the body assembly is comprised of a core segment; a first flange at one end of the core segment; and a second flange at the opposite end from the first flange of the core segment; each flange oriented to extend substantially radially outward from the core segment; the first flange formed with a smaller radius of curvature than the second flange.

In embodiments the interatrial pressure vent comprises a flow control element biased to allow flow from one atrium of a patient to the other atrium of the patient with lower resistance than in the reverse direction.

In embodiments the interatrial pressure vent comprises a flow control element biased that remains at least partially open when there is no pressure differential across the vent.

In embodiments, the interatrial pressure vent comprises an integral filter to prevent embolic particles larger than about 2 mm from passing beyond the filter in the direction of flow.

In other embodiments, the interatrial pressure vent comprises a tubular flow element which extends a distance beyond the core segment so as to prevent embolic particles from entering the left atrium.

In embodiments, the interatrial pressure vent comprises at least one movable flap that responds to pressure changes between the right and left atrium.

In embodiments, the body assembly may be constructed from preformed wire braid. The wire braid may be formed from nitinol with a martensite/austenite transition temperature is below 37° C. so it remains in its superelastic, austenitic phase during use. The transition temperature is below about 25+/−5° C. The wire should have a diameter of at least about 0.0035 (about 2 lbs of breaking strength at 200 ksi tensile). The wire should have a very smooth surface to reduce thrombogenicity or irritation response from the tissue. The surface finish may be 63 μin RA or better. This surface may be obtained either by mechanical polishing, by electropolishing or a combination. In embodiments, the surface may be cleaned with detergents, acids and/or solvents to remove residual oils or contamination and then controllably passivated to insure minimal corrosion.

In embodiments, the body assembly may be formed from grade 1 titanium. In embodiments, the body may be formed of grade 6 titanium. In embodiments, the body may be formed of grade 9 titanium. In embodiments, the body may be formed of 316L stainless steel. In embodiments, the body may be formed of 416L stainless steel. In embodiments, the body may be formed of nitinol or cobalt-chromium-nickel alloy (such as Elgiloy®). In embodiments, the body is formed of platinum iridium. In embodiments, the body may be formed of a cobalt chromium alloy. In embodiments, the body may be formed of MP35N®. In embodiments, the body may be formed of Vitalium™. In embodiments, the body may be formed of Ticonium™. In embodiments, the body may be formed of Stellite®. In embodiments, the body may be formed of tantalum. In embodiments, the body may be formed of platinum. Materials disclosed with reference to the body or any component of the device disclosed herein are not meant to be limiting. The skilled artisan will appreciate that other suitable materials may be used for the body or any other component of the device.

In embodiments, the body assembly is preferably formed from a length of cylindrical tubing that is precut with slots at specific locations and then formed in a series of processes to produce a shape suited for the purpose of containing a flow control element within the interatrial septum.

As an example, a first process might be to stretch the cylinder to expand its internal diameter to a uniform target dimension. This can be done with a balloon or a standard tubing expander consisting of a segmented sleeve and tapered conical inserts that increase the diameter of the sleeve when the cones are advanced toward the center. In order that the shape of the stretched tubing be preserved, the cylinder should be annealed while held into this stretched shape by heating it beyond 300° to 600° for at least about 20 minutes to allow the internal stresses to be relieved. A second process might be to form one flange end shape using a similar process as the first process but using a tool shape specially designed for the first flange shape. A third process might be to form the second flange end shape using a similar process as the first process but using a tool specially designed for the third flange shape. These shapes must be annealed using a similar process as the first shape, either in separate steps or altogether.

In embodiments, the internal diameter of the finished interatrial pressure vent is larger than about 5 mm to enable adequate venting of the left atrium and minimize damage to blood components from excessive shear stress, but enabling the interatrial pressure vent to stow in a placement catheter of smaller than about 14 F.

In embodiments, the flow control element opening is at least about 50 sq. mm. In embodiments, the flow control element opening is 50 sq. mm.+−10 sq. mm. In another embodiment, the cylindrical section is formed with an inside diameter of between 3 and 15 mm.

The internal diameter of the body segment is preferably a constant dimension along the center, longitudinal axis of the interatrial pressure vent and is long enough to isolate the flow control element from deflection or damage as a result of contact with other structural elements of the heart.

In embodiments, the body segment is formed into a substantially toroidal shape, the inner diameter tapering down and then up again from one side of the implant to the other. In embodiments, the length of the body section may be about 4 mm. In embodiments, the length of the body section may be between about 3 mm and about 40 mm.

In yet other embodiments, the flange segment may comprise at least a single loop which is oriented to the cylindrical shape by at least about 90° relative to the central axis of the cylinder and projected outward to a distance away from the center axis of greater than the opening in the atrial septum but at least about 3 mm further than the diameter of the inner cylinder.

In embodiments, the flange segment is formed of multiple struts that extend radially outward, with respect to the center aspect of the cylinder. In embodiments, the flange struts each comprise a substantially triangular shape that is wider adjacent to the body section than at the outer edge of the strut. In embodiments, the flange struts comprise a substantially triangular shape that is wider adjacent to the body section than at the outer edge of the strut and contains an integral hole at the outer edge for containing a radiopaque marker.

In embodiments, the flange struts comprise a substantially triangular shape that is wider adjacent to the body section than at the outer edge of the strut and whose outer edge is rounded to reduce trauma against the tissue it contacts. In embodiments, the flange struts are formed from a single beam of material that project outward from the center longitudinal axis of the body section. In embodiments, the flange segment is formed of spiral shaped flange struts that are coplanar and substantially orthogonal to the central axis of the cylinder.

In embodiments, the flange segment is formed of at least one looping member that attaches to at least one portion of the body section. In embodiments, the flange is preferably formed to automatically recover substantially to its preformed shape following partial deployment of the interatrial pressure vent from the placement catheter. In this manner, the interatrial pressure vent will resist being pulled back through the septal opening.

In embodiments, the flow control element device may be a tissue valve, a synthetic valve or a combination. The flow control element can be formed from animal or human tissue, such as bovine pericardial tissue. The procedures for obtaining these tissues and preparing them for use as implanted valve components are well known to those skilled in the art. The flow control element could be a trileaflet valve, or also a bileaflet valve, or also a simple flap valve. The flow control element could also be a ball and socket valve, a duckbill valve, a butterfly valve, or any other valve component known to those skilled in the art.

In embodiments, the flow control element can be biased by adding a separate component that is attached to at least one point along the body or flange segment and contacts against at least one point of the flow control element surface at least at some point during its duty cycle. The component can be preformed to controllably affect the flow control element behavior. For example, in one embodiment, the flange segment can be a looped wire formed from nitinol and connected to the body section and cantilevered against the surface of the flow control element facing the left atrium and formed so that the surface of the flow control element is biased to be slightly open when the pressure is equal in the left atrium and right atrium. Biasing can also be accomplished by varying the stiffness of the material of the valve or components thereof.

In embodiments, a flange segment could be formed out of a helical winding of nitinol, with a core wire to connect one end of the flange segment to the other end. In embodiments, the flow control element can be preshaped to resist moving against pressure in one direction. In embodiments, the flow control element could be biased to remain open at a predetermined pressure, or at a neutral pressure In embodiments, the interatrial pressure vent consists of a body section and a flow control element; the body section comprising a cylindrical core segment and two flanged end sections; the flow control element being sealably secured to at least three points along the body section; the flanged end sections each comprising at least one flange segment that extends radially outward from the body section; the flow control element comprising at least one movable element that allows fluid passage in one direction with lower resistance than another direction. In embodiments, the body section is elliptical in shape, or cylindriod and designed to offset asymmetric stress created by a linear septal opening.

In embodiments, the formed metal flange segments consist of at least two flange segments, with at least one on each side of the septum. In embodiments, the flange segments are positioned so they do not pinch the septum between them, thereby reducing possible pressure necrosis. In embodiments, the flange segments are shaped so the wall thickness perpendicular to the septum is less than the wall thickness parallel to the septum, thereby increasing flexibility without decreasing strength.

In embodiments, the flange segments are formed so the radius of curvature at the end is greater than about 0.03 inches. In embodiments, there is a radiopaque marker, preferably tantalum or platinum alloy, formed around, or integral with, the flange segment end to increase radiopacity and increase the area of contact between the flange segment and septum. In embodiments, the flange on the left atrium side of the septum is bent at a shorter radius of curvature than the right atrium side.

In embodiments, the flange on one side of the interatrial septum is formed to return to greater than a 90° angle relative to the axis of the center cylinder. In embodiments, holes are preformed at a location along the cylindrical section for suture sites for securing the valving device.

The above summary of the disclosure is not meant to be exhaustive. Other variations and embodiments will become apparent from the description and/or accompanying figures disclosed herein and below. The embodiments described above employ elements of each other and are meant to be combined with each other. For example, embodiments of flow control element may be used with differing configurations of the body element, flange, or segment thereof. While certain combinations are disclosed, the invention is not so limited Other embodiments and advantages of the invention will become more apparent from the following detailed description when taken in conjunction with the accompanying drawings.

BRIEF DESCRIPTION OF THE DRAWINGS

The present disclosure will become more fully apparent from the following description and appended claims, taken in conjunction with the accompanying figures. Understanding that these figures merely depict exemplary embodiments, they are, therefore, not to be considered limiting. It will be readily appreciated that the components of the present disclosure, as generally described and illustrated in the figures herein, could be arranged and designed in a wide variety of different configurations. Nonetheless, embodiments will be described and explained with additional specificity and detail through the use of the accompanying figures in which:

DETAILED DESCRIPTION OF THE PRESENTLY PREFERRED EMBODIMENTS

Figure 1:
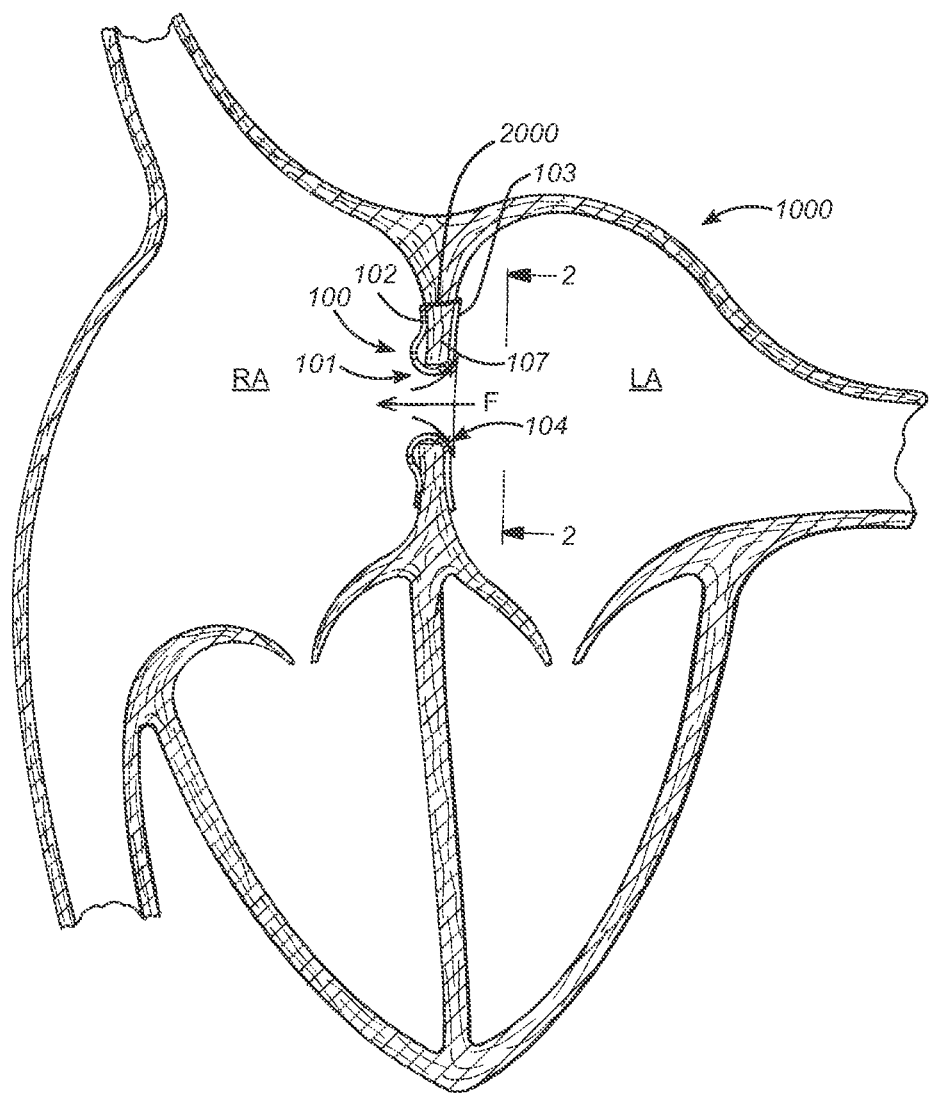
FIG. 1 is a schematic cross-sectional view of a patient's heart with an interatrial pressure vent in situ.

Certain specific details are set forth in the following description and Figures to provide an understanding of various embodiments. Those of ordinary skill in the relevant art will understand that they can practice other embodiments without one or more of the details described below. Finally, while various processes are described with reference to steps and sequences in the following disclosure the steps and sequences of steps should not be taken as required to practice all embodiments of the present disclosure.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring treatment for symptoms of heart failure.

As used herein, the term "pressure differential" means the difference in pressure between two points or selected spaces; for example between one side of a flow control element and another side of the flow control element.

As used herein, the term "embolic particle" means any solid, semi-solid, or undissolved material, that can be carried by the blood and cause disruption to blood flow when impacted in small blood vessels, including thrombi.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at some angle greater than 0 relative to the center longitudinal axis of the cylinder.

As used herein, the term "axial thickness" means the thickness along an axis parallel to the center longitudinal axis of a shape or component.

As used herein, the term "axial direction" means direction parallel to the center longitudinal axis of a shape or component.

As used herein, a "sealable connection" is an area where components and/or objects meet wherein the connection defines provides for an insubstantial leakage of fluid or blood through the subject area.

As used herein, the term "lumen" means a canal, duct, generally tubular space or cavity in the body of a subject, including veins, arteries, blood vessels, capillaries, intestines, and the like.

As used herein, the term "sealably secured" or "sealably connected" means stably interfaced in a manner that is substantially resistant to movement and provides resistance to the flow of fluid through or around the interface.

As used herein, the term "whole multiple" means the product contains no decimal.

The present disclosure provides structures that enable several unique intracardiac and intraluminal valve devices, loaders, controls and placement devices and catheters therefor. In some embodiments directed toward the intra-cardiac setting, these valve devices are intended to allow sufficient flow from the left atrium to the right atrium to relieve elevated left atrial pressure and resulting patient symptoms but also prevent the amount of flow from the right atrium to the left atrium to minimize the potential for thrombi or other embolic material from entering the arterial circulation.

However, it should be appreciated that embodiments are applicable for use in other parts of the anatomy or for other indications. For instance, a device such as that described in this disclosure could be placed between the coronary sinus and the left atrium for the same indication. Also, a pressure vent such as is described in this disclosure could be placed between the azygous vein and the pulmonary vein for the same indication.

Referring now to FIG. 1, one embodiment is used as an interatrial pressure vent. FIG. 1 depicts the heart of a human subject. "LA" refers to the left atrium, and "RA" refers to the right atrium. The interatrial septum is depicted as 107. Interatrial pressure vent 100 includes a body element 101 and flow control element 104, embodiments of which will be described in further detail below. The body element 101 comprises flanges 102 and 103. In this and other embodiments described herein, flanges 102 and 103 may be annular flanges, which define a gap 2000 into which the septum 107 fits. In embodiments, after insertion, the interatrial pressure vent is securely situated in an opening created in the interatrial septum. Arrow F in FIG. 1 shows the direction of flow. It can be thus seen that a build up of pressure in the LA can be vented, by way of the inventive device, to the RA.

Figure 2:
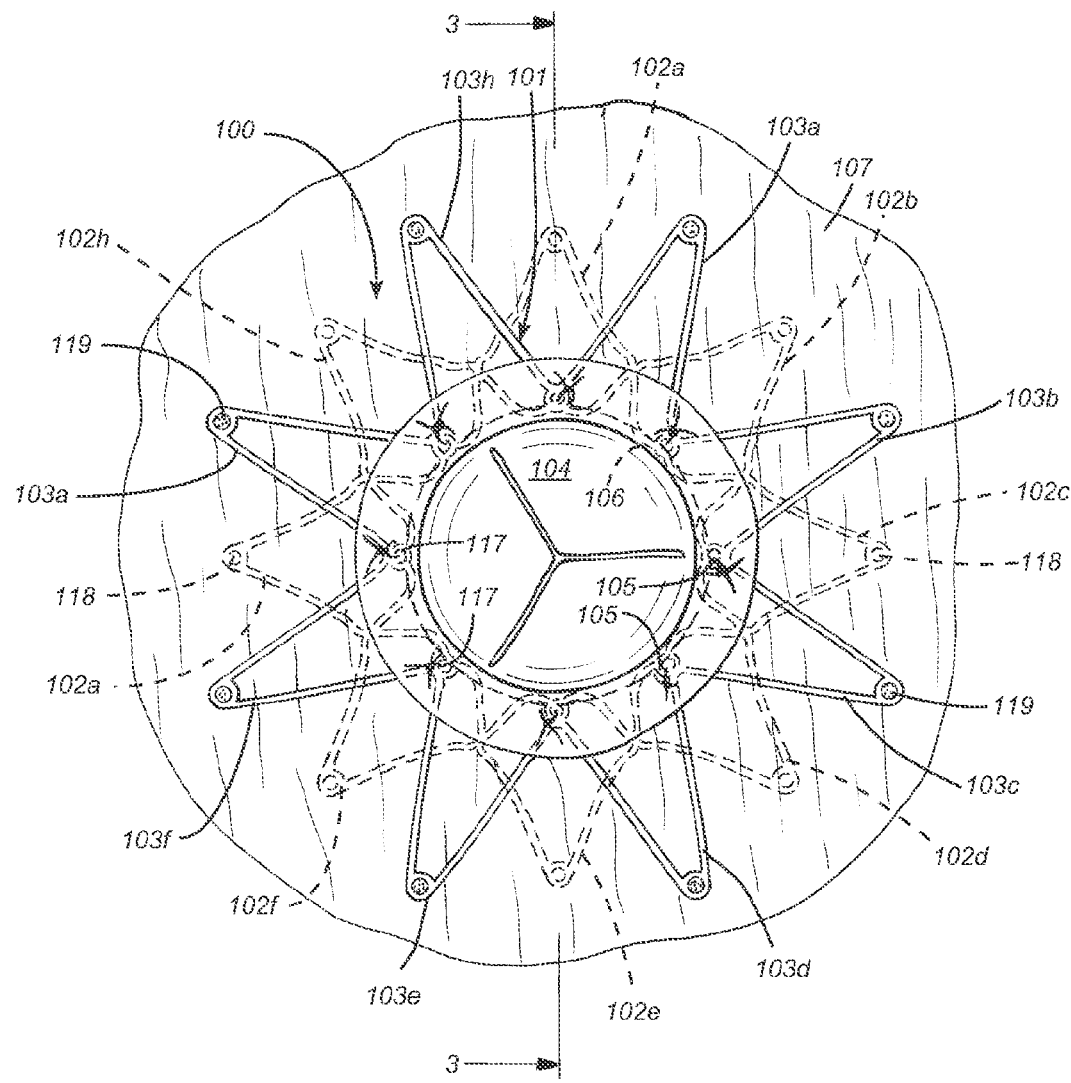
FIG. 2 is an end view of the interatrial pressure vent of FIG. 1 in situ as seen along line 2-2 of FIG. 1.

Referring now to FIG. 2, an embodiment of the interatrial pressure vent is illustrated. Interatrial pressure vent 100 includes body element 101 comprising a substantially open mesh and including a substantially cylindrical core segment (shown end on) 106 and substantially annular flanges 102 and 103. Flanges 102 and 103 may be comprised of any number of flange segments (or "flange elements" or "flange members") 102a-102h and 103a-103h, that are attached adjacent to the end of the core segment and extend radially outward from longitudinal axis of the core segment and flow control element 104. "Flange segments" may also be referred to as "legs" herein. The flanges 102 and 103 (and thus the segments which comprise them 102a-h and 103a-h) in this and all embodiments disclosed herein, may also be integral with the core segment. That is, they need not be necessarily "attached" thereto but may be fabricated from the same material that defines the core segment (including in the manners described above and herein) and thus may be contiguous therewith. The flow control element may be attached to the body element, for example at locations 105. The flange segments in this and any embodiment of any annular flange may be formed of two individual strut elements or also can be formed of a single element. The flange segments may be generally rectangular in cross section, circular in cross section, oval in cross section or some other geometric shape.

Figure 2A:
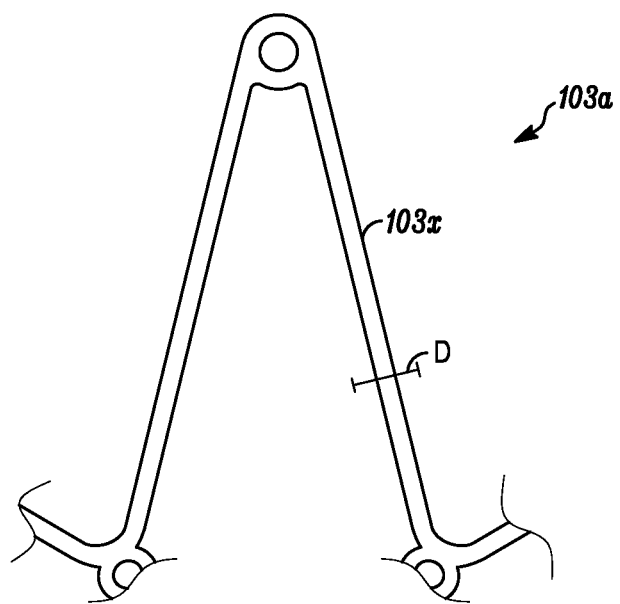
FIG. 2A is an end-on close up view of a flange segment of an embodiment.
Figure 2B:
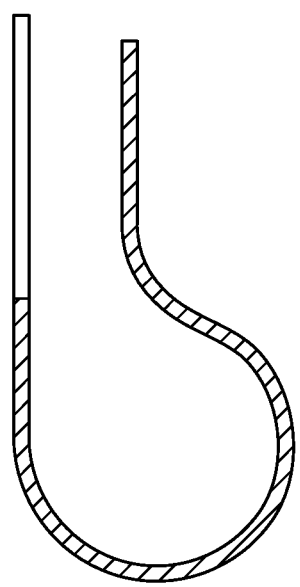
FIG. 2B is an enlarged side cross-sectional view of an embodiment to illustrate variations in flexibility in a flange.

In embodiments, the flange segments are designed to be more flexible than the core segment. In such embodiments, the increased flexibility may be achieved in several ways. In embodiments, a dimension of the surface of the strut elements that make up the flange segments is altered relative to the corresponding dimension of the struts (or elements, or members) that make up the core segments. FIG. 2A illustrates such embodiments. FIG. 2A shows an example flange segment 103a viewed end on. As shown, the end-facing dimension of strut element of 103x has a width D. By decreasing the width D in relation to the width of the outward-facing dimension of the struts that comprise the core segment, an increased flexibility of the flanges in relation to the core segment or other flange members (or portions thereof) can be achieved. FIG. 2B shows an enlarged fragmentary cross-section of an embodiment of the device substantially shown in FIG. 6. The view is taken along line 7-7 of FIG. 6. In this figure, the cross hatched area shows the area of increased flexibility. It can be seen that one area of the flange segment is thus more flexible than another area. In embodiments where the strut elements are circular, then in a similar fashion, the diameter of the strut element could be made to have a diameters less than the diameter of the strut (or similar elements) comprising the mesh-like configuration of the core segment.

In embodiments where the flange element is made from a different section of material and is attached to the core segment, the segment material could be chosen to have a greater flexibility than the core segment (or remaining portion of the flange segment or flange itself as the case may be). The choice of materials based on their flexibility will be apparent to those skilled in the art. In the ways described above, the flange segments can achieve greater flexibility than the core segment (or the remaining portion of the flange segment or the flange itself as the case may be) thereby reducing probability of damage to the tissue of the septum while allowing the core segment to maintain a strong outward force against the septal opening and thus decrease the probability that the device could become dislodged.

In embodiments having an open-mesh configuration for the body element 101, the body element can be formed from a number of materials suitable for use in a patient, such as titanium, nitinol, stainless steel, Elgiloy®, MP35N®, Vitalium, Mobilium, Ticonium, Platinore, Stellite®, tantalum, platinum, or other resilient material. Alternatively, in such embodiments, the body element 101 can be formed from a polymer such as PTFE, UHMWPE, HDPE, polypropylene, polysulfone, or other biocompatible plastic. The surface finish of the body element may be smooth with no edges or sharp discontinuities. In other embodiments, the surface finish is textured to induce tissue response and tissue in growth for improved stabilization. In embodiments, the open mesh of body element 101 can be fabricated from a resorbable polymer such as polylactic acid, polyglycolic acid, polycaprolactone, a combination of two or more of these or a variety of other resorbable polymers that are well known to those skilled in the art.

In embodiments, the structure of the body element may be uniform and monolithic.

In other embodiments, the body element (mesh or monolithic) comprises porous materials to encourage tissue ingrowth or to act as a reservoir for containing one or more compounds that will be released over time after implant to address numerous issues associated with the product performance. These compounds can be used to diminish calcification, protein deposition, thrombus formation, or a combination of some or all of these conditions. The compound can also be used to stimulate an irritation response to induce tissue ingrowth. In embodiments, the compound can be an anti-inflammatory agent to discourage tissue proliferation adjacent to the device. Numerous agents are available for all of such uses and are familiar to those who are skilled in the art.

In embodiments, the material that comprises the body may be multilayered comprising a coating of resorbable polymer or semipermeable polymer that may comprise various compounds that may be released, and in some embodiments in a controlled manner over time, after implant to address numerous issues associated with product performance.

The mesh can be formed from wire that is pre-bent into the desired shape and then bonded together to connect the component elements either by welding them or adhesively bonding them. They could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

In other embodiments, the mesh can be formed from a hollow tube that has been slotted using, for example, a machining laser or water drill or other method and then expanded to form the open structure. If a sufficiently elastic and resilient material, such as nitinol, is used, the structure can be preformed into the finished shape and then elastically deformed and stowed during delivery so the shape will be elastically recovered after deployment. The surface of the finished assembly must be carefully prepared to insure is passivated and free of surface imperfections that could be a nidus for thrombus formation.

In embodiments, the flow control element 104 is a tissue valve such as a tricuspid valve, a bicuspid valve or a single flap valve formed from pericardial tissue from a bovine, porcine, ovine or other animal. Any number of cusps may be used. The flow control element is formed using a number of processing steps and auxiliary materials such as are well known in the art.

The flow control element 104 can also be a ball valve, a duckbill valve, a leaflet valve, a flap valve, a disc in cage type valve, a ball in cage type valve or other type of valve formed from a polymer or polymers or a combination of polymers, ceramics and metals such as Dacron (polyester), PTFE (such as Teflon®), polyurethane, PET or other suitable polymer; titanium, stainless steel, nitinol, MP35N®, cobalt-chromium-nickel alloy (such as Elgiloy®), or other suitable metal; zirconia, silicone nitride, or other suitable ceramic. Valves or portions thereof may comprise different stiffness/flexibly properties with respect to other valves or portions thereof in the flow control element.

The flow control element 104 preferably extends to a point along the flange assembly 103 to enable creation of a sealable connection to the septum wall after placement. This is more particularly shown in FIG. 3 where it can be seen that in embodiments, the flow control element extends beyond the length of the core segment and is folded and attached to the core segment so as to create a lip that extends in a direction center of the opening in the vent. When the device is abutted against the septal wall, this lip forms said sealable connection and thus can reduce the likelihood that blood can flow through the septal opening via pathways between the outer surface (septal-facing surface) of the interatrial pressure venting device and the septal opening. The flow control element 104 is attached to the body element 101. This can be accomplished by using a suture material, such as silk, nylon, polypropylene, polyester, polybutylester or other materials such as are well known to those skilled in the art. In embodiments, flow control element 104 can be attached to body element 101 using adhesive bonding agents such as cyanoacrylate, polymethylmethacrylate, or other materials such as are well known to those skilled in the art. In other embodiments, flow control element 104 can be attached to body element 101 via staples, rivets, rings, clamps or other similar methods as are well known to those skilled in the art.

As mentioned above, flow control element can be made of material selected for its flexibility/stiffness. In embodiments where a loose valve is desired that resonates more closely with the cycle of the heart, a however stiffness material may be chosen. In embodiments where it is desired to open the valve when the pressure differential reaches a selected value, the material of the flow control element can be selected and/or processed in a manner to open at the desired differential. The leaflets or sections of the flow control element itself may also comprise areas of variable stiffness, and or may be more flexible or less flexible than other leaflets or components of the flow control element.

Figure 3:
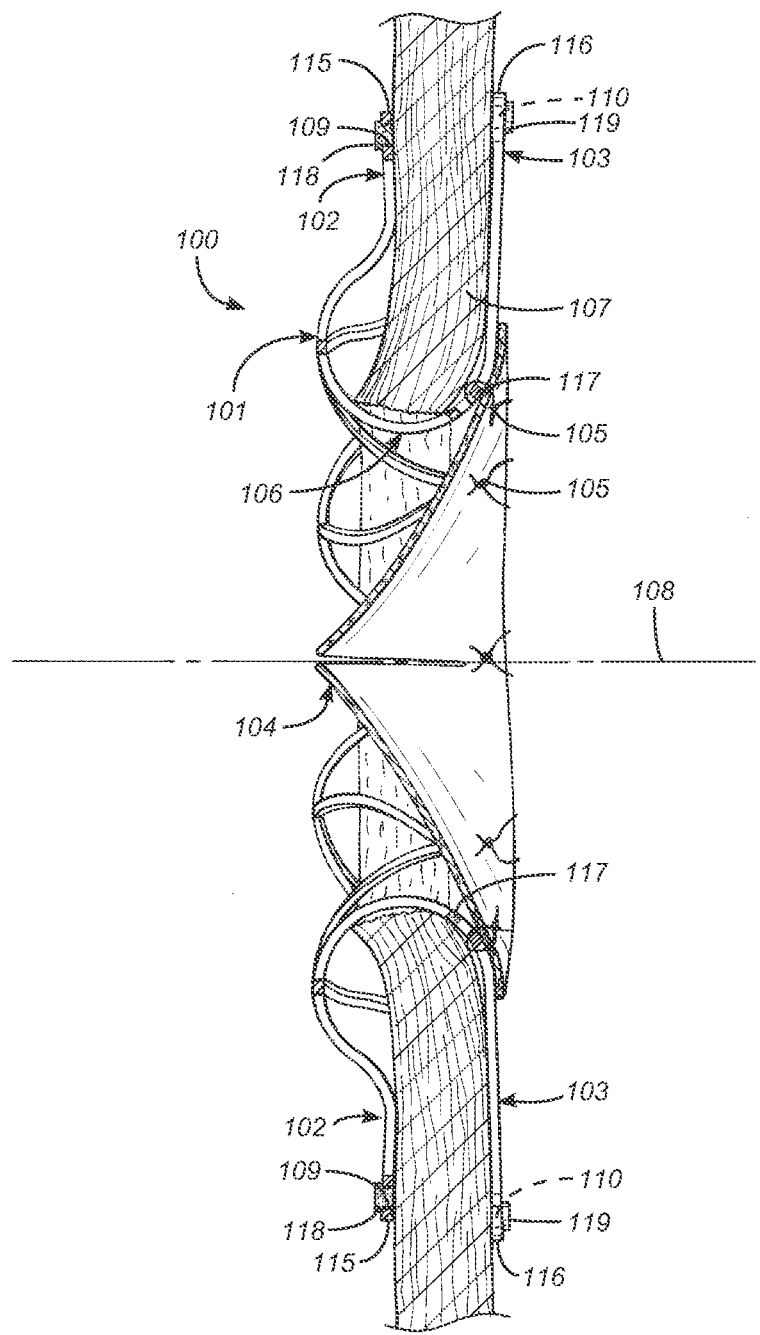
FIG. 3 is a cross-sectional side view taken along line 3-3 of FIG. 2.

FIG. 3 shows the device implanted in the atrial septum of the heart of a patient. As can be seen from the figure, the core segment 106 can be formed contiguously with flanges 102 and 103 and thus flange segments 102a-102h and 103a-103h respectively. In the embodiment shown, flow control element 104 is contained within the core segment 106 so it does not extend beyond the face of the body element 101, thereby insulating it from contact from other body structures or peripheral tissue in embodiments, the core segment 106 can be extended to protrude beyond the interatrial septum 107 and the flange assembly 102 and/or 103 on at least one side of the interatrial septum 107 and can be formed with a shape that extends to create a lip in the manner described above. In embodiments, the ends of the flange assemblies 102, 103 are formed to lie at a parallel angle to and against the septal wall along at least a part of its length to increase the area of contact and thereby decrease the stress concentration against the septal wall.

Figure 4:
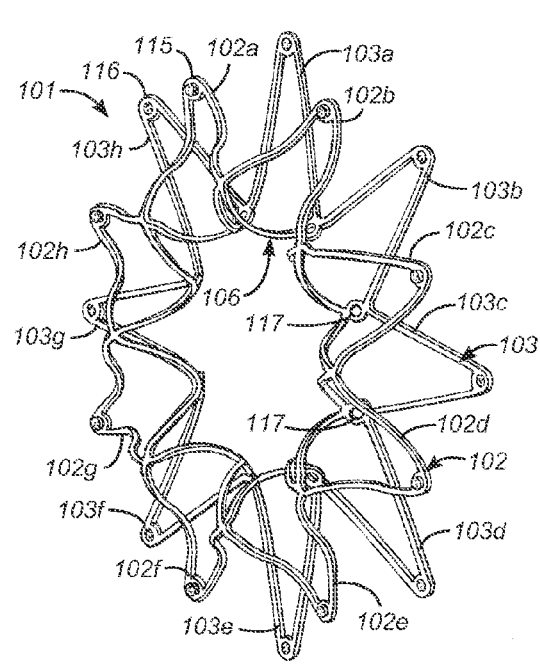
FIG. 4 is perspective view of the body assembly of the interatrial pressure vent by itself.

Referring now to FIG. 4, an embodiment of the body element is shown. This perspective view of the body element 101 shows how, in embodiments, the ends of flange segments 102a-102h, 103a-103h are rounded at their distal ends 115 and 116 to reduce stress concentrations against the interatrial septum after placement. This rounded shape can easily be formed as part of the integral shape of the flange segment. In other embodiments, the thickness of the segment in this area may be decreased to decrease the stress further against the interatrial septum, which is similar to embodiments described above. Also similar to embodiments described above, if the segment is round, the diameter can be decreased in order to increase flexibility. Also, as described above a different material of higher flexibility could be used for the end portions of the segments.

While rounded shapes at the ends of the flange segments reduce stress on the septum, other variations on this theme are contemplated. FIGS. 7A through 7C illustrate embodiments where the shape of the end portions of the flange segments has configurations to achieve less stress against the septal wall—among other goals. FIG. 7A is a side elevational view of embodiment of the pressure venting device in its stowed configuration. Core segment 106 of body element 101 is shown and, in this embodiment, is integral with flanges 103 and 102. The individual flange segments are not labeled; however, it is easily seen that flange 103 comprises segments substantial similar to those described above. There is no eyelet or opening at the end of the segment in the embodiment shown. Flange 102 shows an embodiment where the flange segment is not comprised of a triangular or multi-strut arrangement as described above but rather a single-member segment. Any flange may be constructed with single-member segment. An example single member is referred to as 103s. In this example, at the end of each single-member flange segment (102s) for example, there is an eyelet. FIG. 7B shows an embodiment similar to that shown in FIG. 7A where the end of the segments 102s are not eyelets but rather pads. FIG. 7C shows another embodiment where the ends of the segments 102 are paddle shaped. Other smooth-edged shapes could be used, and it should be understood that such shapes and configurations apply to all manner of flange segment ends, not only single-member segments. This would include the ends of flange segments shown and described herein, for example with reference to FIGS. 2 through 7.

FIGS. 7A-C also show embodiments having at least one flange segment being longer than the other flange segments. Again, while represented as single-member flange segments they need not be and as such a configuration with at least one longer segment may apply to any flange-segment configuration disclosed herein. The benefits and purpose of having at least one longer flange segment will be described more fully below.

In embodiments, the outer ends of the flange segments 102a-102h, 103a-103h are formed with integral marker holes or slots 109 and 110 (shown in FIGS. 3 and 7 for example) in which markers 118 and 119 can be positioned so the device may more easily be visualized using radiographic imaging equipment such as with x-ray, magnetic resonance, ultrasound or other imaging techniques. Markers as disclosed herein may be applied to the ends of any segments, not just those with holes or eyelets therein. A radiopaque marker 118 and 119 can be swaged, riveted, or otherwise placed and secured in the hole and thereby dimensioned to be flush with the end of the segment. Markers may also be simply attached or to end of a segment not having a hole. In all embodiments having markers, flange ends 115 and 116 are more visible when imaged. In other embodiments, the markers 118 and 119 can be bonded with an adhesive agent such as cyanoacrylate or epoxy or a variety of other materials that are available and suitable for implant as are well known. The markers may be proud (as shown for example in FIG. 7) or flush with the end of the flange segment. The radiopaque markers 118 and 119 may be formed of tantalum, tungsten, platinum iridium, gold, alloys of these materials or other materials that are known to those skilled in the art. Also markers 118 and 119 comprising cobalt, fluorine or numerous other paramagnetic materials or other echogenic materials that are known to those skilled in the arts can be incorporated together with the radiopaque materials, or in alternating locations of the flange segments to enable both x-ray and echographic imaging of the interatrial pressure vent. Alternatively, the ends of the flange elements 102a-102h and 103a-103h can be wrapped with a foil made of the same marker materials. In embodiments, the radiopaque material can be laminated to the flange segments and bonded through a welding process or using an adhesive such as cyanoacrylate or numerous other adhesives known to those skilled in the art.

Suture rings 117 can be formed in the body element to locate and fix the attachment site along the body element to the flow control element. The suture rings can be circular holes formed into the structure or they could also be some other shape such as rectangular or triangular and also can be formed as a secondary step, for example by standard machining techniques, using a secondary laser machining step, or with electro-chemical etching. Preferably the connection between a segment and any other segment of the body element are formed with as large a radius as possible to increase resistance to fatigue failure. Also, preferably, all edges of the formed device are rounded to improve biocompatibility and hemocompatibility.

The pattern of suture rings as well as which of the rings are selected during suturing may affect the properties of the flow control element. For example, in embodiments where it is desired to have the flow element loose and flappable, less suture rings may be utilized and, in such embodiments, RA-side end of the flow control element may contain relatively less sutures than the LA side. In other embodiments, it may be desirable to keep the flow control element affixed to the core segment for a increased length of the segment thereby reducing the amount of flow control element material that affecting flow. Still in other embodiments the top or bottom portion the flow element at the RA side may be sutured in such a way so as to allow the top or bottom portion of the flow control element to affect flow more than the other portion respectively. Embodiments discussed below where the flow is "aimed" may utilize suturing patterns effective to enable the desired flow control element configuration.

Retuning to the flange segments, in an embodiment, the interatrial pressure vent 100 is comprised of an equal number of flange segments on each side of the interatrial septum. In embodiments, there are eight flange segments on each side of the core segment. In another aspect there are an equal number of suture rings and flange segments on one side of the interatrial pressure vent. In other embodiments, there are seven flange segments on each side of the core segment. In other embodiments, there are six flange segments on each side of the core segment. In other embodiments, there are five flange segments on each side of the core segment. In other embodiments there are four flange segments on each side of the core segment. In other embodiments there are three flanges on each side of the core segment. In other embodiments there are two flanges on each side of the core segment. In other embodiments, there is one flange on each side of the core segment. Still in other embodiments there are more flange segments as compared to flange segments. And in other embodiments, there are more flange segments as compared to flange segments. As can be seen there are a number of variations for the number of flange segments and the skilled artisan will appreciate that any number could be used while not deviating from the scope and spirit of this disclosure.

Figure 5:
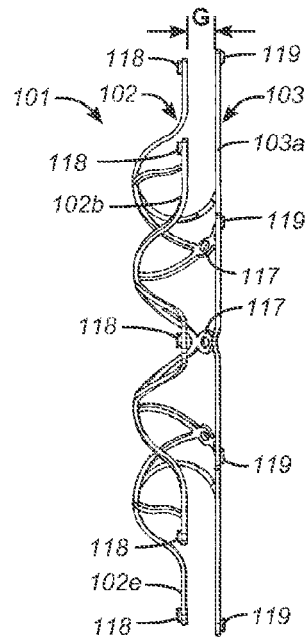
FIG. 5 is a right side view of the body assembly of FIG. 4.

Referring now to FIG. 5, the body element of an embodiment is displayed in side view. The flange segments can be formed to produce a gap G (also referred to as an annular gap) between the ends of flange segments on one side of the body and flange segments on the other side of the body, when the device is in its "native" or un-deployed state. When the device is deployed, it flexes to accommodate the tissue and as such the gap may expand when tissue is positioned therein. In embodiments, this gap is slightly smaller than the thickness of the interatrial septum. In other embodiments, the gap can be larger than the thickness of the interatrial septum. In other embodiments the gap can be zero. In another aspect the gap can be negative: in this case the flange segments on each side of the body can be formed to cross each other in order to exert more pressure between the deployed flange segments and the interatrial septum. Also shown in FIG. 5 are radiopaque markers 118 and 119, which in embodiments are shown to be located adjacent to the end of the flange segments.

Figure 6:
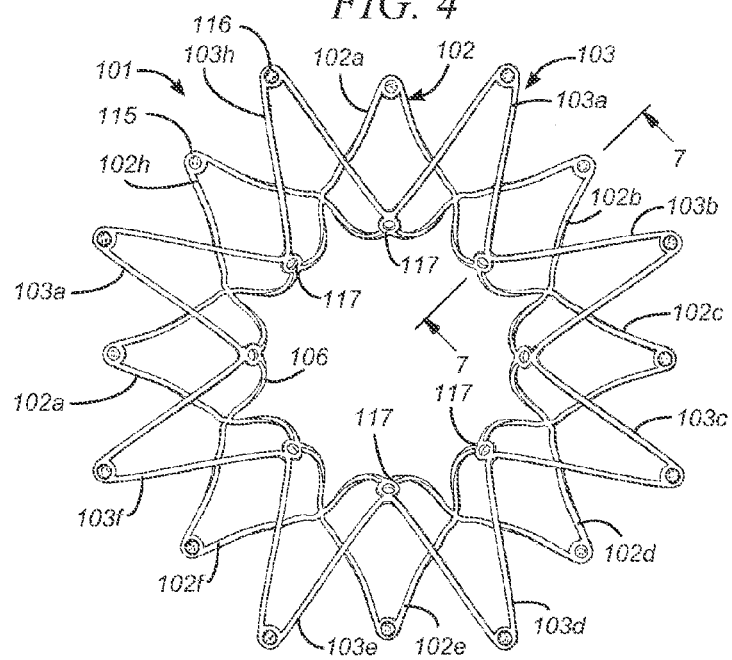
FIG. 6 is a distal end view of the body assembly of FIG. 4.

Referring now to the embodiment shown in FIG. 6, the flange segments 102a-102h are oriented so they are not directly opposed to flange segments 103a-103h on the opposite side of the body element so that after placement there is no pinching points thereby reducing the chance for tissue injury. In embodiments, flange segments 102a-102h are arranged midway between adjacent ends of flange segments 103a-103h. In embodiments the length of flange segments 102a-102h are similar to the length of flange segments 103a-103h. However in other embodiments the length of flange segments 102a-102h are identical to the length of flange segments 103a-103h; the length of flange segments 102a-102h are longer than 103a-103h; and the length of flange segments 102a-102h are shorter than flange segments 103a-103h.

Figure 7:
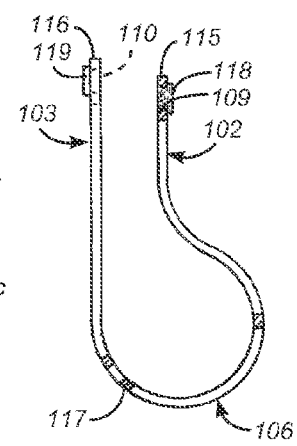
FIG. 7 is an enlarged fragmentary cross-sectional view taken along line 7-7 of FIG. 6.
Figure 7A:
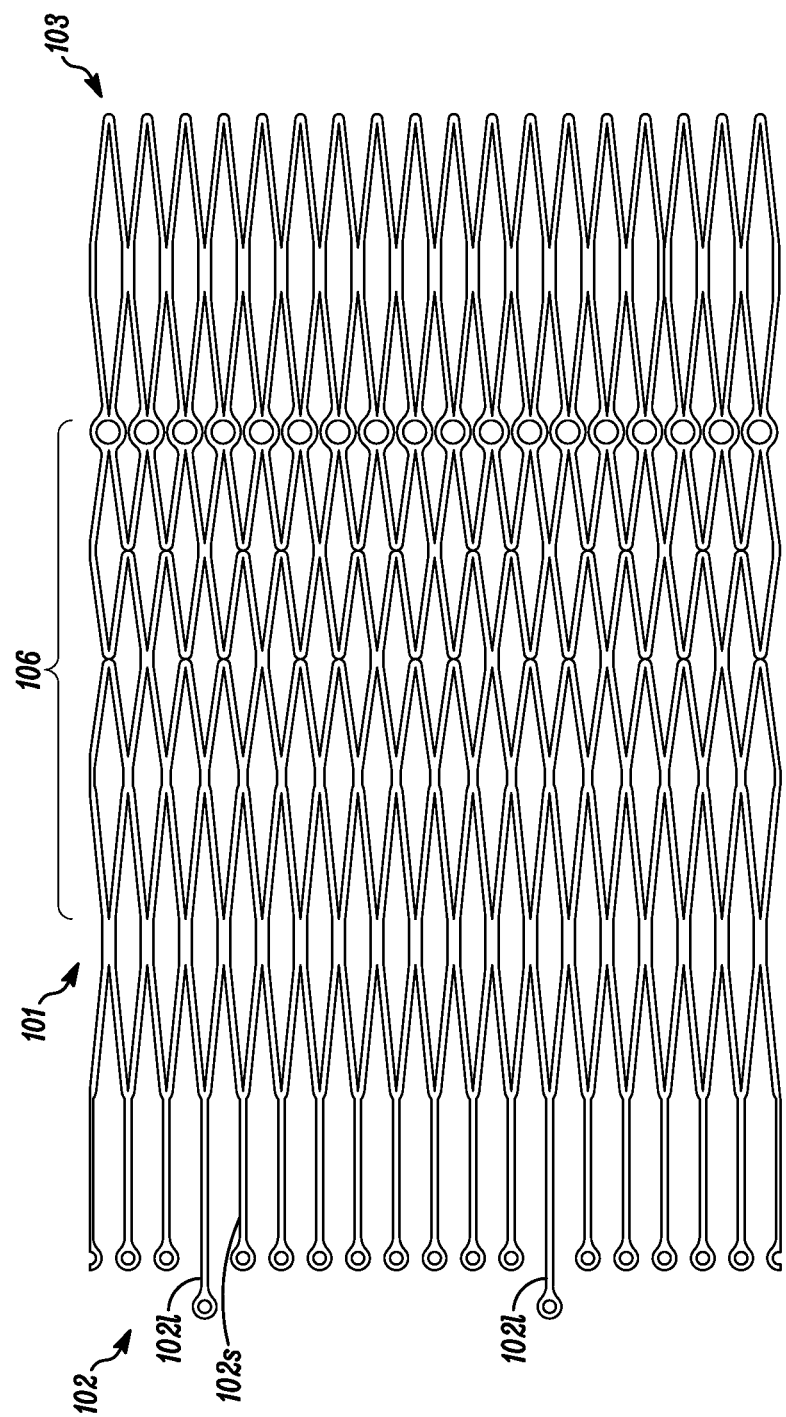
FIGS. 7A through 7C are a side elevational views of embodiments of the device in the stowed position.
Figure 7B:
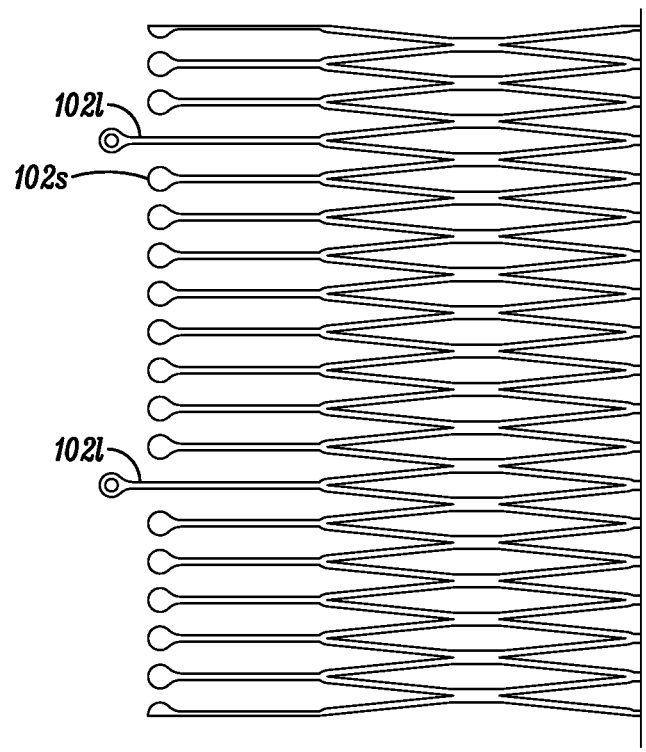
Figure 7C:
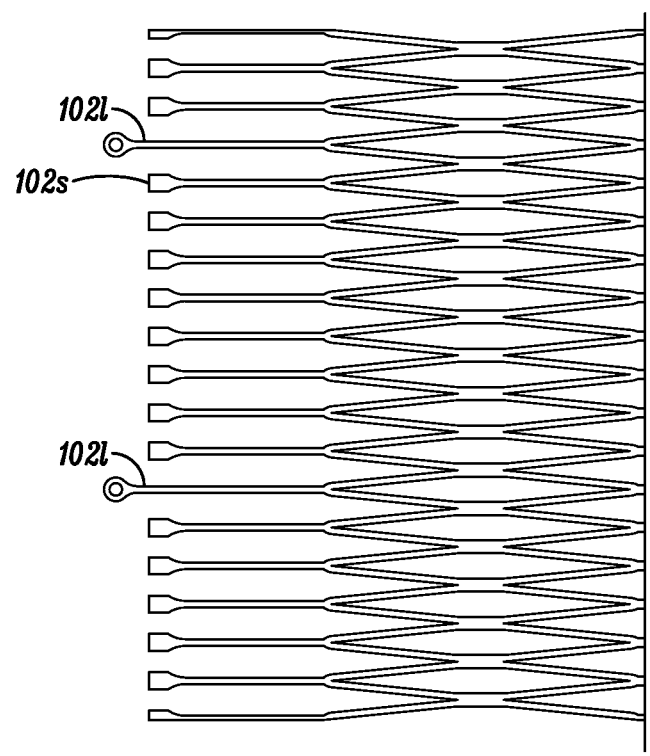

Referring now to FIG. 7, in embodiments having radiopaque markers it can be seen that the radiopaque markers 118 and 119 may be placed into the marker holes 109 and 110 (or placed on the ends of flange segments that do not have holes) to locate the ends of the flange segments 102a-102h and 103a-103h with a non-invasive imaging technique such as with x-ray or echosound during or after the procedure. In embodiments, the markers 118 and 119 can be formed to be flush in an axial direction with the outer surface and the inner surface of the flange segments 102a-102h and 103a-103h. In another aspect, the markers 118 and 119 can be formed to extend in an axial direction beyond the outer surface of the flange segments 102a-102h and 103a-103h, away from the interatrial septum. In embodiments, the markers 118 and 119 can be formed to extend in an axial direction beyond the inside of the flange segments 102a-102h and 103a-103h, toward the interatrial septum. In embodiments, the markers 118 and 119 can be formed to extend in an axial direction beyond the inside and the outside of the flange segments 102a-102h and 103a-103h. In embodiments, the markers 118 and 119 can be formed to be recessed in an axial direction within the surface of the inside of the flange segments 102a-102h and 103a-103h. In embodiments, the markers 118 and 119 can be formed to be recessed in an axial direction within the outside of the flange segments 102a-102h and 103a-103h. In embodiments, the markers 118 and 119 can be formed to be recessed in an axial direction within both the inside and the outside of the flange segments 102a-102h and 103a-103h. In embodiments, the markers 118 and 119 can be formed to extend in a radial direction within the width of the flange segments 102a-102h and 103a-103h. In embodiments, the markers 118 and 119 can be formed to extend in a radial direction flush with the width of the flange segments 102a-102h and 103a-103h.

Figure 8:
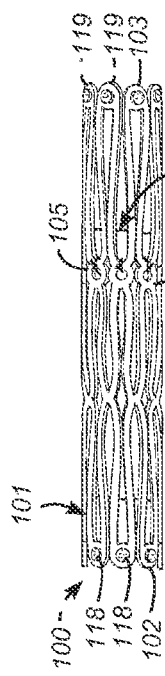
FIG. 8 is a side elevational view of the interatrial pressure vent of FIG. 1 in a collapsed configuration prior to loading in a placement catheter.

Referring now to FIG. 8, an interatrial pressure vent 100 is shown in its stowed configuration. In embodiments, the interatrial pressure vent can be collapsed to a substantially cylindrical shape for stowing in a delivery catheter during placement. Flange segments 102a-102h and 103a-103h can be fabricated to be substantially equal in length. The "stowed position" is not meant to apply only to devices having flange segments of equal length but rather to all embodiments of the venting device disclosed herein. Devices having flange segments of varying length and orientation such as those described herein are also designed to stow in substantially the same manner as shown in FIG. 8. In an embodiment 200 seen in FIG. 20, flange segments 202a-202h and 203a-203h are formed on a slanted angle so that, when marker elements are secured to the ends of the flange segments, the flange segments can be stowed into a smaller volume. In embodiments 300 seen in FIG. 21, flange segments 302a-302h are formed of alternating length to allow stowage into a smaller volume.

Figure 9:
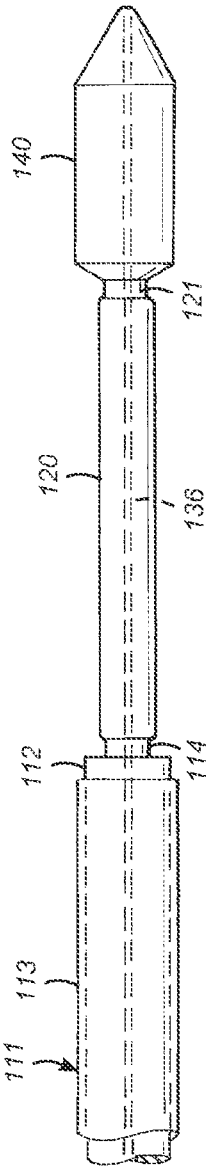
FIG. 9 is a side view of the distal end of a placement catheter in its open position.

Referring now to FIG. 9, an embodiment of the distal end of the placement catheter 111 is shown in its open position. The inner shaft 112 is fabricated with a center lumen 136 of sufficient diameter to contain a guidewire 138 or also for use in injecting contrast or other liquid. Commonly, the lumen would be sized for a guidewire of 0.010", 0.011", 0.014", 0.018", 0.021", 0.028", 0.035", 0.038", 0.042" or 0.045". This lumen 136 can also be used to measure pressure at the distal end of the catheter using other equipment and techniques that are well known to those skilled in the art. The lumen 136 preferably extends through the entire length of the inner shaft 112. Alternatively, the guidewire lumen 136 can extend for a shorter length in the proximal direction and then through a side hole (not shown) of the inner sheath. A corresponding side hole (not shown) is placed on the outer shaft 113 adjacent to the side hole in the inner shaft 112 to create a pathway between the center lumen 136 of the inner shaft 112 and the outside of the outer shaft 113. In this way it is possible to pass a guidewire from this distal end of the inner lumen 136 through the side hole and exchange the catheter over a guidewire that is less than twice the length of the catheter 111 while securing the guidewire position during exchange.

In embodiments, the inner shaft 112 is configured with a waist section 120 to contain the folded interatrial pressure vent 100 between the gap formed in the space outside of this section of inner shaft 112 and the inside of the outer shaft 113. The inner shaft 112 may be formed to contain at least one circumferential groove 114 at the proximal end of waist section 120 that forms a recess between the inside of the outer shaft 113 and the smallest diameter of the groove that is greater than the gap formed in the space between the waist section 120 and the inside of the outer shaft 113. Radiopaque markers 118 can extend in a radial direction past the outer surface of the flange segments 102a-102h and in embodiments, when interatrial pressure vents are folded into their stowed configuration and placed into position over inner shaft 112, radiopaque markers 118 are dimensioned to fit into groove 114. Other similarly dimensioned sections may be used; that is, that which fits into the groove need not necessarily be a radiopaque marker. In embodiments, when interatrial pressure vents are stowed in this manner, the gap between waist section 120 and the inside of outer shaft 113 is not sufficient to allow radiopaque markers 118 beyond the distal end of groove 114 unless the outer sheath 113 is retracted beyond the proximal end of groove 114.

The inner shaft 112 may be formed with a groove 121 on the distal end of the waist section 120 adjacent to the location of the distal end of the interatrial pressure vents are radiopaque markers 119 (or similar dimensioned members) can extend in a radial direction past the outer surface of the flange segments 102a-102h and in embodiments, when interatrial pressure vents are folded into its stowed configuration and placed into position over inner shaft 112, radiopaque markers 119 are dimensioned to fit into groove 121. In another aspect, the inner shaft 112 may be formed with a circumferential groove 114 on the proximal end of waist section 120 and a circumferential groove 121 on the distal end of the waist section 120 The inner shaft can be formed of a variety of polymers or metals or combinations of polymers and metals that are suitable for use in a patient. The inner shaft can be fabricated from a single length of PTFE, UHMWPE, FEP, HDPE, LDPE, polypropylene, acetal, Delrin, nylon, Pebax, other thermoplastic rubber, aliphatic or aromatic polyurethane, or a variety of other engineering resins that are well known to those skilled in the art. In embodiments, the inner shaft can be fabricated using multiple layers of two or three of the above-mentioned polymers to combine desirable properties of each. For example, the outer surface could be composed of polyurethane to enable easier bonding of auxiliary components to the inner shaft. The inner layer could be PTFE to convey better lubricity to the inner shaft. In embodiments, the inner shaft and or the outer shaft could be coated on the inner and or outer surface with a coating material that conveys specific properties to the shaft like antithrombogenicity or lubricity. There are numerous available coating materials suitable for these purposes as are well known to those skilled in the art. The inner shaft can be compounded with a radiopacifier to increase the visibility of the inner shaft under fluoroscopy using bismuth salts such as bismuth subcarbonate, bismuth oxychloride, bismuth trioxide, tungsten powder, molybdenum powder or other radiopacifier such as are well known to those skilled in the arts. Similarly, the outer sheath can be fabricated from the same set of materials as the inner sheath, in the same manner and using the same coatings. Embodiments described below in connection with a flange rather than circumferential groove operate in substantially the same manner as described above and herein, except the device does not necessarily have projections that fit into and are retained by the grooves.

Figure 10:
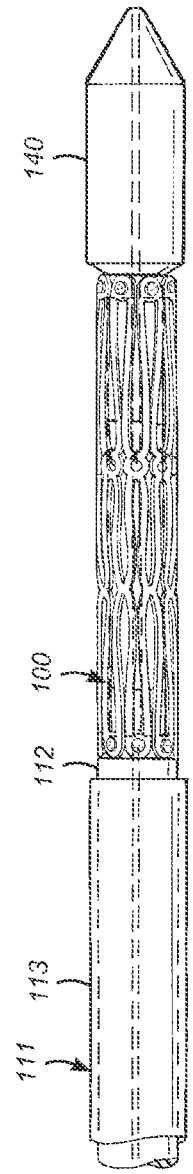
FIG. 10 is a side view of the distal end of a placement catheter in its open position and with an interatrial pressure vent in its stowed configuration and in position over the inner shaft of the catheter.
Figure 17:
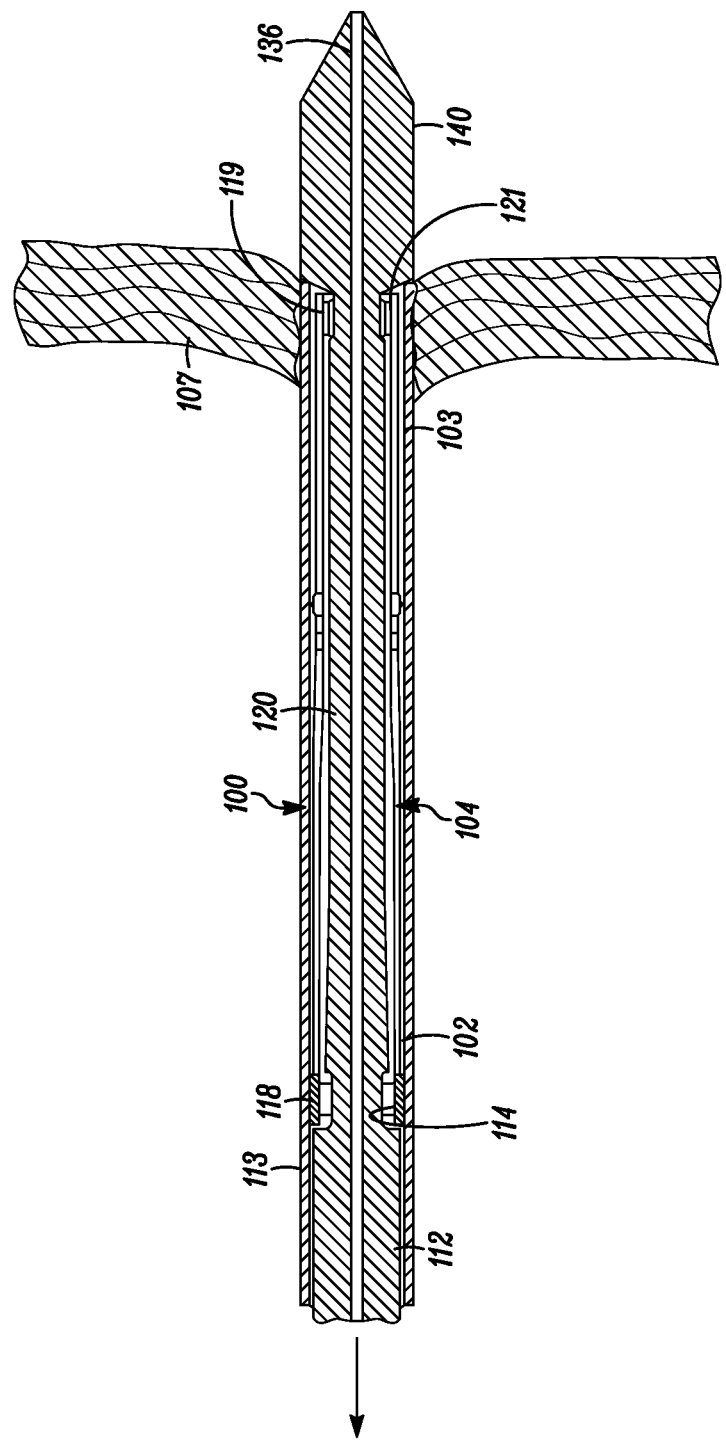
FIG. 17 is an enlarged cross-sectional detail view of the distal end of the placement catheter of FIG. 16 but showing the distal flange segments of the interatrial pressure vent being refracted from the interatrial septum as if it were determined to be in an undesirable position by imaging the radiopaque markers and going to be redeployed.

Referring now to FIG. 10, a folded representative interatrial pressure vent 100 is shown in its stowed position with the placement catheter 111 shown in its open position. In practice, if the body of the interatrial pressure vent is fabricated of nitinol or other elastic material, when the placement catheter is in its fully open position, the flange segments 102a-102h and 103a-103h would automatically recover into a shape like that shown in, for example, FIG. 4, hence this Figure is shown to illustrate the position of the interatrial pressure vent 100 relative to the waist section 120 and grooves 114 and 121. When radiopaque markers (or similarly dimensioned members) 118 extend beyond the thickness of the inside of body segment 101 of interatrial pressure vent 100, they form a projection within interatrial pressure vent 100 that can be captured within groove 114 to secure the position of the interatrial pressure vent 100 during placement. During deployment, the outer shaft 113 of placement catheter 111 is retracted a sufficient distance to reveal the distal portion of the interatrial pressure vent 100 allowing the flange segments 103*a*-103*h* to dilate radially away from the central longitudinal axis of body 101. By capturing the radiopaque 118 markers within the groove 114, the device can be repositioned easily without further deployment, or the device can be completely retracted and removed from the patient without deployment as indicated in FIG. 17.

Figure 11:
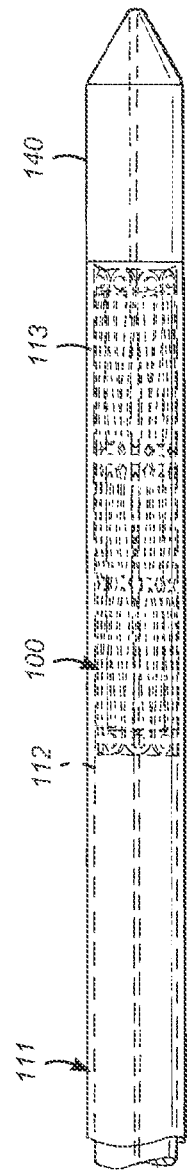
FIG. 11 is a side view of the distal end of a placement catheter in a closed configuration with an interatrial pressure vent in its stowed configuration loaded onto the placement catheter.

Referring now to FIG. 11, an interatrial pressure vent 100 is shown completely stowed within the placement catheter 111.

Figure 11A:
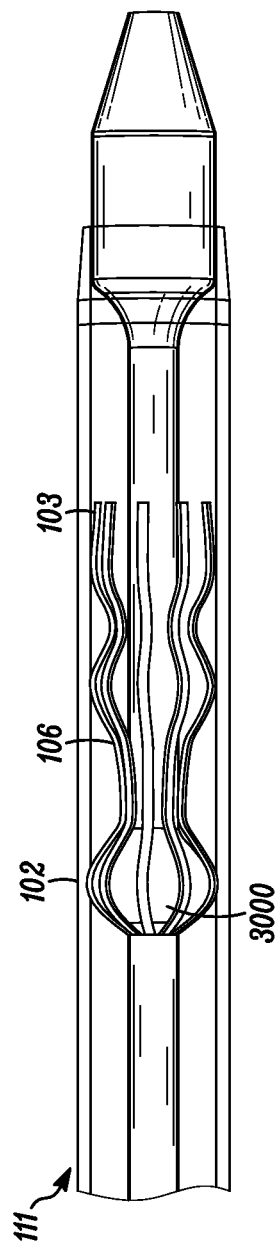
FIG. 11A is a side view of another embodiment of a placement catheter with an interatrial pressure vent stowed therein.

FIG. 11A shows an embodiment of the placement catheter similar in operation to those described herein but operative to engage an interatrial pressure vent by way of a slightly different mechanism than described above in connection with circumferential grooves. This figure shows a schematic depiction of a stowed interatrial vent. Rather than having the grooves as described above, this embodiment of a placement catheter comprises an inner shaft having a flange or member 3000 (rather than a groove) which has a diameter larger than that of the inner shaft to grip and hold an end of the interatrial vent device as shown. As shown in the figure, the flange and its segments (collectively referred to in the figure as 102) wrap around the ball-shaped flange 3000 and allow the interatrial pressure vent to be moved with the placement device in the manners described herein.

Figure 12:
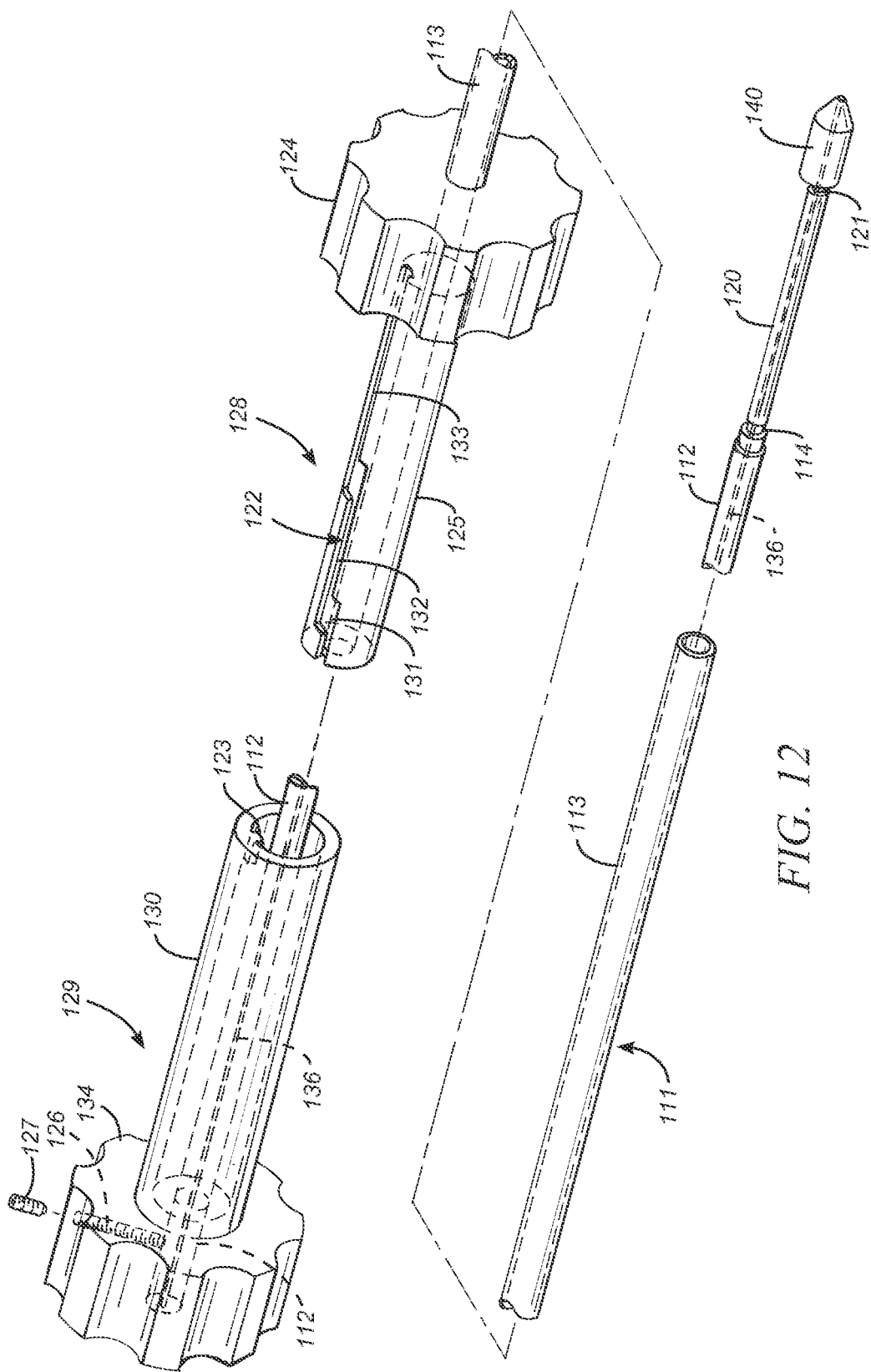
FIG. 12 is an exploded perspective view of the proximal and distal ends of a placement catheter.

Referring now to FIG. 12, a placement catheter 111 is shown. It should be noted that while the inner shaft is depicted as having grooves in FIG. 12, the inner shaft may comprise the flange 3000 as described above in connection with FIG. 11A. The skilled artisan will appreciate that the operation of the device is substantially similar whether grooves or flanges are utilized. The placement catheter 111 comprises a first handle component 128 that can be attached to outer shaft 113. The first handle component can be attached to the outer shaft 113 using a variety of adhesive methods such as solvent bonding using a solvent for both the handle and outer shaft material; an organosol consisting of a solvent and polymer in solution that is compatible with both the outer shaft and the first handle component; a polymerizable adhesive, such as polyurethane, cyanocrylate, epoxy or a variety of other adhesives as are well known to those skilled in the art. The first handle component can be fabricated from a variety of metals such as aluminum, stainless steel, titanium or a number of other metals and alloys as are well known to those skilled in the art. In embodiments, the first handle component 128 is fabricated from a polymer such as polycarbonate, or a variety of engineering resins, such as Lexan®, or others as are well known to those skilled in the art.

The first handle component comprises hand grip section 124 and tubular shaft section 125. The tubular shaft section 125 can contain keyway 122 that is formed or machined into the shaft section. The keyway is preferably formed with three linear sections; a first linear section 131, a second linear section 132 and a third linear section 133. Each of these sections is formed to traverse along a path primarily parallel with the center axis along the length of the first handle component but each is displaced radially from one another by at least about half of the width of the keyway. The placement catheter 111 also can comprise a second handle component 129 that can be attached to inner sheath 112. The second handle component can be fabricated from the same variety of metals and polymers as the first handle component. The two handles can be fabricated from the same materials or from different materials. The second handle component can be attached to the inner sheath in the same manner and using the same materials as the first handle component attaches to the outer sheath. In embodiments, the second handle component can contain threaded hole 126 for containing set screw 127. The set screw can be twisted to capture the inner shaft against the second handle component. The second handle component 129 also can comprise a second hand grip section 134 and second tubular shaft section 130. The second tubular shaft section can contain key 123 that is formed or machined of suitable dimension to adapt to keyway 122 of first handle component 128. When assembled, second handle component 129 can be slideably moved relative to first handle component 128 in a manner controlled by the shape and length of the key way 122. As the second handle 129 is advanced relative to the first handle 128, it can be appreciated that the inner sheath 112 will slide in a distal direction out from the outer sheath 113. It can be appreciated that when the second handle component 129 is assembled, the key 123 is slid into the first linear section 131 and advanced until it hits the edge of the keyway formed between the first linear section 131 and the second linear section 132. In order for the second handle component 129 to advance further, it must be rotated and, once rotated, it can be advanced further but will stop when the key 123 hits the edge of the keyway formed between the second linear section 132 and the third linear section 133. The keyway dimensions are preferably selected with consideration for the combination of lengths of other components in the placement device.

A first position, defined as the position when the key 123 is in contact with the proximal edge formed between the first linear section 131 and the second linear section 132, is preferably determined so, when fully assembled and with the interatrial vent in its stowed position within the placement catheter, the outer shaft 113 will completely cover the length of the interatrial pressure vent 100 as is desired during catheter placement. The keyway dimensions can also be selected to result in a second position, defined as the position when the key 123 is in contact with the distal edge formed between the second linear section 132 and third linear section 133. The second position would preferably be selected to reveal the full length of flange segments 103*a*-103*h* but retain flange segments 102*a*-102*h* within the outer shaft 113 of the catheter. The length of the third linear section 133 would preferably be selected so that, when the second handle component 129 was advanced completely against the first handle component 128, the full length of the interatrial vent 100 would be uncovered by the outer shaft 113 and the device would be deployed. A variety of other configurations of the first and second handle components could be used for this same purpose. The first handle component tubular shaft section 125 and the second handle component tubular shaft section 130 could be threaded (not shown) so the first handle component 128 could be screwed into the second handle component 129. Alternatively, gear teeth (not shown) could be formed in the first tubular shaft section 125 of the first handle component 128 and a gear wheel (not shown) could be incorporated into the second shaft tubular section 130 of the second handle component 129. The gear wheel would preferably be chosen to mesh with the gear teeth and the second handle component 129 could be advanced toward the first handle component 128 by rotating the gear wheel. A variety of other design configurations could be utilized to control the relative location between the first handle component and the second handle component as are well known to those skilled in the art.

FIGS. 13 through 17 show embodiments of a system for treating heart failure. More specifically FIGS. 12 through 19 show how the placement catheter is introduced and positioned in a patient and methods for placing the interatrial valve in a patient. The interatrial pressure vent 100 is presterilized and packaged separately from the placement catheter 111. Sterilization can be performed by exposing the device to a sterilizing gas, such as ethylene oxide, by exposing the device to elevated temperature for an adequate period of time, by using ionizing radiation, such as gamma rays or electron beam or by immersing the device in a fluid that chemically crosslinks organic molecules, such as formaldehyde or glutaraldehyde and then rinsed in sterile water or sterile saline. For each of these sterilization methods, consideration must be given to compatibility of the materials so device performance is not adversely affected as a result of the sterilization process. Also, the packaging design and materials must be carefully considered with the sterilization procedure, post sterilization handling and storage, environmental exposure during storage and shipment, and ease of handling, opening, presentation and use during the procedure.

In embodiments, interatrial pressure vent 100 can be assembled using components that have been pre-sterilized using one of the above methods or others that are well known and the final assembly may be accomplished in an aseptic manner to avoid contamination.

In embodiments, the interatrial pressure vent 100 can be supplied non-sterile and be sterilized around the time of use using one of the above methods or by other methods well known by those skilled in the art.

Similarly, the placement catheter 111 may be pre-sterilized and packaged separately from the interatrial pressure vent 100. Sterilization can be performed using a similar method to the interatrial pressure vent 100 or using a different method from the same choices or using some other method as is well known by those skilled in the art.

In embodiments, an interatrial pressure vent 100 and the placement catheter 111 can be supplied pre-sterile and in the same package. In another aspect, the interatrial pressure vent 100 and the placement catheter 111 can be preloaded and supplied pre-sterile.

Prior to insertion, the interatrial pressure vent 100 is preferably folded and stowed onto the placement catheter 111. This can be accomplished in a sterile field and using aseptic techniques in the following steps. First the interatrial pressure vent 100 is presented to the sterile field and the placement catheter 111 is presented to the sterile field. Second, the interatrial pressure vent 100 and placement catheter 111 are inspected for visible signs of damage, deterioration or contamination. Third, the second handle component 129 of the placement catheter 111 is retracted fully so the outer shaft 113 exposes the inner shaft 112 to the maximum extent allowed. Fourth, the interatrial pressure vent 100 is positioned in the correct orientation over the inner shaft 113 of the placement catheter 111 with the inner shaft 113 oriented through the center of the flow control element 104. Fifth, the flange segments 102 a-h and 103 a-h are folded away from each other and the flange segments 102 a-h and 103 a-h and the core segment 106 are compressed radially to fold the interatrial pressure vent 100 into a size and shape that will fit over and onto the waist section 120 of the inner shaft 112 with the distal ends 115 of flange segments 102a-h aligning with the proximal groove 114 of inner shaft 112.

In embodiments comprising a flange as described in FIG. 11A the flange segments 102 a-h and 103 a-h are folded away from each other and the flange segments 102 a-h and 103 a-h and the core segment 106 are compressed radially to fold the interatrial pressure vent 100 into a size and shape that will fit over the flange 3000 described on FIG. 11A. This folding may be accomplished with the aid of an insertion tool (not shown) that retains the interatrial pressure vent 100 in a stowed position on inner shaft 112 and then advancing outer shaft 113 over the stowed interatrial pressure vent 100 and displacing the insertion tool, thereby leaving the outer shaft 113 completely covering the interatrial pressure vent 100 and mating with the distal tapered tip 140 of the inner shaft 112. In other embodiments, this can be accomplished by hand using the fingers of one hand to hold the distal ends 115 of the flange segments 102a-102h in position at groove 114 of the inner shaft 112 and advancing the outer shaft 113 over the inner shaft 112 enough to hold the flange segments 102a-102h in place. Completion of the loading procedure is accomplished by progressively advancing the outer shaft 113 until it completely covers the interatrial pressure vent 100 as shown in FIGS. 11 and 11A. While the below discussion regarding placement of the interatrial pressure vent uses the placement device shown in FIGS. 9-11 as an example, the description on placement and the procedure therefore is also meant to apply to embodiments where the inner shaft comprises a flange rather than grooves.

Figure 13:
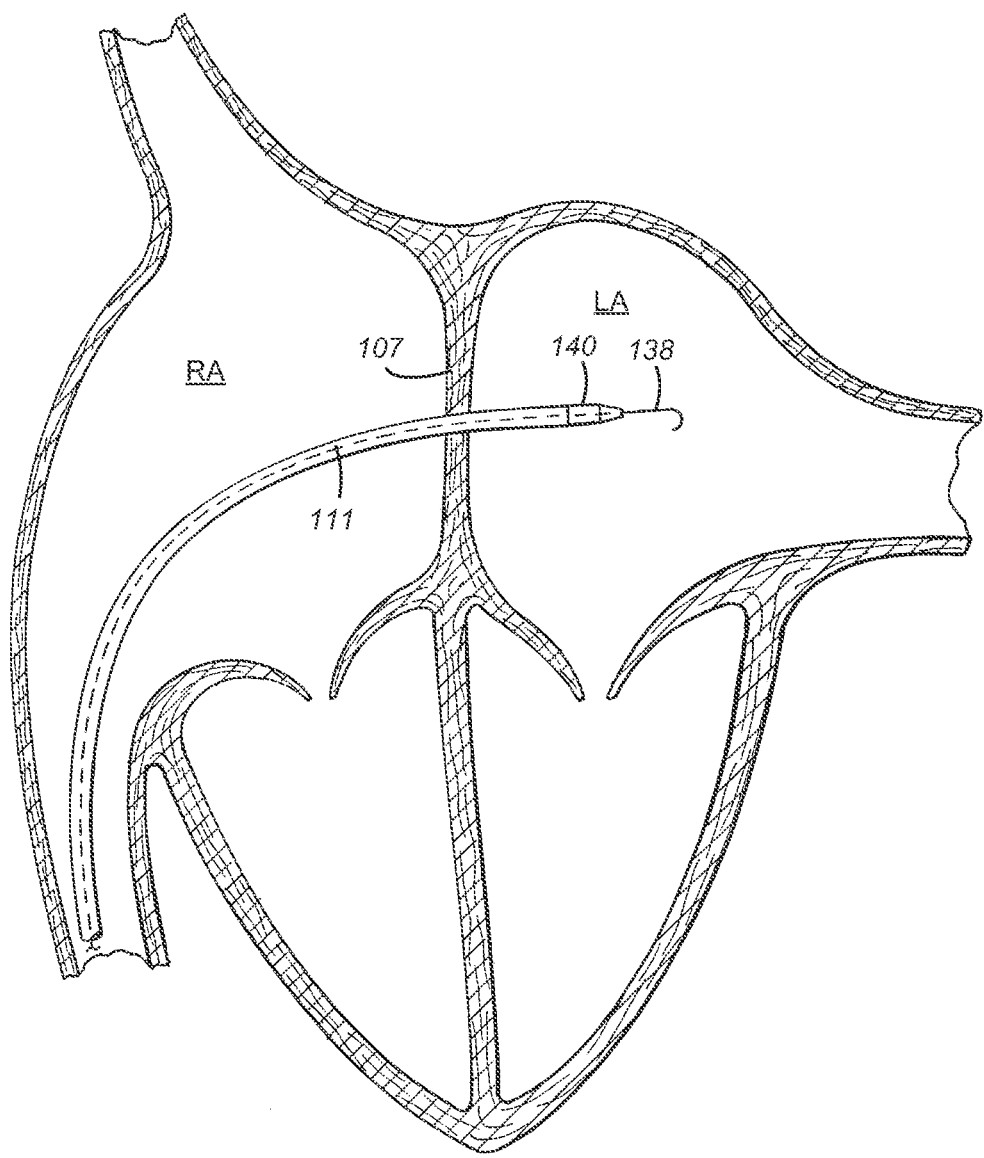
FIG. 13 is a cutaway view of a heart of a patient and the distal end of a placement catheter in position across the interatrial septum.

Positioning of the loaded interatrial valve 100 and placement catheter 111 in preparation for implanting the interatrial valve 100 in the patient can be accomplished by: first gaining vascular access; second, positioning a guidewire 121 in the right atrium of the patient; third, positioning an introducer (not shown) into the patients right atrium; fourth, locating the interatrial septum; fifth, advancing the introducer through the interatrial septum and into the patient's left atrium; sixth, advancing the guidewire 138 into the left atrium; seventh, retracting the introducer; eighth, advancing the loaded placement catheter 111 and interatrial pressure vent 100 into position so the distal end and approximately half of the stowed length of the interatrial pressure vent 100 is protruding through the interatrial septum and into the patient's left atrium as shown in FIG. 13.

In embodiments, positioning of the loaded interatrial valve 100 and placement catheter 111 in preparation for implanting the interatrial valve 100 in the patient can be accomplished by: first gaining vascular access; second, positioning a guidewire 138 in the right atrium of the patient; third, advancing the loaded interatrial valve 100 and placement catheter 111 over guidewire 138 by inserting the guidewire into and through lumen 136 and advancing placement catheter 111 into the patient's right atrium; fourth, locating the interatrial septum; fifth, advancing the placement catheter 111 through the interatrial septum and into the patient's left atrium so the distal end and approximately half of the stowed length of the interatrial pressure vent 100 is protruding through the interatrial septum and into the patient's left atrium as shown in FIG. 13.

Figure 14:
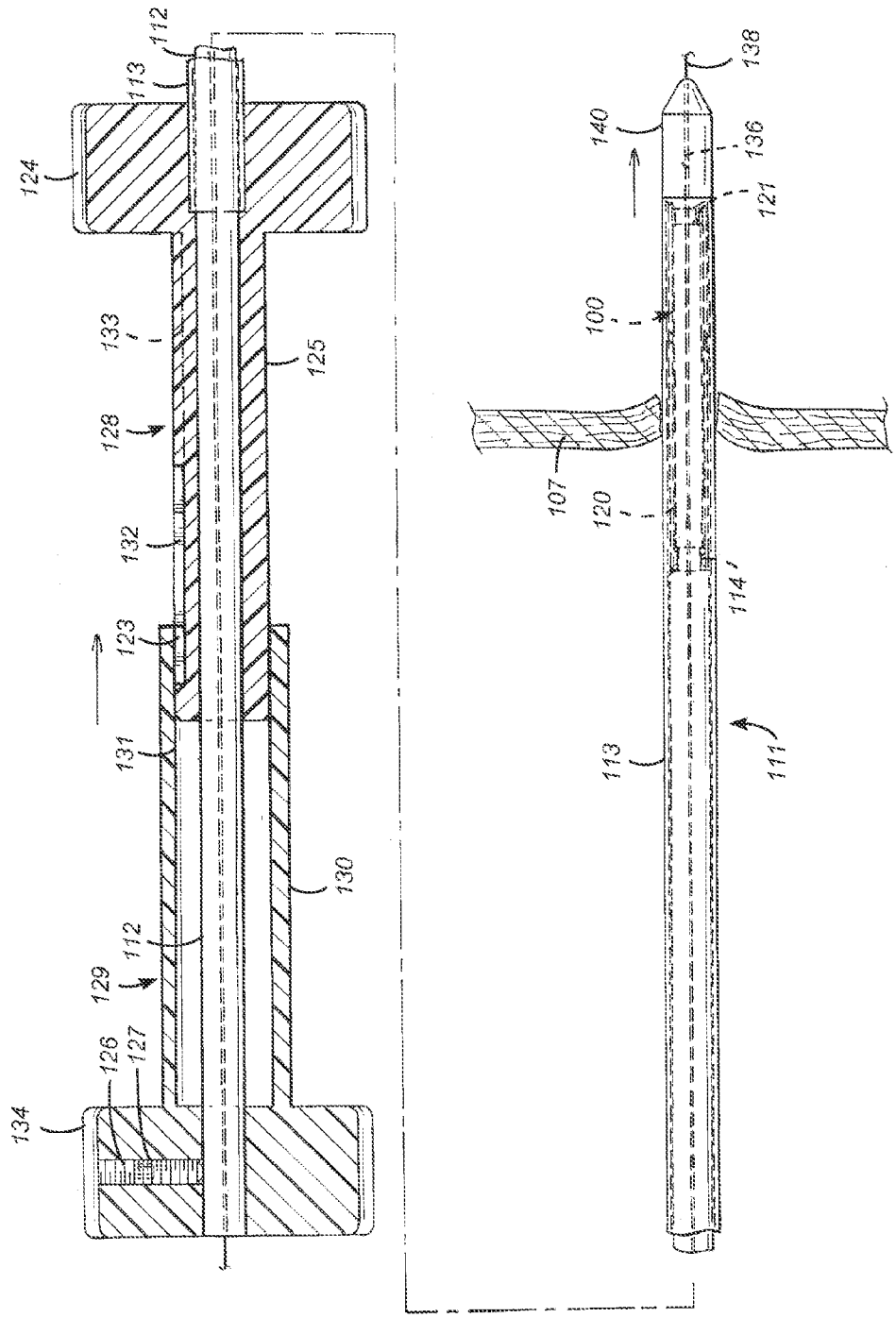
FIG. 14 is a schematic cross sectional side view of the proximal and distal end of a placement catheter in a closed position and positioned across the interatrial septum of the heart of a patient.
Figure 15:
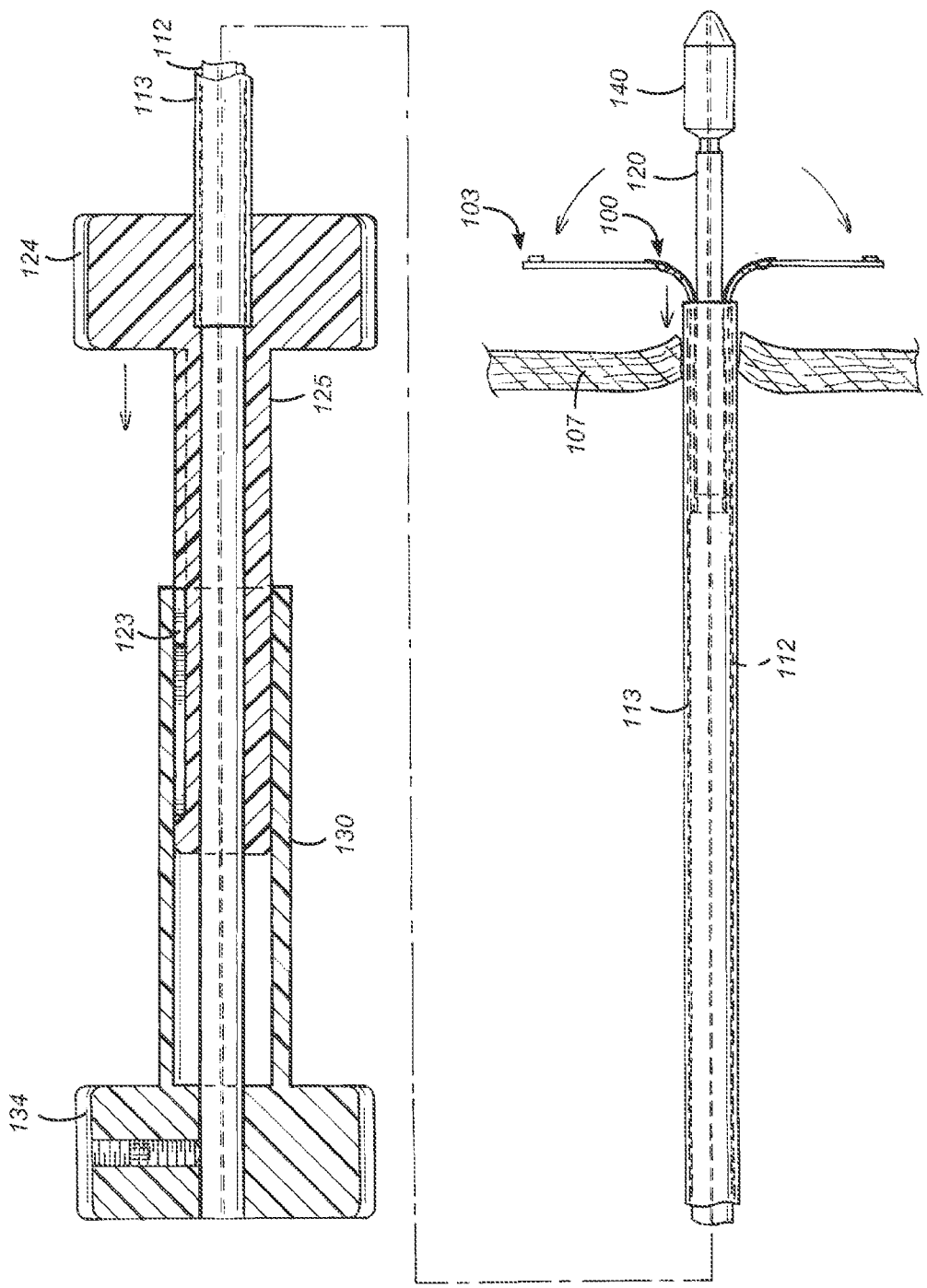
FIG. 15 is a view similar to FIG. 14 but showing the distal end of the placement catheter in a partially open position and the distal flange segments of the interatrial pressure vent deployed.
Figure 16:
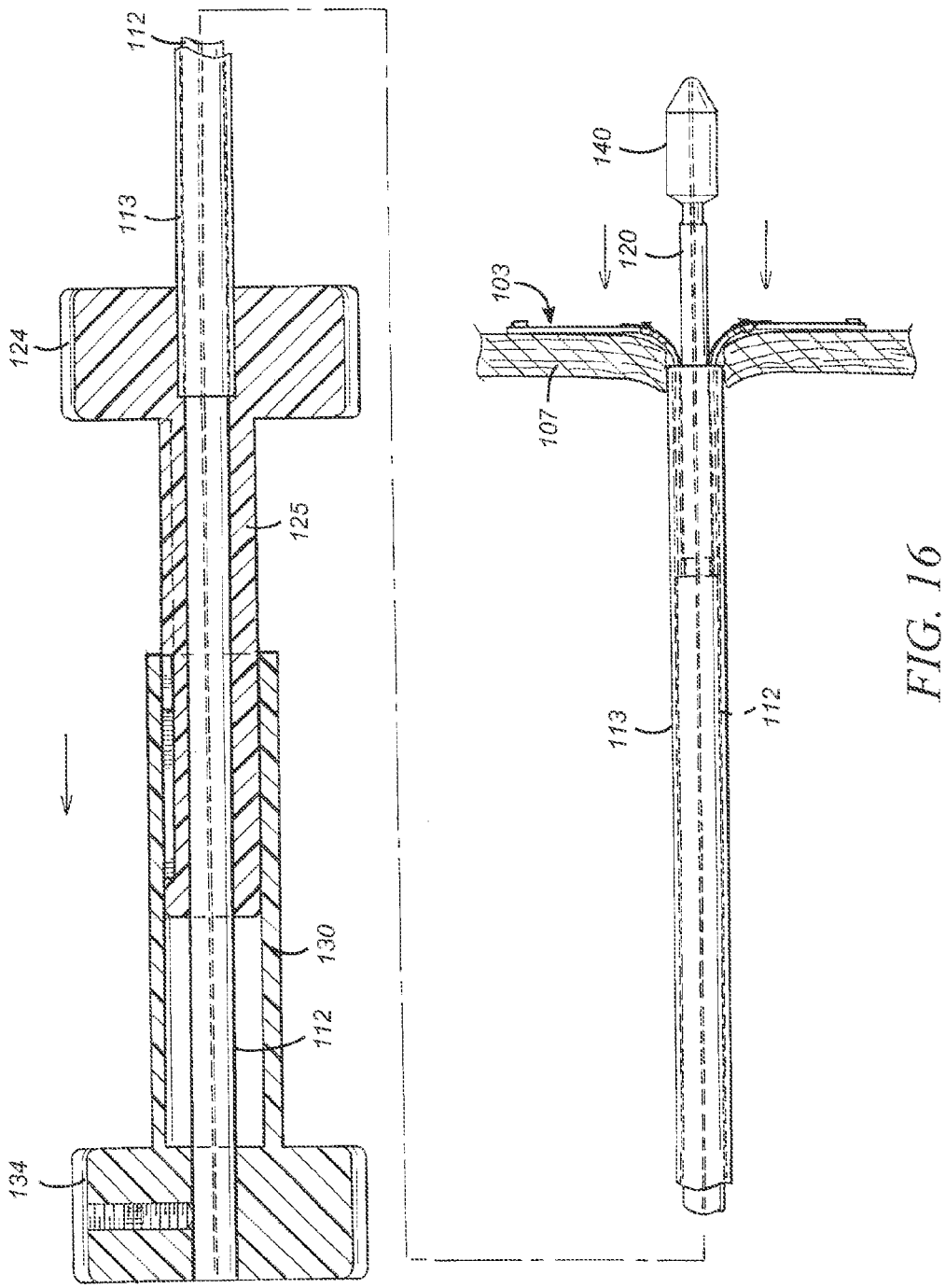
FIG. 16 is a view similar to FIG. 15 but showing the distal flange segments of the interatrial pressure vent in position against the wall of the interatrial septum.
Figure 18:
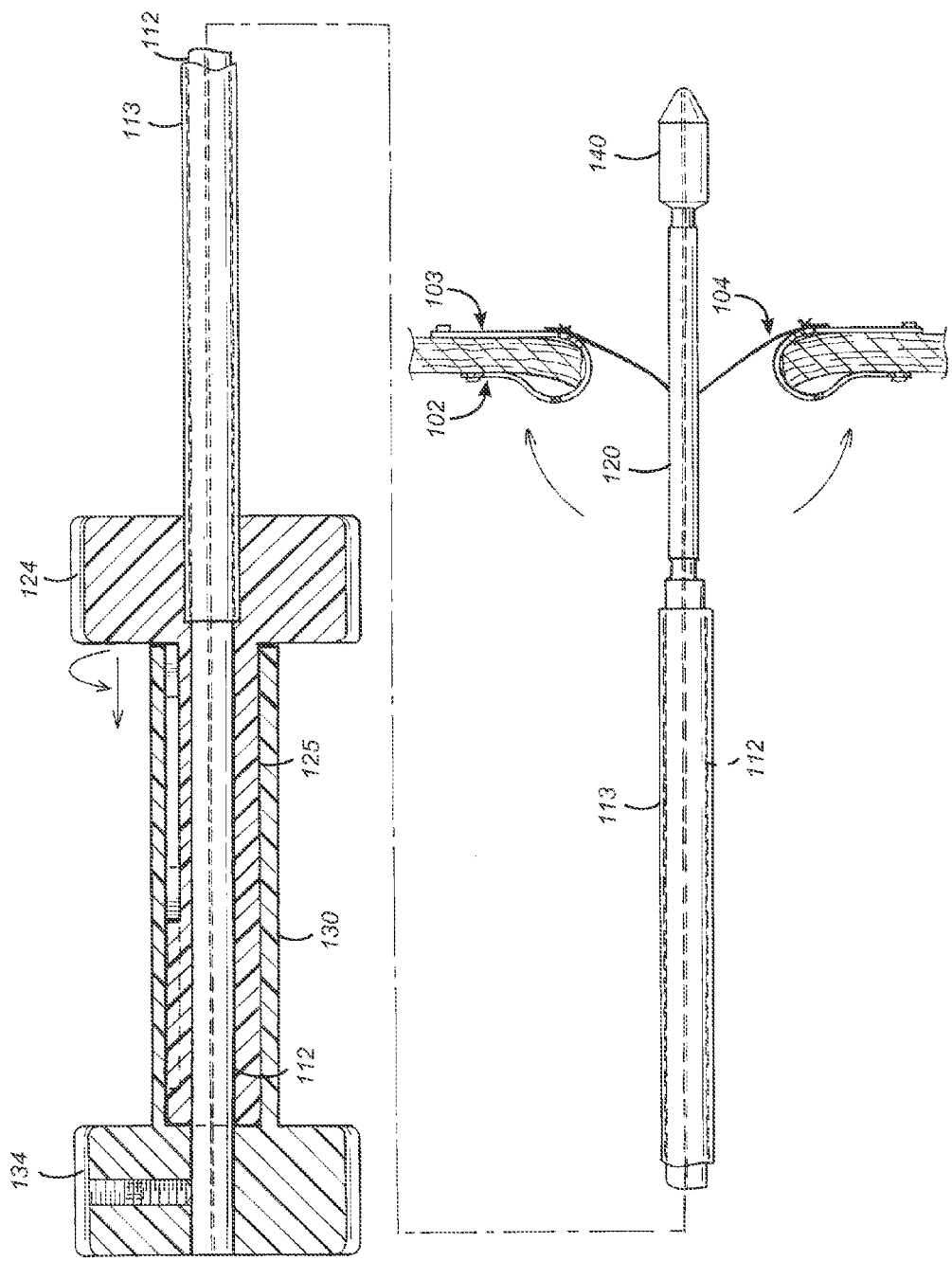
FIG. 18 is a view similar to FIG. 16 but showing further deployment of the interatrial pressure vent by releasing the proximal flange segments if imaging determines a correct positioning of the distal flange segments.
Figure 19:
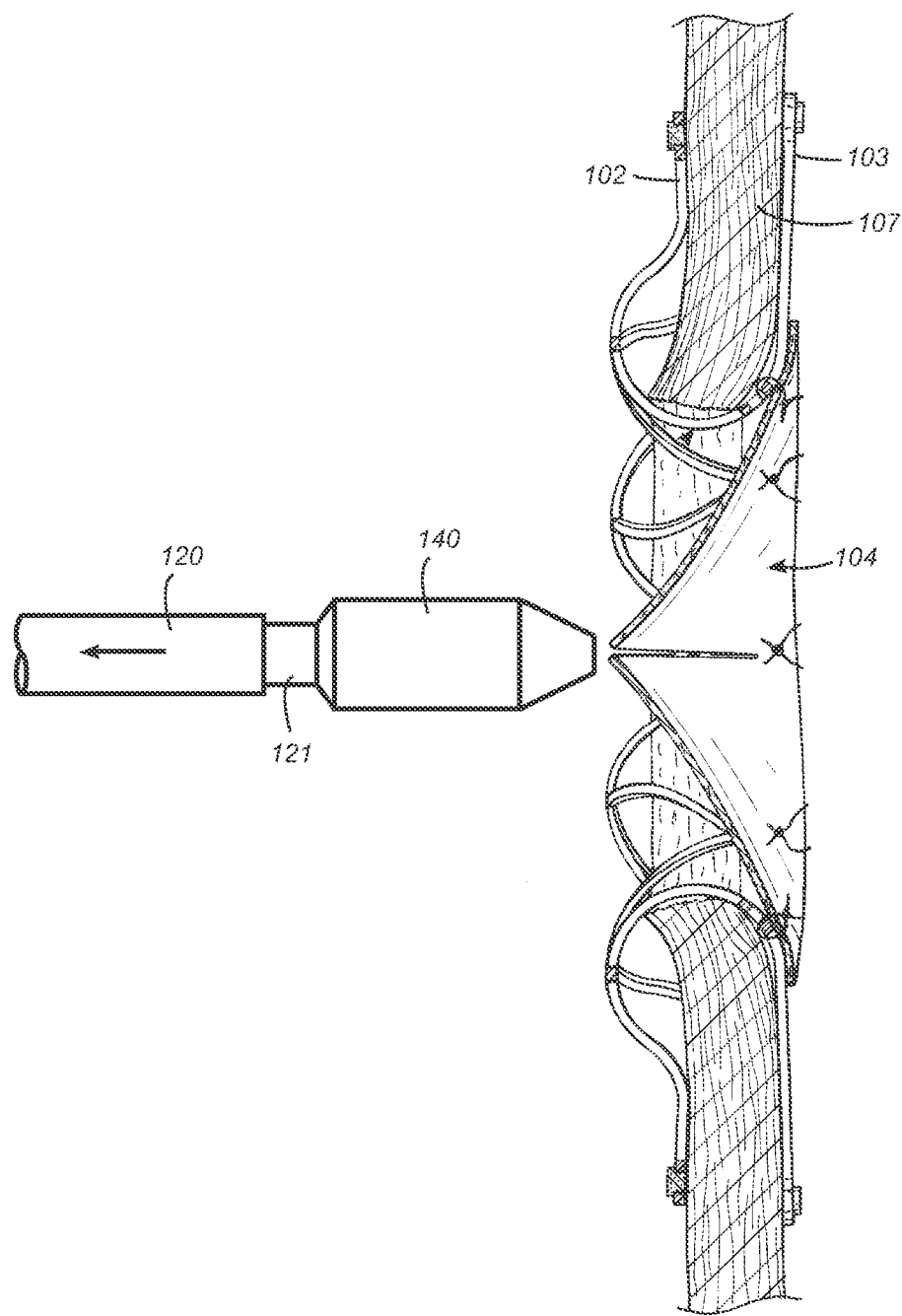
FIG. 19 is an enlarged cross-sectional detail view of the placement catheter of FIG. 18 but showing the interatrial pressure vent fully released in position and the placement catheter being removed.

Implanting interatrial pressure vent 100 into a patient can be accomplished, once the loaded interatrial pressure vent 100 and placement catheter 111 are in position as shown in FIG. 14, by first, retracting first handle component 128 toward second handle component 129 while holding second handle component 129 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by retracting first handle 128 toward second handle 129 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fifth fourth, the inner sheath is retracted through the flow control element 104 of interatrial pressure vent 100, into the patient's right atrium as shown in FIG. 19; fifth, the first handle component 128 is advanced away from the second handle component 129 to reposition inner shaft 112 into the position relative to outer shaft 113 it was in during placement and the placement catheter is removed from the patient and the procedure is completed.

In other embodiments, implanting interatrial pressure vent 100 into a patient can be accomplished, once the loaded interatrial pressure vent 100 and placement catheter 111 are in position as shown in FIG. 14, by first, advancing second handle component 129 toward first handle component 128 while holding first handle component 128 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by advancing second handle 129 toward first handle 128 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fourth, the inner sheath is retracted through the flow control element 104 of interatrial pressure vent 100, into the patients right atrium as shown in FIG. 19; fifth, the second handle component 129 is retracted away from the first handle component 128 to reposition inner shaft 112 into the position relative to outer shaft 113 it was in during placement and the placement catheter is removed from the patient and the procedure is completed.

For a variety of reasons, it may be necessary or desirable to remove interatrial pressure vent 100 and placement catheter 111 during any part of the procedure without further risk or injury to the patient. This is possible as follows: if, for any reason, it is desired for the device to be removed before outer shaft 113 is retracted and flange segments 103a-h are deployed, then the placement catheter 111 with interatrial valve 100 can simply be retracted out through the same pathway as introduced.

If, following deployment of flange segments 103a-h it is necessary or desirable to remove the device, then the interatrial valve 100 can be retracted into the placement catheter 111 by advancing first handle 128 away from second handle 129, while holding second handle 129 stationary, thereby advancing outer sheath 113 distally through the interatrial septum and over the flange segments 103a-h. In embodiments, radiopaque markers 118 placed in marker holes 109 are captured in groove 114 (see FIG. 17) and cannot fit in the gap between waist 120 of inner shaft 112 and inner surface of outer shaft 113, so as outer sheath 113 is advanced, flange segments 103a-h are forced to fold inward toward their stowed position and are retracted back onto inner shaft 112 and within outer sheath 113. Once outer shaft 113 is fully advanced, catheter 111 can be retracted as shown in FIG. 17 to be removed out through the interatrial septum and out through the same pathway as introduced.

Figure 19A:
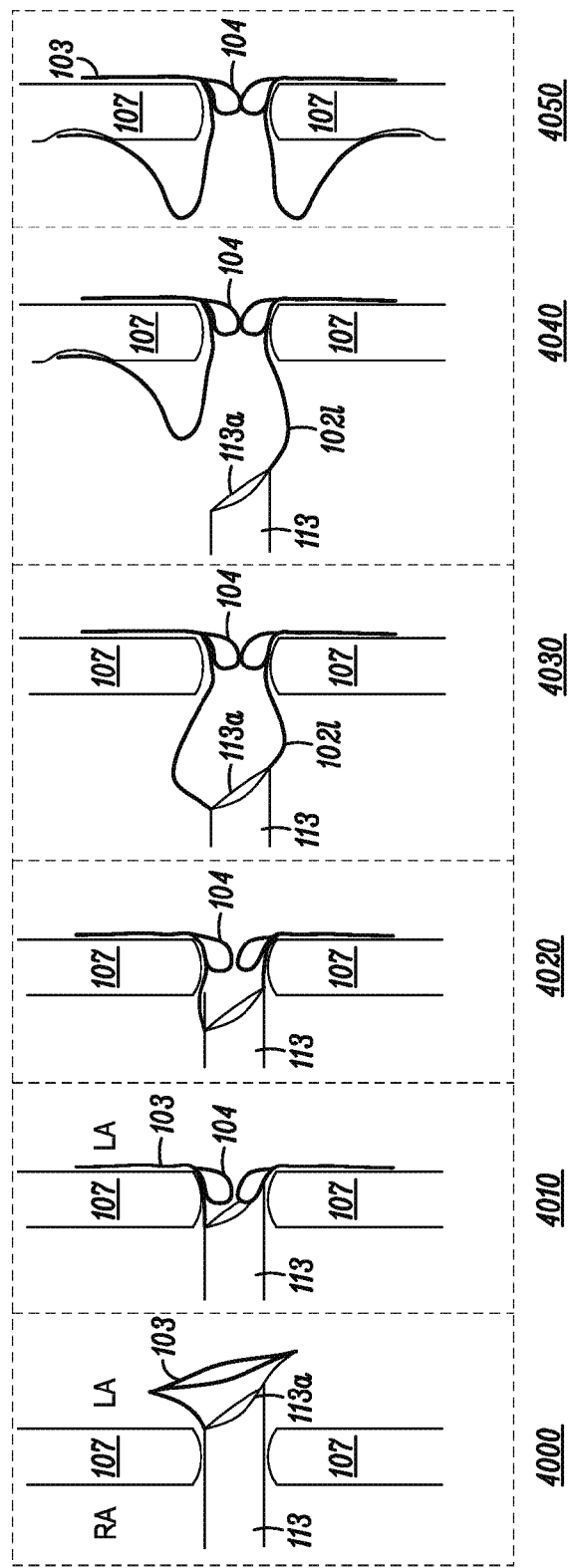
FIG. 19A is schematic depiction of another embodiment of a placement catheter system and interatrial pressure device along with the deployment process therefor.

FIG. 19A is an embodiment designed to enhance the retrievability of the device. The procedure for implanting the device is substantially similar to that which is described above; however, there are variations to the placement catheter and the device, which will be described below. As discussed in connection with FIGS. 7A through 7C, embodiments of the interatrial venting device comprise at least one flange segment being longer than the other flange segments. The embodiment schematically shown in FIG. 19A preferably works with such embodiments having at least one flange segment that are longer in relation to the other flange segments; thus the segments shown in the RA have the same reference number as the longer segments in FIGS. 7A through 7C, i.e., 102L. In embodiments utilizing the techniques shown in FIG. 19A, the opening 113a of outer sheath 113 of placement catheter is angled or has a more surface area on one side relative to the other. The placement catheter is oriented during the procedure such that the angled opening (or the plane of the opening itself) is at an angle more normal to the septal wall 107. In the embodiment shown in FIG. 19A, that angle appears to be around 45 degrees with respect to the septal wall 107, but any angle which provides an more normal angle with respect to the septal wall may be used, and any opening which provides more surface area of the outer sheath 113 on one side with respect to the other side may be used. Reference numerals 4000 through 4050 refer to steps in the process described below. The process is largely similar to that described above or with respect to any well-known placement catheter system and process, therefore only the applicable differences will be described. As can be seen at steps 4000 through 4020, the placement catheter is positioned and the device is in the beginning stages of deployment. At steps 4030 and 4040, the as the outer sheath 113 is retracted and on the RA side (or when the inner shaft is advanced while the outer sheath is on the RA side, which is not shown), the opening allows one of the longer flange segments 102L to be deployed after other flange segments have been deployed and are thus in contact with the septum 107. The at least one longer flange segment 102L is retained in the placement catheter system by way of the outer sheath 113, the length of which extends further on one side than the other due to the opening and thus covers the longer segment 102L while the other shorter segments have been deployed. In this way, the operator of the placement catheter can determine if the interatrial device is in the proper position. If not, the operator can still retrieve the device up until the last point prior to full deployment, i.e., when at least one of the longer flange segments (102L for example) is still retained in the placement catheter by the outer sheath 113. If it is in proper position, the deployment may commence.

Figure 19B:
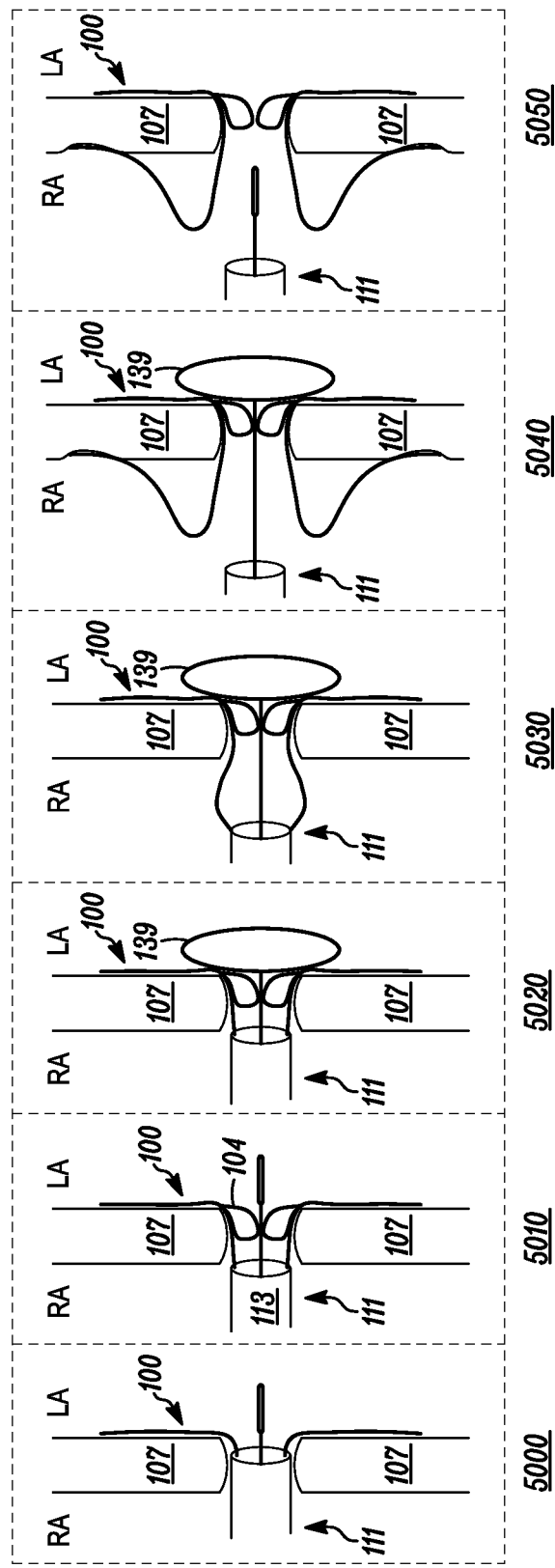
FIG. 19B is schematic depiction of another embodiment of a placement catheter system and deployment process therefor.

Another deployment embodiment is now described in connection with FIG. 19B. This deployment embodiment may be used with any embodiment of the interatrial vent described herein. Reference numerals 5000 through 5050 refer to steps in the process described below. At step 5000, the LA side of the device (generally referred to in this figure as 100) is deployed on the LA side of the heart. Further deployment is shown at step 5010 and the outer sheath is retracted into the RA side of the heart, which allows flow control element 104 to exit the placement catheter. Placement catheter is equipped with a balloon, which is in fluid communication, for example, with lumen 136 described above or guide wire 138. The skilled artisan will appreciate other configurations in which a balloon catheter may be provided in the placement catheter system. Upon deployment of the LA side flange or shortly thereafter, balloon 139 is inflated (shown in step 5020). The inflation of the balloon optionally coupled with a pulling-back motion of the placement catheter 111 holds the device 100 against the LA side of the septal wall 107 and thereby prevents the device 100 from dislodging during deployment and/or moving in a direction away from the septal wall. Step 5040 shows the full deployment of the device 100 while the balloon 139 is inflated. When satisfactory deployment is achieved, the balloon 139 is deflated and the placement catheter system is removed (shown at step 5050).

Figure 20:
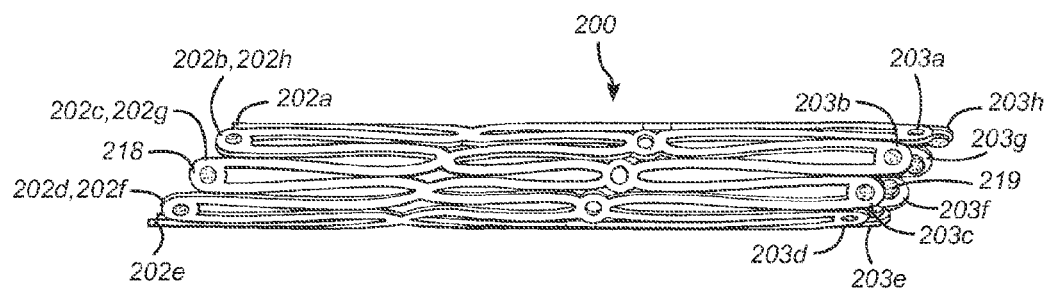
FIG. 20 is a side elevational view of an alternate embodiment of an interatrial pressure vent body with slanted flange segment ends.

Now referring to FIG. 20, an interatrial pressure vent 200 is shown. In embodiments, flange segments 202*a-h* and 203 *a-h* can be formed with graduating length to reduce interference between flange segments 202*a-h* and 203*a-h* during handling, folding and loading. In embodiments, radiopaque markers 218 and 219 protrude into the inner cylindrical shape of the stowed position of the interatrial pressure vent and each flange segment 202*a-h* and 203*a-h* differ in length by at least the width of the radiopaque markers 218 and 219. In embodiments, each flange segment 202*a-h* and 203*a-h* differ in length by at least at least 1 mm. In embodiments, each flange segment 202*a-h* and 203*a-h* differ in length by at least 2% of the overall length of interatrial pressure vent 200 in the position shown in FIG. 20.

Figure 21:
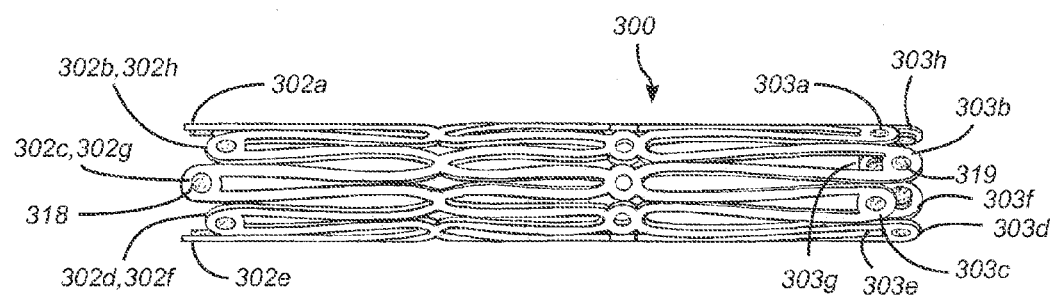
FIG. 21 is a side elevational view of an alternate embodiment of an interatrial pressure vent body with staggered flange segment ends.

Now referring to FIG. 21, an interatrial pressure vent 300 is shown. In embodiments, flange segments 302*a-h* and 303*a-h* can be formed with alternating length to reduce interference between flange segments 202*a-h* and 203*a-h* during handling, folding and loading. In embodiments radiopaque markers 318 and 319 protrude into the inner cylindrical shape of the stowed position of the interatrial pressure vent 300 and alternating flange segments 302*a, c, e,* and *g* are longer than flange segments 302 *b, d, f* and *h*, and correspondingly, flange segments 303*b, d, f* and *h* are longer than flange segments 303*a, c, e* and *g* by at least the width of the radiopaque marker. In embodiments, alternating flange segments 302*a, c, e* and *g* are longer than flange segments 302 *b, d, f* and *h* and, correspondingly, flange segments 303*b, d, f* and *h* are longer than flange segments 303*a, c, e* and *g* by at least 1 mm. In one aspect the alternating flange segments 302*a, c, e* and *g* are longer than flange segments 302 *b, d, f* and *h* and, correspondingly, flange segments 303*b, d, f* and *g* are longer than flange segments 303*a, c, e* and *g* by at least 2% of the overall length of interatrial pressure vent 300 in the position shown in FIG. 21.

Figure 22:
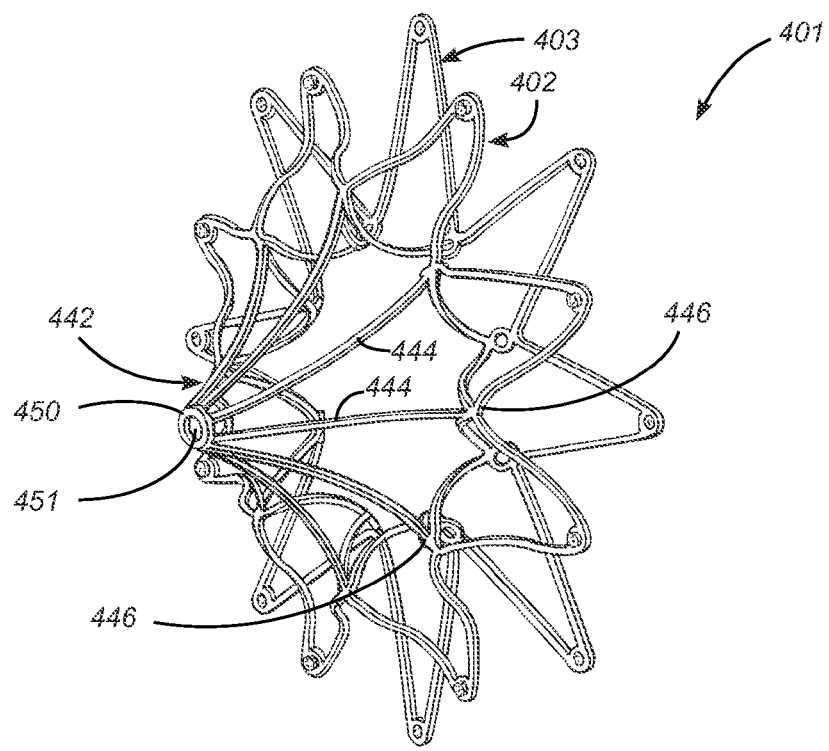
FIG. 22 is a perspective view of an alternate embodiment of an interatrial pressure vent body with an integrated retrieval means and thrombus clot strain.
Figure 23:
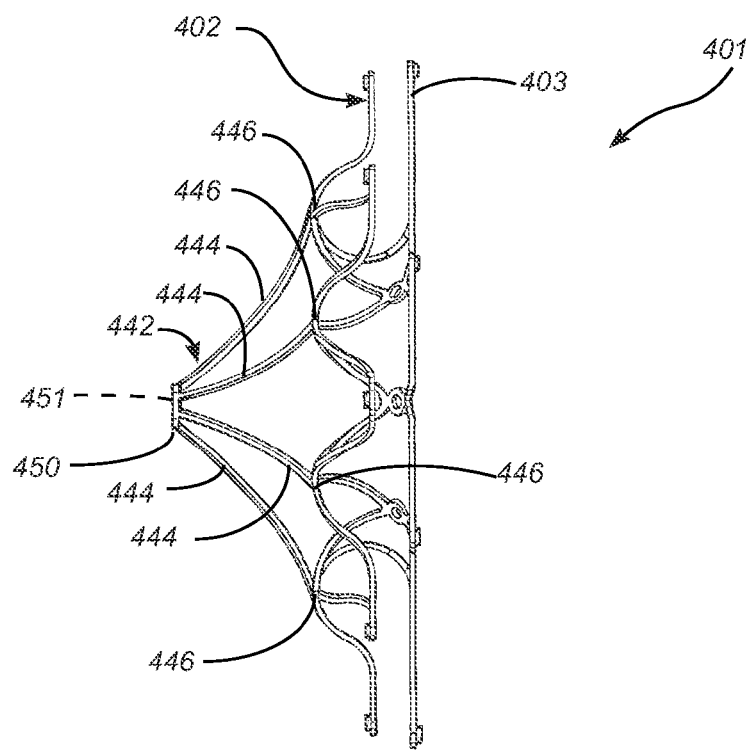
FIG. 23 is a right side view of the body assembly of FIG. 22.

Referring now to FIG. 22 and FIG. 23, the body element 401 of an interatrial pressure vent with integral thrombus filter and retrieval cone 442 is shown. In embodiments, conical struts 444 are affixed to body element 401 at attachment points 446 and converge at apex 450. In embodiments, conical struts 444 comprise single beams of similar material to flange segments 402 and 403 and can be attached to the body element or formed at the same time as the body element using techniques described in this specification, and are thus integral with the remainder of the device. In embodiments the space between adjacent struts 444 is about 2 mm. In embodiments, the space between adjacent struts 444 is about 4 mm. As can be appreciated, conical struts 444 will protrude into the right atrium of the patient after implant and spaces between conical struts will function to block the passage of solid material larger than the space between adjacent struts 444. This will provide the function of preventing emboli that are larger than the space between the adjacent struts 444 from passing from the right atrium to the left atrium.

Referring again to FIG. 22 and FIG. 23, in embodiments the shape of the conical struts 444 is not straight. In embodiments the shape of the conical struts 444 can be concave when viewed on end as depicted in FIG. 22. In embodiments the conical struts can be curved in a direction away from the chord formed between the apex 450 and the attachment points 446. In embodiments there can be a hole 451 through apex 450 large enough to receive a retrieval snare (not shown). It can be appreciated that conical struts 444 and apex 450 can be used to aid retrieval of the interatrial pressure vent from a patient at some time after the implant procedure using a method as follows: A catheter tube with an internal lumen at least as large as apex 450 can be placed into the patients right atrium using standard techniques and imaging equipment. A retrieval snare can be fabricated from the proximal end of a guidewire bent sharply by about 180 degrees and this snare can be inserted through the catheter tube and advanced into the patient's right atrium and with the assistance of fluoroscopy advanced through hole 451 or around conical struts 444. Once the retrieval snare is engaged in this manner, it will be possible to retract the interatrial pressure vent by advancing a catheter tube while holding slight tension on the snare and thereby guide the catheter tube over apex 450 and onto conical struts 444.

As the catheter tube continues to advance, with some tension on the snare it will be possible to force the conical struts inward, thereby forcing the flange segments 402 to begin folding inwards. When the conical struts are nearly completely in the catheter tube, the catheter tube can be held in a stationary position and the snare wire retracted against it, thereby causing the attachment points 446 between the conical struts 444 and the flange segment 402 to be retracted into the catheter. Flange segments 402 can begin to be retracted into the catheter at this point and the distal ends of flange segments 402 can be diverted toward the patients left atrium but will also fold inward and into the catheter. Once the flange segments 402 are inside of the catheter tube, the snare can be held stationary and the catheter tube can be advanced further, through the interatrial septum and over flange segments 403. Once the flange segments 403 are refracted into the catheter, the catheter and snare can be moved together to retract the interatrial pressure vent into the patient's right atrium and out through the pathway through which it was introduced.

Figure 24:
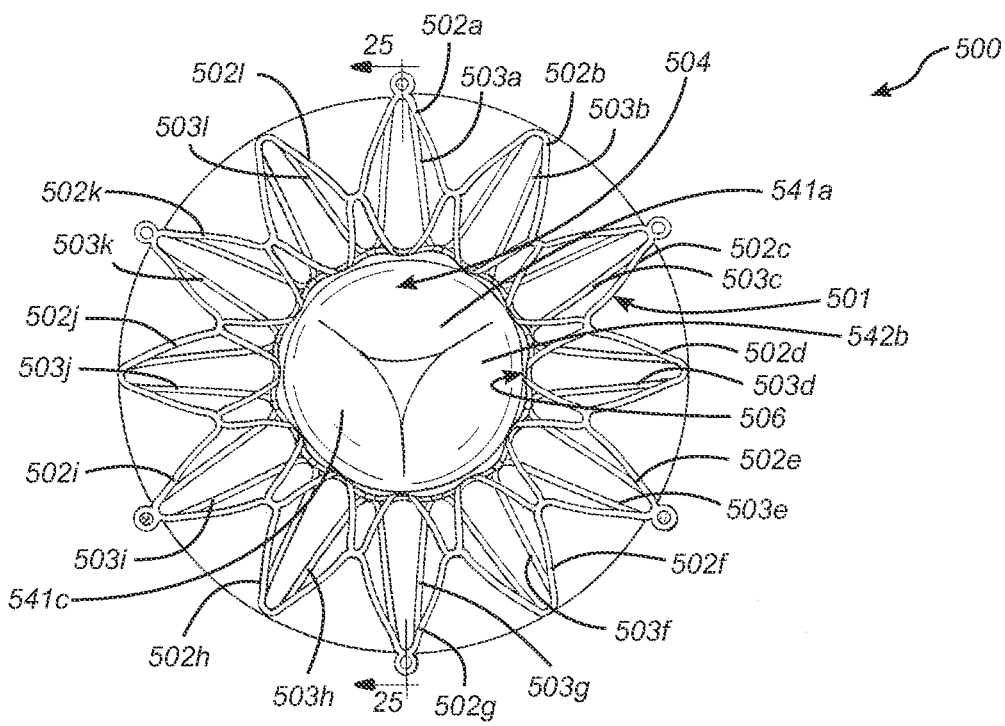
FIG. 24 is an end view of an alternate embodiment of interatrial pressure vent.
Figure 25:
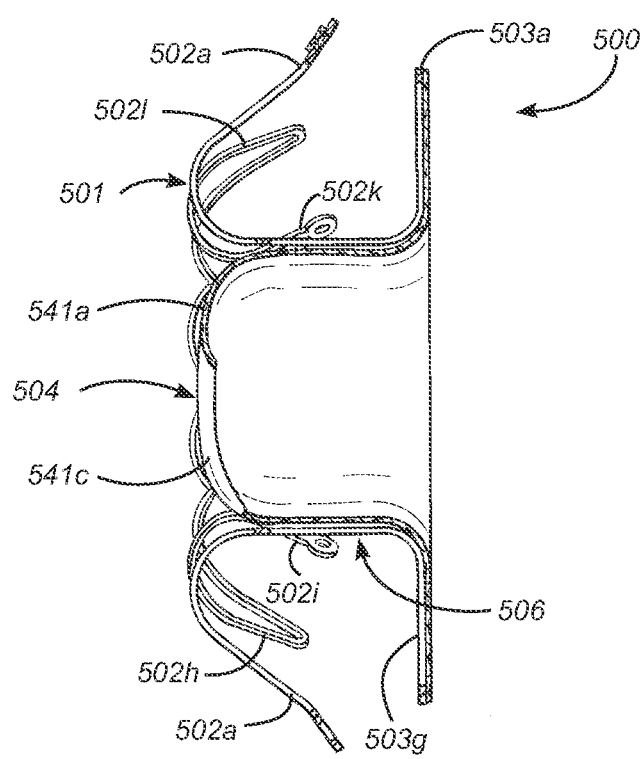
FIG. 25 is a cross-sectional side view taken along line 25-25 of FIG. 24.

Referring now to FIGS. 24 and 25 an alternate embodiment of interatrial pressure vent 500 is shown. In embodiments, flow control element 504 is comprised of leaflets 541*a-c*. Body element 501 is comprised of core segment 506 and flange segments 502*a-l* and 503*a-l* (not fully visible in FIG. 25); the number of flange segments being a multiple of the number of leaflets. This configuration improves the symmetry of strain against the flow control leaflets and also improves the uniformity of motion by the flow control element to changes in blood flow.

In embodiments the number of leaflets comprising the flow control element is three and the number of flange segments on each side of the core segment is twelve. In embodiments, the number of leaflets comprising the flow control element is three and the number of flange segments on each side of the core segment is nine. In embodiments, the number of leaflets comprising the flow control element is three and the number of flange segments on each side is six.

In embodiments, the number of leaflets comprising the flow control element is three and the number of flange segments on each side is three. In embodiments, the number of leaflets comprising the flow control element is three, the number of flange segments on one side of the core segment is twelve and the number of flange segments on the other side of the core segment is nine. In embodiments, the number of leaflets comprising the flow control element is three, the number of flange segments on one side of the core segment is twelve and the number of flange segments on the other side of the core segment is six.

In embodiments, the number of leaflets comprising the flow control element is three, the number of flange segments on one side of the core segment is twelve and the number of flange segments on the other side of the core segment is three. In embodiments, the number of leaflets comprising the flow control element is three, the number of flange segments on one side of the core segment is nine and the number of flange segments on the other side of the core segment is six. In embodiments, the number of leaflets comprising the flow control element is three, the number of flange segments on one side of the core segment is nine and the number of flange segments on the other side of the core segment is three.

In embodiments, the number of leaflets comprising the flow control element is three, the number of flange segments on one side of the core segment is six and the number of flange segments on the other side of the core segment is three. In embodiments, the number of leaflets comprising the flow control element is two and the number of flange segments on each side of the core segment is twelve. In embodiments, the number of leaflets comprising the flow control element is two and the number of flange segments on each side of the core segment is ten. In embodiments, the number of leaflets comprising the flow control element is two and the number of flange segments on each side of the core segment is eight.

In embodiments, the number of leaflets comprising the flow control element is two and the number of flange segments on each side of the core segment is six. In embodiments, the number of leaflets comprising the flow control element is two and the number of flange segments on each side of the core segment is four. In embodiments, the number of leaflets comprising the flow control element is two and the number of flange segments on each side of the core segment is two.

In embodiments, the number of leaflets comprising the flow control element is two, the number of flange segments on one side of the core segment is twelve and the number of flange segments on the other side of the core segment is ten. In embodiments, the number of leaflets comprising the flow control element is two, the number of flange segments on one side of the core segment is twelve and the number of flange segments on the other side of the core segment is eight. In embodiments, the number of leaflets comprising the flow control element is two, the number of flange segments on one side of the core segment is twelve and the number of flange segments on the other side of the core segment is six.

In embodiments, the number of leaflets comprising the flow control element is two, the number of flange segments on one side of the core segment is twelve and the number of flange segments on the other side of the core segment is four. In embodiments, the number of leaflets comprising the flow control element is two, the number of flange segments on one side of the core segment is twelve and the number of flange segments on the other side of the core segment is two. In embodiments, the number of leaflets comprising the flow control element is two, the number of flange segments on one side of the core segment is ten and the number of flange segments on the other side of the core segment is eight.

In embodiments, the number of leaflets comprising the flow control element is two, the number of flange segments on one side of the core segment is ten and the number of flange segments on the other side of the core segment is six. In embodiments, the number of leaflets comprising the flow control element is two, the number of flange segments on one side of the core segment is ten and the number of flange segments on the other side of the core segment is four. In embodiments, the number of leaflets comprising the flow control element is two, the number of flange segments on one side of the core segment is ten and the number of flange segments on the other side of the core segment is two.

In embodiments, the number of leaflets comprising the flow control element is two, the number of flange segments on one side of the core segment is ten and the number of flange segments on the other side of the core segment is two. In embodiments, the number of leaflets comprising the flow control element is two, the number of flange segments on one side of the core segment is eight and the number of flange segments on the other side of the core segment is six. In embodiments, the number of leaflets comprising the flow control element is two, the number of flange segments on one side of the core segment is eight and the number of flange segments on the other side of the core segment is four.

In embodiments, the number of leaflets comprising the flow control element is two, the number of flange segments on one side of the core segment is eight and the number of flange segments on the other side of the core segment is two. In embodiments, the number of leaflets comprising the flow control element is two, the number of flange segments on one side of the core segment is six and the number of flange segments on the other side of the core segment is four. In embodiments, the number of leaflets comprising the flow control element is two, the number of flange segments on one side of the core segment is six and the number of flange segments on the other side of the core segment is two.

In embodiments, the number of leaflets comprising the flow control element is two, the number of flange segments on one side of the core segment is four and the number of flange segments on the other side of the core segment is two.

Figure 26:
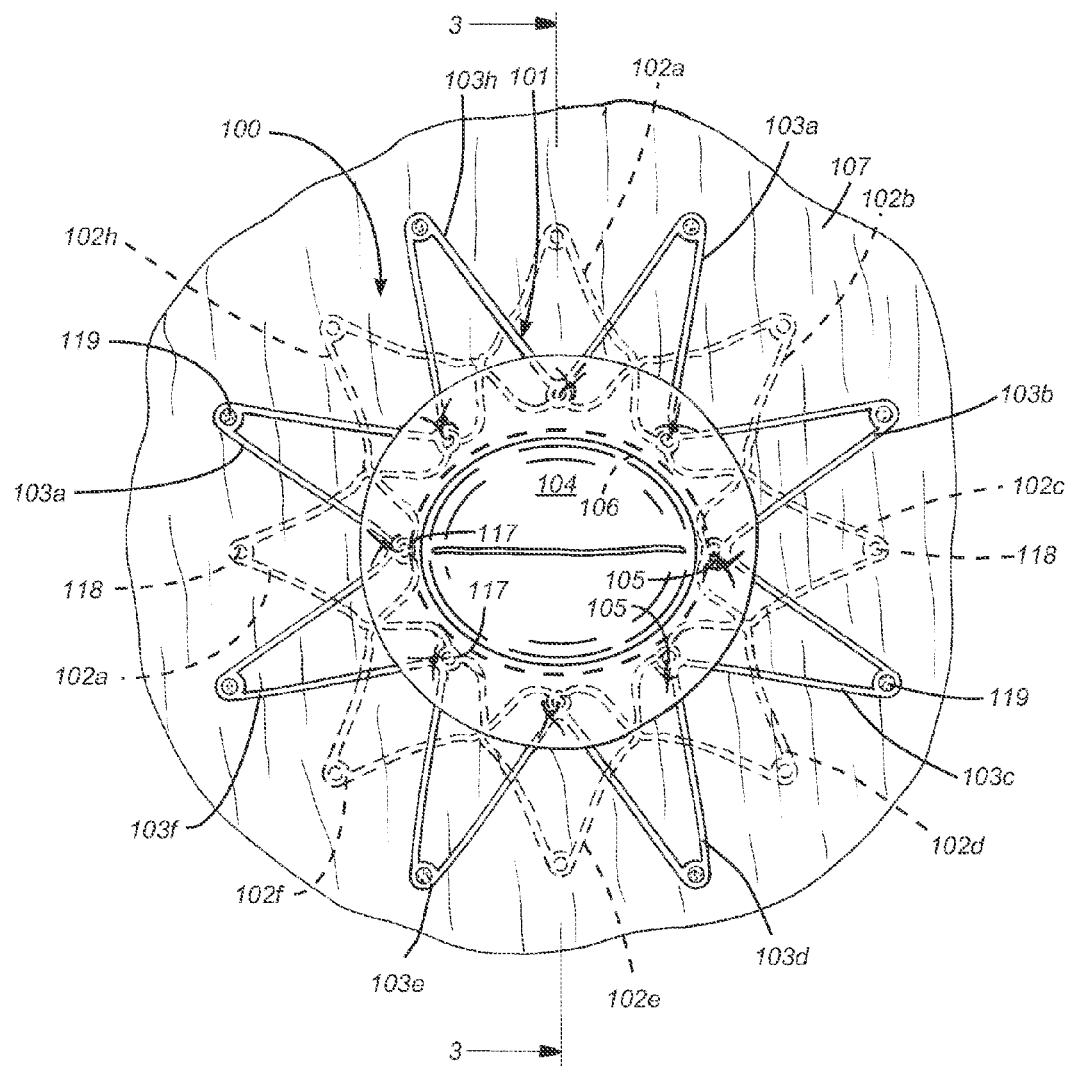
FIG. 26 shows and alternate embodiment wherein the core segment 106 is ovular rather than circular and thus the core segment is a cylindroid or elliptic cylinder rather than a simple cylinder.

FIG. 26 shows and alternate embodiment wherein the core segment 106 is ovular rather than circular and thus the core segment is a cylindroid or elliptic cylinder rather than a simple cylinder. This embodiment is more conducive to a bicuspid (or "duckbill", bivalve, or two-leaflet) configuration for the flow control element. The duckbill configuration is generally referred to as flow control element 104 in this figure. The inventors have found that the bi-valve configuration is able to open more fully when coupled with a core segment in the shape of a cylindroid.

Figure 27:
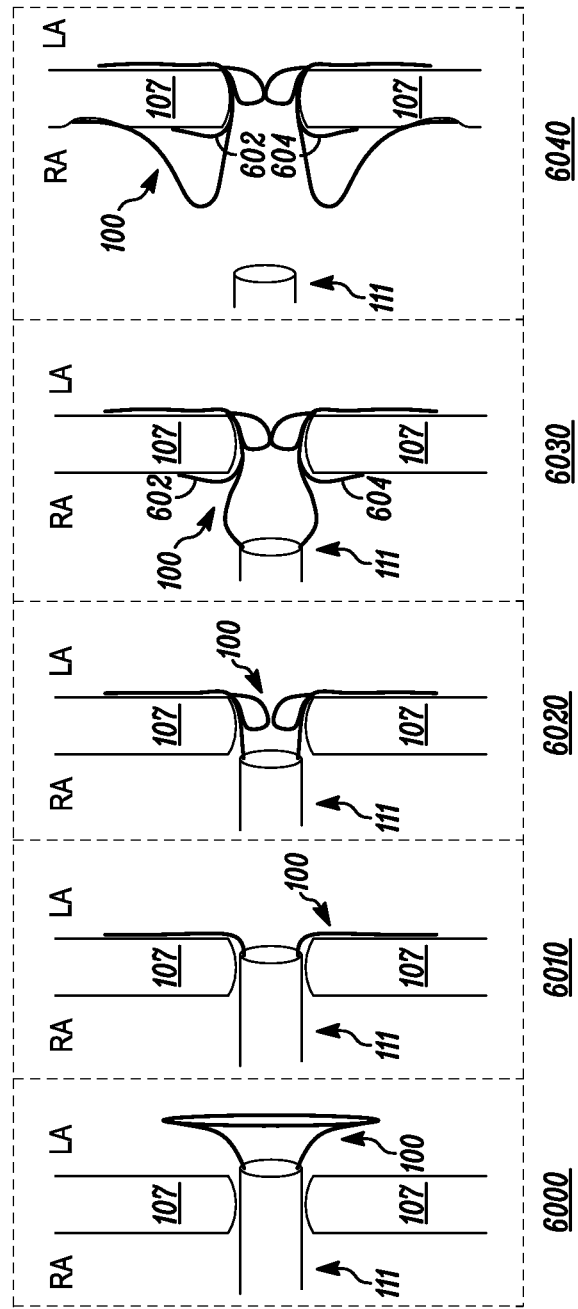
FIG. 27 is schematic depiction of another embodiment of a placement catheter system and interatrial pressure device along with the deployment process therefor.
Figure 27A:
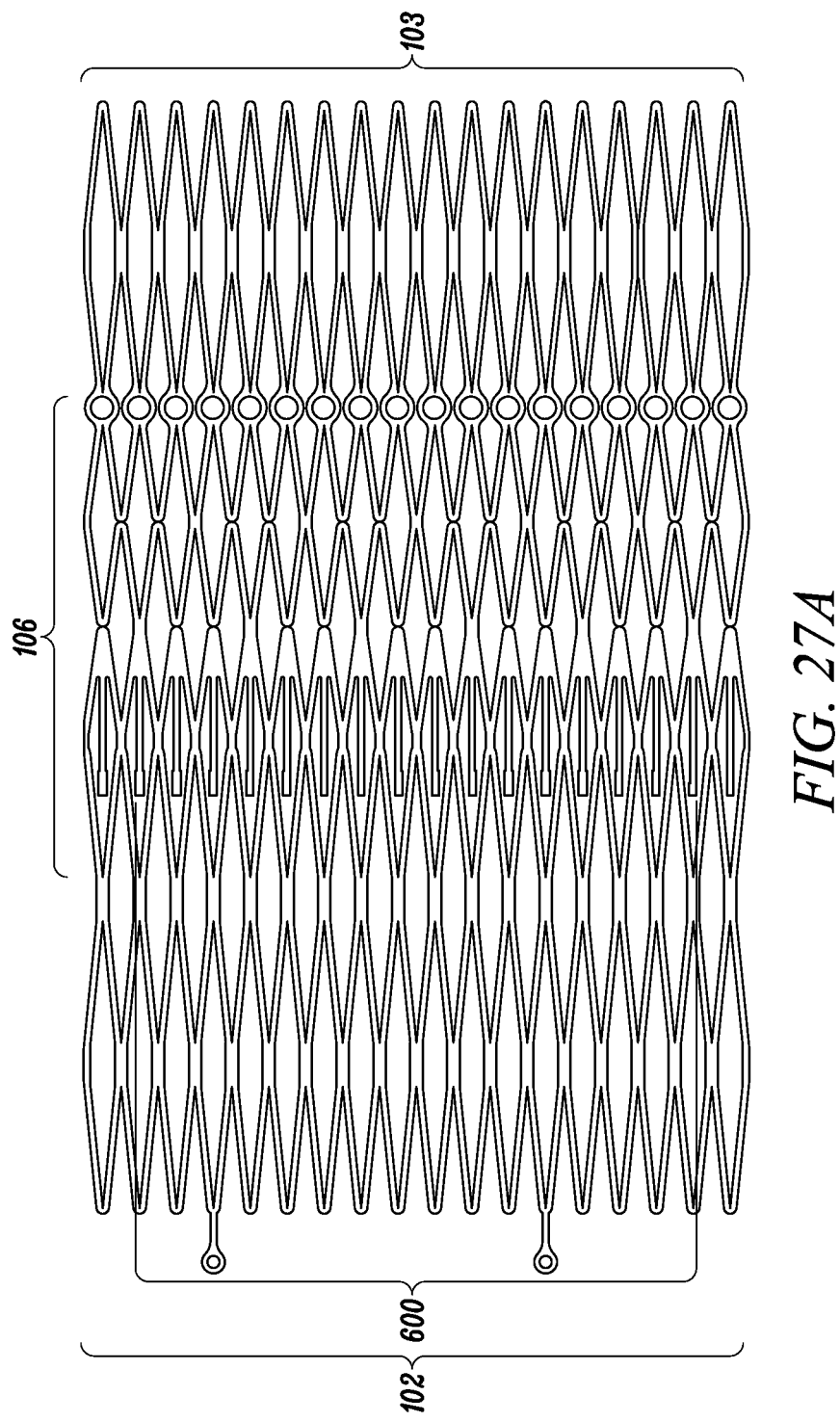
FIG. 27A is a side elevational view of the embodiment described in connection with FIG. 27 in the stowed position.

FIGS. 27 and 27A show another embodiment of an interatrial device having intermediate flange segments for a more secured fit against the septal wall. In embodiments, the intermediate flange segments are part of another a third annular flange situated on the same side of the septal wall as one of the other flanges. Reference numerals 6000 through 6040 refer to steps in the deployment of such an embodiment and will be discussed in connection with the structural features of the embodiment to illustrate this embodiment's utility and operation. The deployment process is similar to those described above, and to any commonly-known catheter based delivery process and as such the details of the process will not be discussed herein. Steps 6000 to 6020 show the deployment process steps proceeding in much the same manner as described herein. At step 6030, intermediate flange segments 602 and 604 of intermediate (or third) annular flange are deployed on the RA side. In this embodiment, intermediate flange segments 602 and 604 are shorter than the majority of the flange segments of the RA-side flange. As such, segments 602 and 604 are deployed prior to other longer segments and contact the septal wall 107 at points closer to the septal opening than the contact points of the longer segments. In this manner, the intermediate segments 602 and 604 (and the flange which they comprise) provide increased stability of the device. Any number of intermediate segments may be used although it is preferable to have at least two. As with other embodiments, the stiffness of the intermediate segments may be altered so as to differ from other flange segments of the device to avoid damage to the septal wall, i.e., lesser stiffness/greater flexibility, or to provide increased stability, i.e., greater stiffness/lesser flexibility. The choice of stiffness/flexibility variations must be balanced against the desired goals.

FIG. 27A is a side elevational view of embodiment discussed in connection with FIG. 27. In FIG. 27A the pressure venting device in its stowed configuration. Flanges 102 and 103 are shown with the flange segments that comprise them (flange segments not individually labeled). Core segment is again shown as 106. At a point between the end of the core segment 106 and proximal end of the RA side flange segment 102, the intermediate segments (collectively referred to as 600) emerge. Intermediate segments may be integral with the venting device or attached thereto in the manners described above.

Figure 28A:
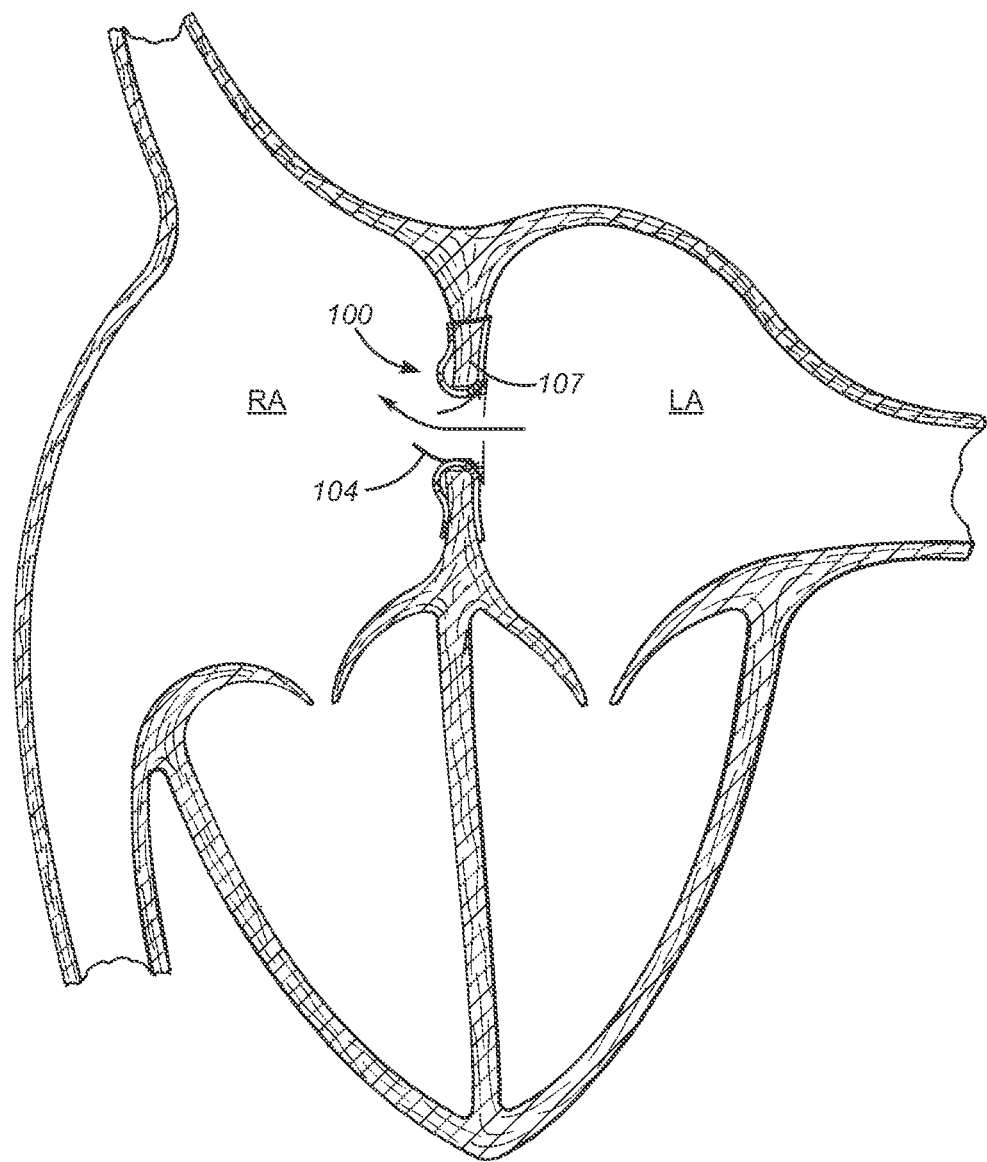
FIGS. 28A through 28C depict other embodiments of the device that direct the flow of blood in a desired direction.
Figure 28B:
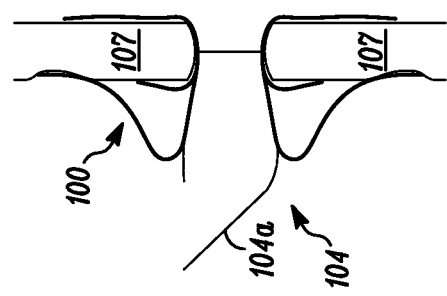
Figure 28C:
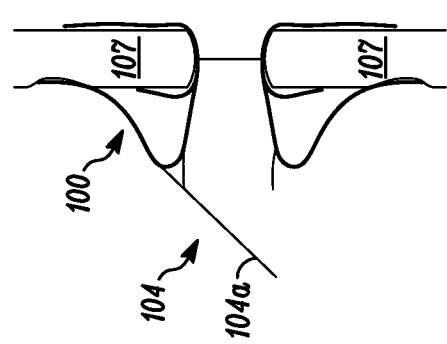

In other embodiments, the flow control element is configured to direct the blood flow in a desired direction. FIGS. 28A through 28C show such embodiments. In FIG. 28A interatrial device 100 is shown implanted in the atrial septum 107 of the heart in the same manner as shown in FIG. 1. Flow control element 104 is configured to aim the, shown in this figure as in the direction toward the superior vena cava. FIGS. 28B and 28C show a more detailed view of embodiments that enable the flow to be directed in a desired direction. As shown in FIG. 28B, flow control element comprises a baffle-like flange 104a that extends at a downward angle and in the corresponding direction. In use, such embodiment directs the flow downward. FIG. 28C shows an embodiment where the flow is directed upward. The valve material (e.g. material for leaflets) can be sized and secured to the 100 in manner to direct the flow. For example, the flow control element may contain a curved tubular member whose opening points toward the direction of flow, or the flow control element may otherwise comprise an opening directed at the area of interest. In embodiments with baffles, the stiffness of the baffle 104a may be varied, for example, made stiffer. The length of the baffle can also be varied depending on the desired flow direction. The baffle can be a separate member attached to the flow control element or it may be made of the material and/or integral with the remainder of the flow control element.

Figure 29C:
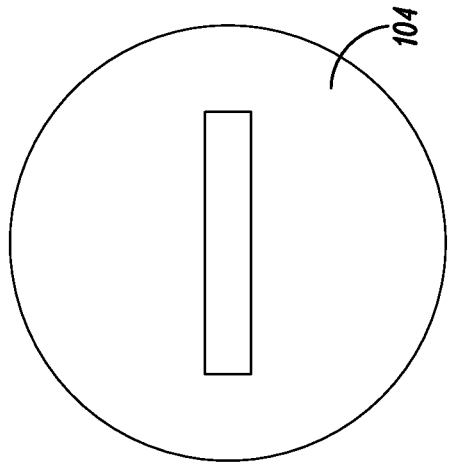
FIG. 29 is an end-on view from the RA side of embodiments of exit profiles of the flow control element.
Figure 29B:
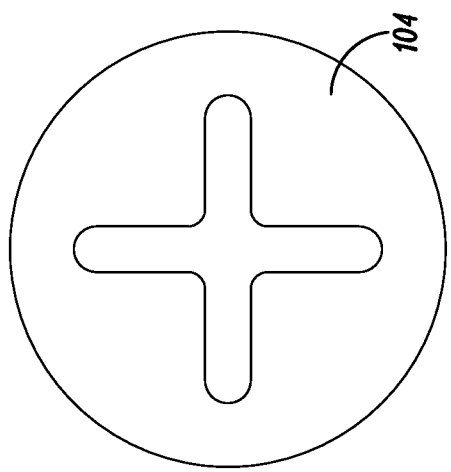
Figure 29A:
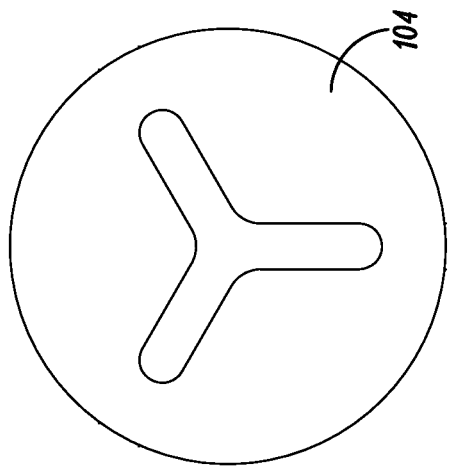

FIGS. 29A through C show exit profile shapes of the flow control element 104. In these figures, the flow control element 104 is being viewed from the RA side and thus the direction of flow is understood to coming out of the page at an angle substantially normal to the page. If the flow control element is a valve as described herein, folding and suturing patterns may be employed to achieved these exit profile shapes. In other embodiments, the end of the flow control element may be provided with a plate, or a partially frustoconical end piece, having an opening defining the two-dimensional shape shown in the Figure. The skilled artisan will appreciate that other exit profile shapes may be fashioned. The selection of an exit profile shape may provide advantages such as directing flow, preventing thrombi from moving across the septal divide, and/or reducing injury to surrounding tissue.

Figure 30:
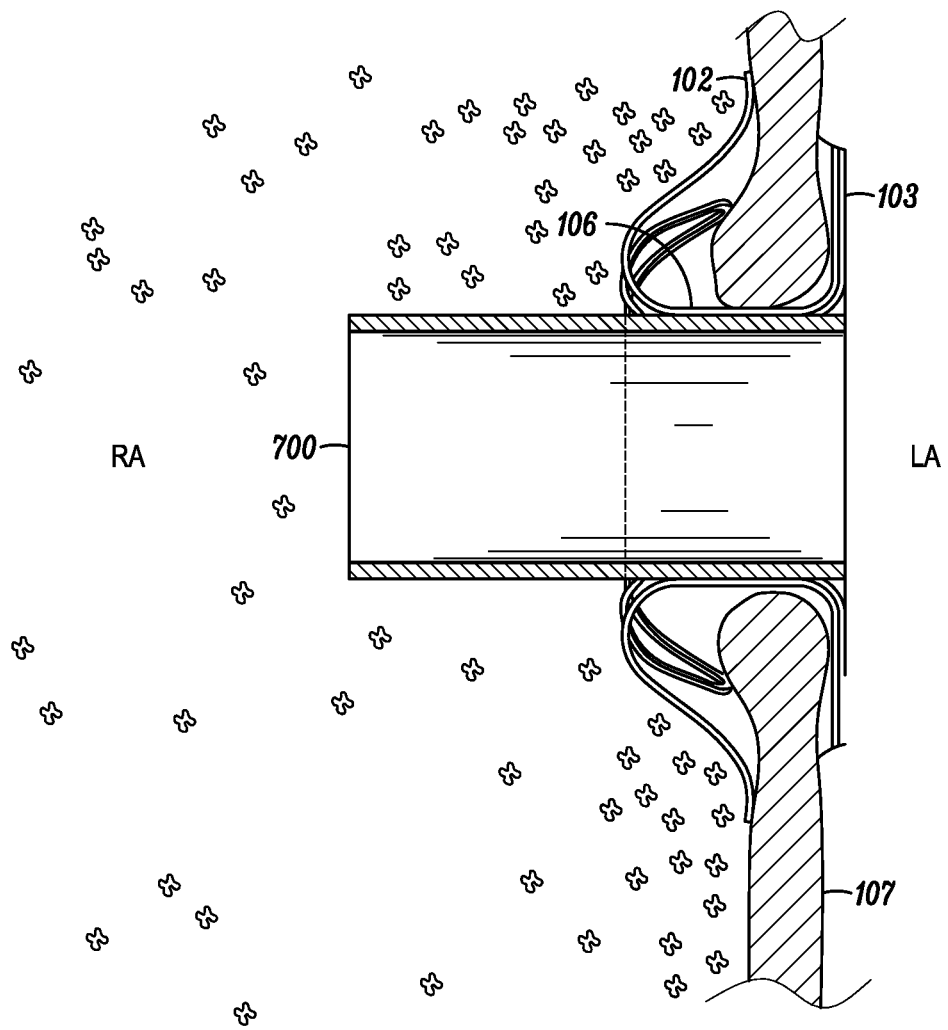
FIG. 30 is a side view of an embodiment of the device having a tube-like extension into the RA side of the heart.

Another embodiment is shown in FIG. 30. In this embodiment, the core segment 106 and flanges 102 and 103 of the device are substantially similar those described herein. Instead of the flow control elements described above (or in addition thereto) a tube-like member 700 is secured to the core segment 106. The tube member 700 is attached to the core segment 700 in a manner to allow the RA end of tube to extend into the RA in an axial direction, thus the tube's length must be sufficient to extend a distance into the RA. It has been found that the tube 700 configured in this manner prevents embolic particles from entering the tube and crossing over the septal divide into the LA. The distance that the tube 700 extends into the RA and beyond the plane of the RA-side flange opening (indicated by dotted line) should be at least a 1 mm but may be up to 2 cm in preferable embodiments. Even at relatively short lengths (such as where the tube extends only a few millimeters into the RA), the inventors have noted the surprisingly unexpected result of a reduction of embolic particles passing through. This is due to, in part, the tendency of embolic particles to collect along the surface of the septal wall and move toward the septal opening (or opening of an implanted device) with each cycle of the heart. By extending away from the septal wall 107, the tube provides an effective barrier to the embolic particles that would otherwise travel toward and possibly through the septal opening.

Placing the Interatrial Pressure Vent or Prosthesis into a Mounting Tool

Figure 31:
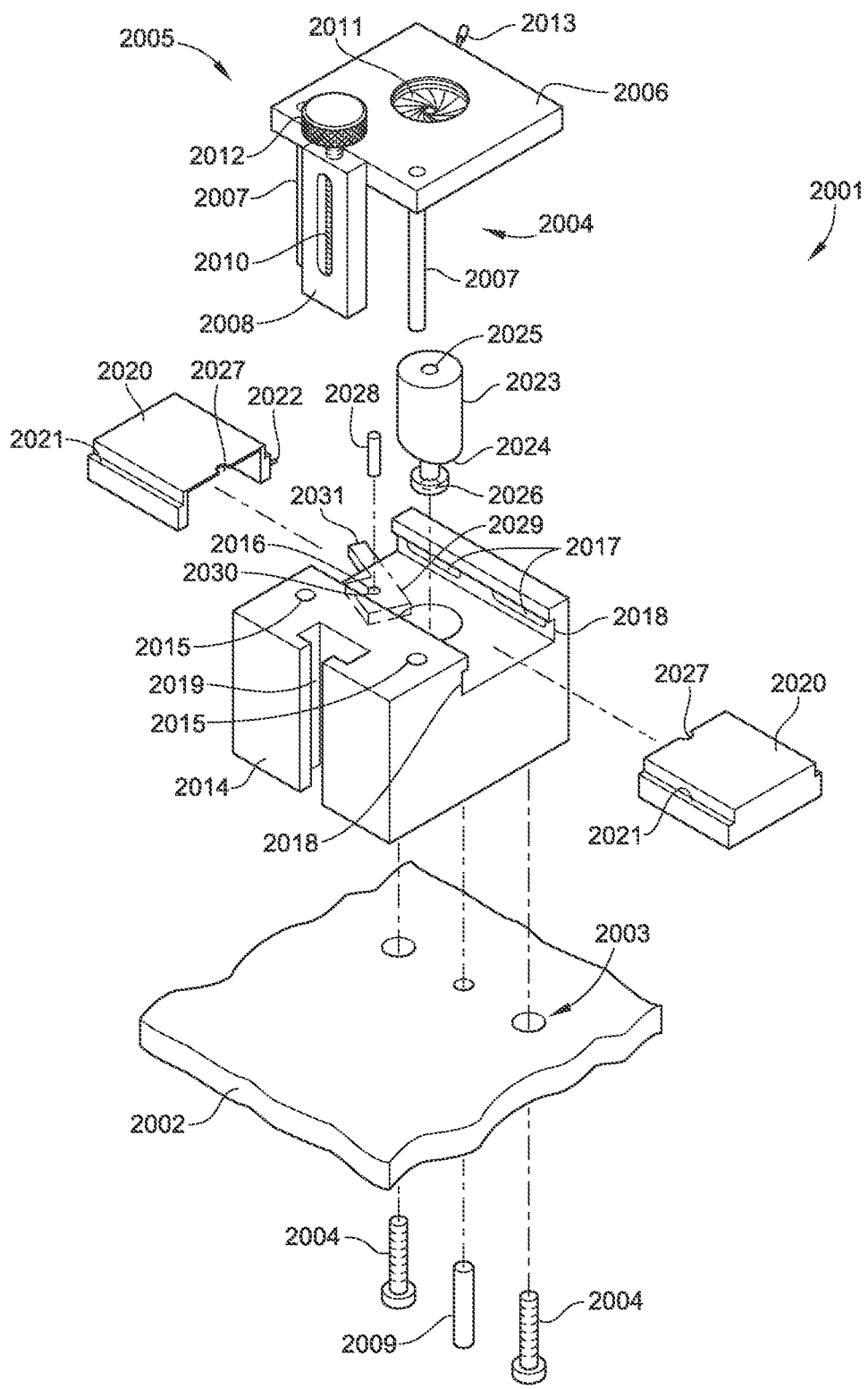
FIG. 31 depicts an exploded view of a first embodiment of a mounting and loading tool for mounting and loading a prosthesis.

FIG. 31 depicts a first embodiment of a mounting and loading tool useful for placing the prosthesis onto a catheter or other delivery device for delivery in vivo to a patient. In this embodiment, mounting tool 2001 includes a base plate 2002 with orifices 2003 for securing other components as shown with fasteners 2004 and pin 2009. The principal component is a loader body 2014, mounted via the outer two fasteners and orifices as shown. A mounting platform 2023 is mounted in the center of the loader body via the third orifice and pin 2009. Mounting platform 2023 includes a lower orifice 2026 for mounting to the loader body via the middle loader body orifice with pin 2009. Mounting platform 2023 also includes a slotted cam surface 2024. Pivot 2029 mounts to the loader body 2014 via pivot pin 2028 through pivot orifice 2030 and loader body orifice 2016. Pivot 2029 and lever 2031 mount on the left side of loader body 2014 below the side doors 2020, as seen in FIG. 31. Movement of pivot 2029 and lever 2031 on the cam surface allows a user to raise and lower the mounting platform. The two opposite positions of the mounting platform are the lower and upper positions, achieved by rotating the pivot to the desired position. In other embodiments, the cam surface may simply be a slot or groove in the side of the mounting platform 2023.

The loader body 2014 also mounts the other components of the device. The loader body includes internal side channels 2018 for mounting two side doors 2020 and also includes vertical bores 2015 and a vertical side channel 2019 for mounting top plate 2005. The side doors 2020 include a central orifice 2027 in the shape of a semicircle, for closing against the prosthesis, discussed below. The side doors include shelves 2021 on either side for riding against the channel 2018 of the loader body. The side doors each also include a retaining pin 2022. The pins protrude through side windows 2017 in the loader body and allow the side doors to slide within the loader body while preventing their complete removal from the assembly.

Top plate 2005 includes a top surface 2006, an adjustable internal iris 2011, which functions much like the iris in a camera. The iris has sections that adjust inward and outward to open and to close the central opening of the iris. The adjustable iris decreases the area of the opening and closes in a manner that allows the top section of the implantable device to rest on top of the partially or full closed iris. Opening and closing of the iris is controlled by control lever 2013. The top plate includes two vertical rods 2007 for mounting in the vertical bores 2015 of the loader body and also includes a vertical side guide 2008 with an elevating mechanism 2010 actuated by a top thumbwheel 2012. Raising and lowering via the elevating mechanism allows the user to raise and lower the iris and thus adjust the separation of the left and right flanges of the prosthesis with the iris.

The mounting and loading assembly is used in the following manner. The loader body is positioned conveniently for the user, with the top plate removed and with the doors open. A prosthesis, such as prosthesis 100, is placed on the loading platform, with the left atrium legs or flange facing downward and with the loading platform in the lower position. The doors 2020 are then closed, with the mounting platform still in the lower position, thus placing the left atrium flange below the doors. The mounting platform 2023 is then raised to its upper position by rotating pivot 2029, causing the lower portion (left atrium flange or legs) to be pressed against the under side of the doors 2020. While not shown in FIG. 31, this movement causes the legs of the left atrium flange to be radially spread out.

At this point, the top plate is assembled to the mounting and loading tool and a catheter, such as one of the catheters depicted above in FIGS. 10-12, and also described above, is introduced though the center of the prosthesis. The portion inserted includes the catheter tip and a portion of the catheter control wire connected to the tip. The position of the catheter is adjusted so that the right atrium ball ("RA ball") or other retention device is vertically aligned with the right atrium flange, as discussed above with respect to FIG. 11A. The iris is then partially closed. Vertical alignment may be achieved by raising the top plate 2005 using handwheel 2012. With the doors 2020 closed and the left atrium flange trapped below the doors, raising the top plate will stretch the prosthesis, separate the left and right atrium flanges, and also stretch the prosthesis over the catheter. In one embodiment, the diameter of the orifice made by the two half-circular cut outs 2027 of the side doors is about equal, or slightly less than, a diameter of the catheter intended for use as a delivery device for the prosthesis discussed herein. The diameter may range from about 3 mm (9 Fr) to about 7 mm (21 Fr).

As the iris is raised, the upper (right atrium) flange will approach the retention device, such as the RA ball and the outer sheath of the catheter. The iris may continue to be closed while the top plate is raised, thus bringing the RA flange into contact with the RA ball. If the mounting platform 2023 has not been fully raised, it may also be raised gradually during this process. The entire sequence may be achieved by sequential use of the mounting platform 2023 and pivot 2029, the iris 2011 and handle 2013, and the elevating mechanism 2010 and thumbwheel 2012. When the RA flange has closed over the RA ball, the outer sheath may then be brought over the RA flange, securing the end of the prosthesis in the outer sheath. At this point, the iris 2011 may be opened along with doors 2020 and the catheter and prosthesis removed from the mounting and loading tool. The inner wire, firmly attached to the catheter tip and RA ball, is then retracted, pulling the central portion of the prosthesis and the LA flange into the outer catheter.

The catheter is then processed as discussed above, including assembly to a control device or handle, packaging, and so forth. This process is desirably performed in a sterile environment, with all components, tools, fasteners, and so forth, scrupulously clean and sterile before and during all steps of the process. The mounting and loading tool depicted in FIG. 31 and described above is desirably made from an inert, lubricious and medically-acceptable plastic material, such as a fluoropolymer, fluorinated ethylene-propylene, PTFE, UHMWPE, acetal, polycarbonate, and so forth.

In addition to the mounting and loading tool discussed with respect to FIG. 31, there are other embodiments for mounting a prosthesis and for loading a prosthesis onto a catheter or delivery device. Additional embodiments of useful tools are discussed below. In the discussion below, FIGS. 32-34 concern a discrete mounting tool, while FIG. 35 concerns a separate tool for loading a mounted prosthesis onto a loading tool.

Figure 32:
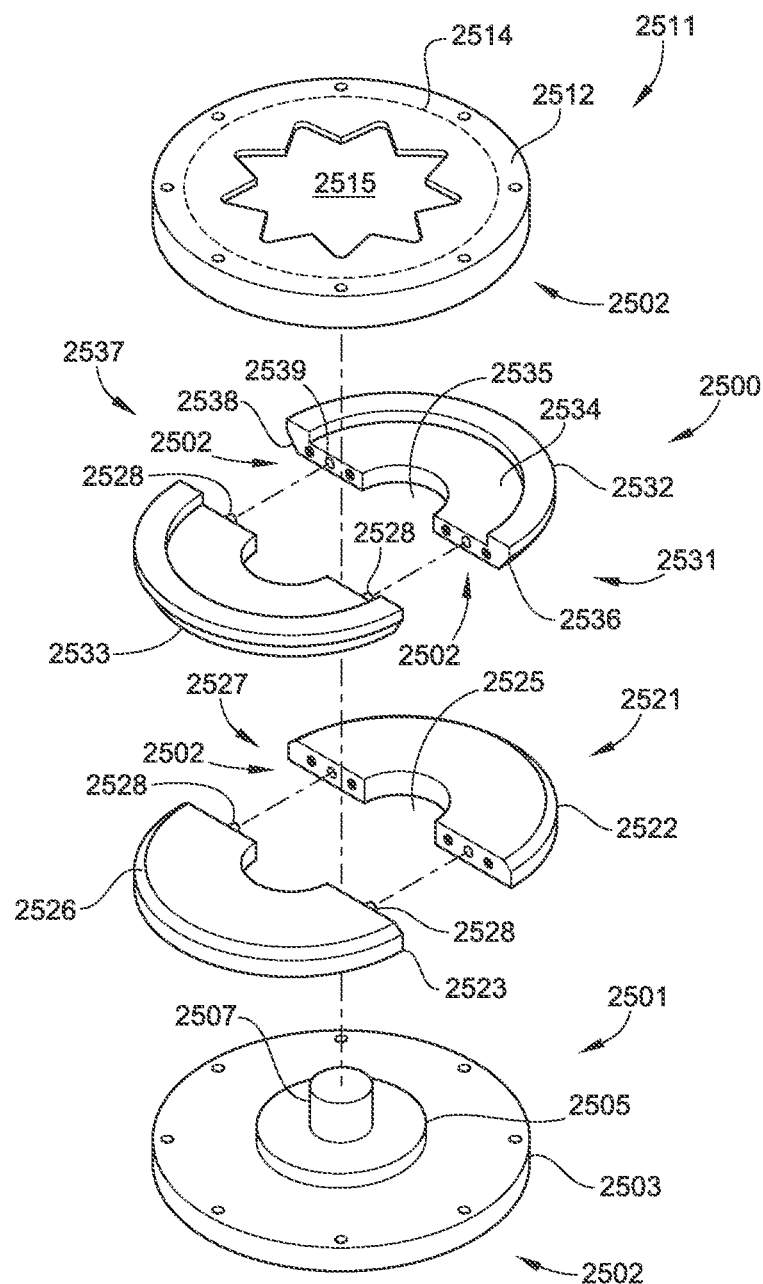
FIG. 32 depicts an exploded view of a second embodiment of a mounting tool for mounting a prosthesis.

FIG. 32 depicts a mounting tool 2500 useful for mounting a prosthesis for relieving intracardial pressure for a mammal, such as a human. The mounting tool includes four principal components. The principal components include a mounting plate 2501, a star-shaped cutout plate 2511, a lower flat disc 2521, also known as a right atrium or RA disc, and an upper counterbored disc 2531, also known as a left atrium or LA disc. The four components are used and stacked in the manner depicted in the drawing, in combination with a prosthesis mounted on the tool. All four components are desirably made from a lubricious, non-allergenic, medically-acceptable plastic, such as a fluoropolymer, fluorinated ethylene-propylene, PTFE, UHMWPE, acetal, polycarbonate, and so forth.

Mounting tool 2500 includes mounting plate 2501 having a cylindrical bottom disc 2503, the disc having a central raised portion 2505 and an additional raised portion 2507 atop the central raised portion. Plate 2501 also includes a plurality of inserts 2502 for attracting and joining with a similar number of inserts in cutout plate 2511. The inserts may be magnets or a combination of magnets and magnetically-attractive materials.

Star-shaped cutout plate 2511 includes a flat top surface 2512 with a cutout in a general shape of a star 2515. While the cutout has the general shape of a star, it is understood that the shape need not be a perfect star with perfectly equal sides and perfect angles between all legs or sides of the star. For example, the tips and corners of each point of the star are rounded rather than sharp. This avoids scratching the prosthesis and also avoids any scratching of personnel assembling the prosthesis to a catheter. A cutout in a general shape of a star is sufficient to accomplish the task described herein. The skilled artisan will appreciate that the shape would be appropriate for accommodating the shape of the device.

The bottom surface includes a counterbore 2514 for most of the entire bottom surface. A counterbored surface typically has an abrupt or right-angle termination, such as achieved by molding or by machining with an end-mill or other flat-bottomed tool. The counterbored surface is preferable to a more gradual change, such as a funnel-shaped countersink or angled approach. As discussed below, the counterbored surface of the cutout plate is used to mount the cutout plate to a loading tool. Thus, having the walls of the counterbore straight rather than angled is helpful, because with sufficiently close tolerances, the counterbore aids in firmly securing the cutout plate to the loading tool used. It is possible, however, that angled walls, i.e., a countersink, may be used instead. Cutout plate 2511 also includes a plurality of inserts 2502 matching the plurality of inserts in mounting plate 2501. In one embodiment, the inserts are polar magnets, i.e., N-S magnets with the poles arranged so that the discs can only be joined in one way.

For example, mounting plate 2501 may have eight N-S magnets molded into the plate with the north poles on the top side, with the raised portions. If cutout plate 2511 has the magnets similarly mounted, north poles on top, south poles on bottom, then the south poles on the bottom of cutout plate 2511 will attract the north poles on the top side of mounting plate 2501, and the two plates may be joined. Because of the polar orientation, there will be no magnetic attraction if one tries to assemble the discs in the incorrect manner, i.e., with the counterbored surface on top. In another incorrect orientation, with the cutout plate 2511 below mounting plate 2501, the plates will be magnetically attracted for assembly, but the star-shaped feature 2515 will be positioned away from the raised portions 2505, 2507. A user will not be able to position the prosthesis on the mounting tool using both the raised surfaces and the star-shaped cutout. Thus the mounting plate 2501 and the cutout plate 2511 have been designed for assembly and for fool-proof assembly.

Right atrium disc or lower flat disc 2521 is made as a two-part assembly, a right half 2522 and a left half 2523. There is a central orifice 2525 and the disc has a chamfer or bevel 2526 on its side. Each side of each half has three bores 2527 within the disc and perpendicular to a radius of the disc, the three bores on each side used to assemble the halves. In one embodiment, the outer two bores are used for magnets to attract the halves together and the central bore is used for a dowel to align the halves. Thus, in one embodiment, right half 2522 has three bores 2527 as shown, the central bore being merely a void for accepting a dowel from the left half, and the two side bores filled with two north-south magnets with the south poles facing outward. Left half 2523 has three bores 2527 on each side, the central bore on each side filled with a protruding dowel 2528 and the two side bores filled with two north-south magnets with the north poles facing outward. Use of the dowel and the void may be considered as a male-female joint. When the two halves are brought into contact, the opposite poles of the magnets will attract and the two halves will be firmly joined.

The left atrium disc 2531, also known as the upper counterbored disc, is also formed as two halves, right half 2532 and left half 2533. Counterbored disc 2531 has a counterbore 2534 on top, the counterbored or void portion removing material from a majority of the top surface. There is a chamfer or bevel 2536 on the side of the disc toward the bottom, such that when counterbored disc 2531 is assembled with lower flat disc 2521, there is a "V" in profile, the "V" formed by the bevels or chamfers on the two discs. Counterbored top disc 2531 also has a central bore 2535 of about the same diameter as central bore 2525 of lower flat disc 2521. Each side of the halves includes three bores 2537 within the disc, the bores perpendicular to a radius of the disc. The bores are voids for accepting devices for joining the two halves, as discussed above for the lower flat disc. In one embodiment, the central bores include a dowel and a void for aligning the two halves, while the outer bores include magnets 2502 with oppositely-facing poles for attracting each other. The dowel and void function for assembly as a tab and a slot in both the right and left atrium discs 2521, 2531. The bores may themselves be considered a slot, for use with a dowel, a tab, a magnet or a magnetic material. The tabs may be made of a plastic material or may be made of durable stainless steel or other non-corroding, medically-acceptable material.

In other embodiments for the side bores on either the lower plate 2521 or the upper counterbored disc 2531, the inserts could include magnets on one half and steel or iron bars on the other half, or one magnet and one steel bar on each half, with a facing magnetically-attractive metal and magnet on the other half.

In one embodiment, the lower flat disc 2521 may be made a different height than the height of the upper counterbored disc 2531. The difference in heights makes it unlikely that an improper assembly could occur between one half of the lower flat disc and one half of the upper counterbored disc. In one embodiment, the magnets of the halves with the central dowels may be assembled with the north poles outward, while the magnets of the halves with the central voids may be assembled with the south poles outward. This would make mis-assembly of the lower flat disc 2521 and the upper counterbored disc 2531 very difficult, since two pieces with dowels (male portions) would be impossible to join. While the two pieces with voids may be magnetically attractive and may join to form a mis-assembly, there would only be one assembled disc, since the two halves with the dowels could not be joined. Thus, use of the magnets and dowels makes assembly of the discs virtually error-proof.

Mounting tool 2500 is used to orient a prosthesis for placement in a loading tool, as discussed below. In practice, a prosthesis for placement in a patient's heart is placed on the mounting plate 2501. In one embodiment, a right atrium (RA) flange is placed on the central portion 2505. The star-shaped cutout plate 2511 is placed atop the mounting plate 2501, with the points of the star placed atop the flange joints of the RA flange, thus locking the prosthesis in place with the oppositely-facing magnets. The left atrium (LA) flange and the barrel, or central portion of the prosthesis, now stand above the raised portions 2505, 2507 of mounting plate 2501. The right atrium disc 2521 is now joined to the assembly between the right atrium flange (lower portion) of the prosthesis and the left atrium flange (upper portion) by bringing the two halves together, such that the bevel 2526 is on the upper side of the disc 2521.

The left atrium disc 2531 is then added to the assembly atop the right atrium disc, also by bringing the two halves together. In this instance, bevel 2536 of the left atrium disc 2531 faces downward. The chamfers or bevels of the two discs are thus adjacent when the mounting tool 2500 is assembly correctly, the bevels together forming a "V" which will be used later by the loading tool, as discussed below. The mounting plate 2501 and the star-shaped cutout plate 2511 may then be removed. When the prosthesis has been placed correctly on the mounting tool and the mounting plate and cutout plate are removed, the left atrium flange protrudes from the left atrium disc and the right atrium flange protrudes from the right atrium disc, as seen in FIGS. 33-34.

Figure 33:
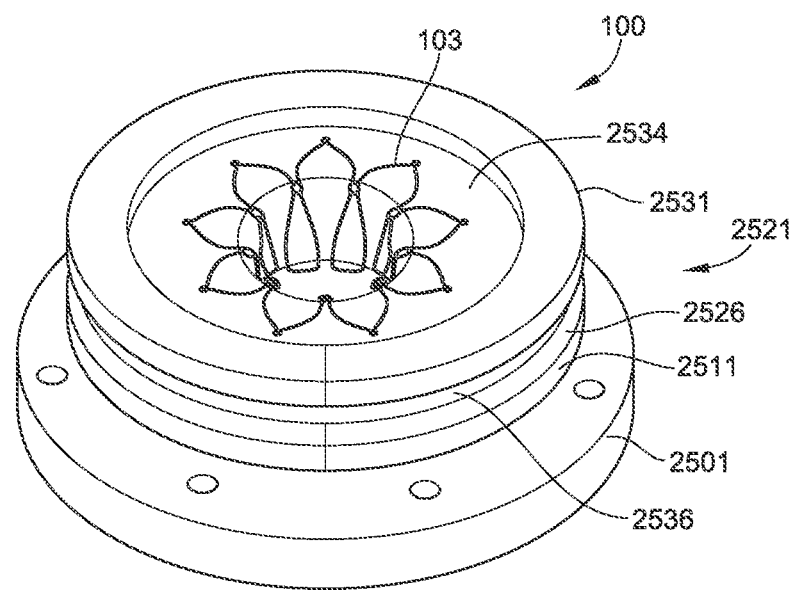
FIGS. 33 and 34 depict the mounting tool with a prosthesis mounted.

The mounting tool is depicted in FIG. 33 after it has been assembled with a prosthesis 100. The mounting tool includes mounting plate 2501 with cutout plate 2511 atop the mounting plate, and with left atrium disc 2531 atop right atrium disc 2521. In this figure, prosthesis 100 is mounted with left atrium flange 103 visible on top. Note the counter bore 2534 visible in the left atrium disc 2531. This is the configuration immediately after the prosthesis has been mounted and the left and right atrium discs have been inserted to separate the left and right atrium flanges. Note also that bevels 2526 and 2536 are adjacent, forming a V when seen from the side.

Figure 34:
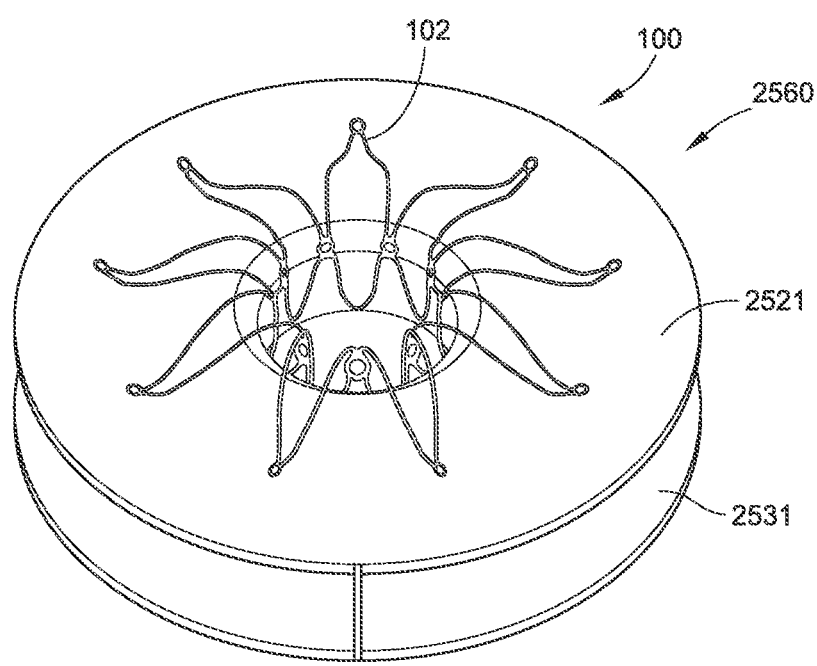

In FIG. 34, the mounting and cutout plates have been removed and the assembly 2560 has been inverted, with right atrium disc 2521 atop left atrium disc 2531 and with the right atrium flange 102 of the prosthesis 100 on top. Note that the right atrium disc 2521 is flat and has no counterbore on the side seen in this view.

Loading the Prosthesis into a Loading Tool

Figure 35:
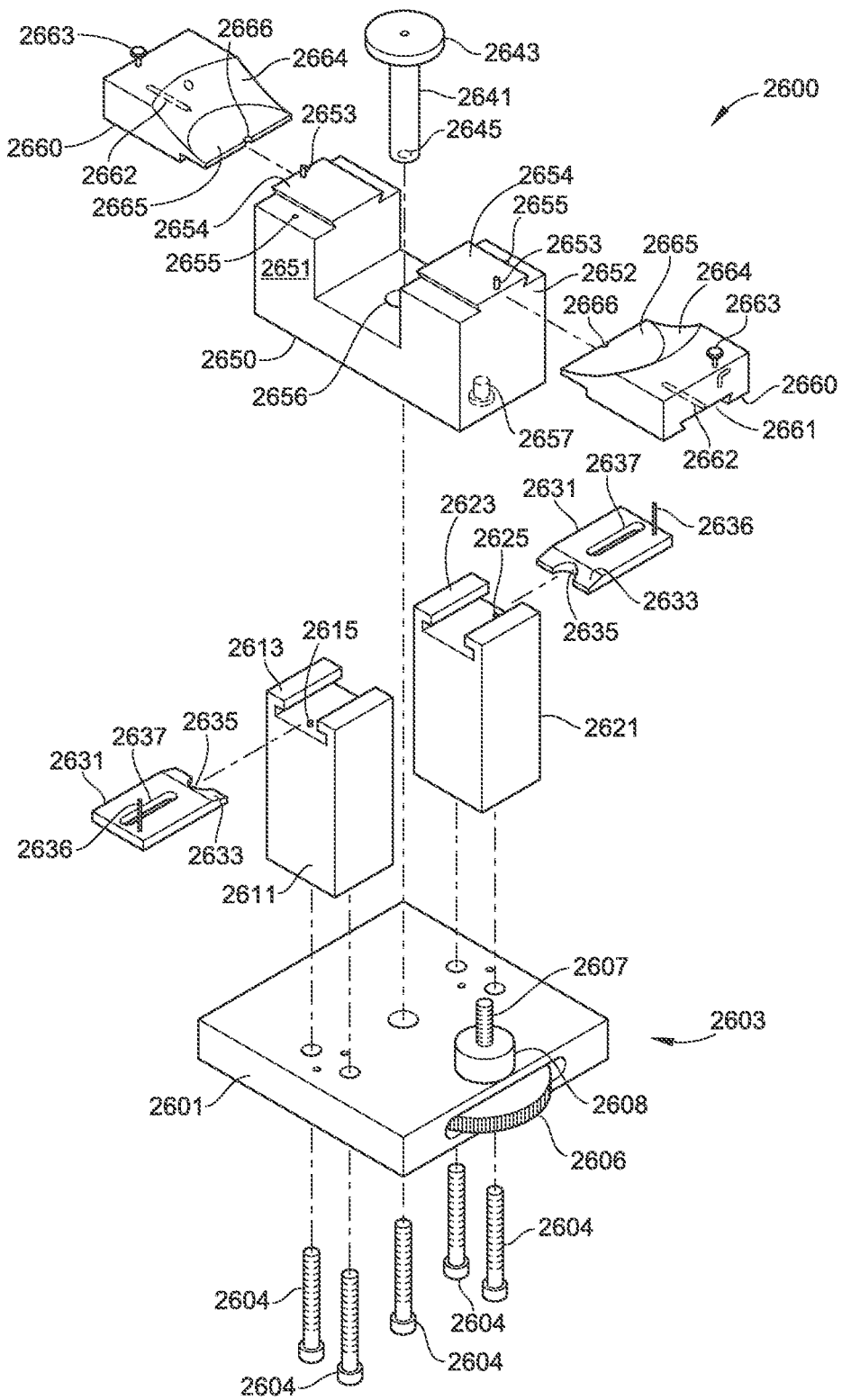
FIG. 35 depicts an exploded view of a loading tool for loading a prosthesis on a mounting tool onto a delivery device.

After the prosthesis has been mounted, a loading tool may be used to assemble the prosthesis and place it into a catheter or other delivery device. A loading tool useful in this process is depicted in FIG. 35 and is herein described.

Loading tool 2600 includes a base plate 2601, side door supports 2611 and 2621, a central column 2641 and a travel subassembly 2650. The base plate, side door supports and central column each mount to the base plate via fasteners 2604, as shown. In one embodiment, the fasteners may mount through the bottom and the heads may reside in countersunk or counterbored recesses in the bottom of the base plate. The base plate also includes a travel control mechanism or thumbwheel 2606, including travel screw 2607 and spacer 2608. In this embodiment, the travel control mechanism 2606, and the thumbwheel travel adjuster are mounted within the base plate, and a portion of the handwheel protrudes through a side of the base plate. Rotating the thumbwheel allows one to advance or retract travel screw 2607 and thus raise or lower travel subassembly 2650.

Side doors 2631 are identical and reside on side door supports 2611, 2621. Main doors 2660 are also substantially identical and reside on travel subassembly 2650. In one embodiment, door supports 2611, 2621 each include a top shelf 2613 for capturing a side door and allowing it to ride back forth, to and fro. In addition, door supports 2611, 2621 also each contain a travel stop or pin 2615, 2625. The pin stands in a groove 2637 within the side door, the pin limiting travel of the door to that allowed by the grooves, e.g., the half-way mark of the central column 2641 and its concentric top surface 2643, on the one side, and retreat from the central column in the opposite direction when appropriate. In this manner, the side doors can slide back and forth symmetrically to meet each other. The side doors have a taper 2633 on their front, as well as a half-circular cutout 2635 on the front. Each side door 2631 also has a vertical pin 2636 for ease of moving the door back and forth and also limiting the forward travel, when the pin touches the shelf 2613. In one embodiment, the diameter of the orifice made by the two half-circular cut outs is about equal, or slightly less than, a diameter of a catheter intended for use as a delivery device for the prosthesis discussed herein. The diameter may range from about 3 mm (9 Fr) to about 20 mm (60 Fr).

Main doors 2660 mount atop the travel subassembly 2650 via main door mounts 2651, 2652. The main doors slide back and forth in a manner orthogonal to the side doors. In this embodiment, the main doors are somewhat larger than the side doors and are used to compress the prosthesis to a diameter suitable for a catheter with a similarly desirably small diameter for delivery to a patient. The front portion of the each of the main doors thus includes a transition 2664 to a frontal semicircular arc 2665 and a semicircular bore 2666 with a radius consistent with such a small diameter. In one embodiment, the desired diameter is about 3.3 mm or 10 Fr, and the radius of the front bore is thus about 1.65 mm. In other embodiments, the radius is from about 1 mm to about 4.5 mm, to accommodate delivery catheters from about 2 mm to about 9 mm, and for catheters with a similar diameter.

The travel subassembly 2650 mounts to the loading tool via an internal threaded bore 2657 that interfaces with threaded screw 2607. Movement of the thumbwheel 2606 moves travel subassembly 2650 up and down as desired. Travel assembly 2650 includes door mounts 2651, 2652 including tongues 2654 atop the mounts and pins 2653 for limiting travel of the main doors. The main doors 2660 are substantially identical and include a groove 2661 along their length of their bottom. Tongues 2653 ride within grooves 2661 of the main doors.

The main doors also include locking pins 2663. Each pin may be used to lock the main door 2660 into the closed position by closing the door fully and depressing the pin to engage orifice 2655 in door mounts 2651, 2652. The pins 2663 may also be used to restrain each door away from the closed position by opening the main doors and depressing the pins outside travel subassembly 2650 so that further inward travel is not possible with the pins depressed. Central column 2641 with mounting surface 2643 mounts to the base plate 2601 via a central orifice 2645 and a fastener from below the base plate. The central column is positioned symmetrically within orifice 2656 of the travel subassembly 2650. The central column and the mounting surface are stationary, while around them the travel subassembly 2650 travels vertically and side doors 2631 and main doors 2660 move horizontally.

Loading the Prosthesis into the Catheter

The loading tool is used in the following manner, in one embodiment. Other embodiments and other methods may also be used.

The side doors and main doors are opened to their full open positions and the mounted prosthesis assembly 2560 described above is placed onto central column top surface 2643, with the right atrium flange or legs up and the left atrium flange down. Note that in this configuration, the left atrium disc 2531, which is the disc with the large counterbore 2534, faces downward. In one embodiment, the counterbore is sized and oriented to fit precisely onto top mounting surface 2643 of the loading tool 2600, discussed below. Top surface 2643 is the mounting or loading surface for placing the mounted assembly 2560 into the loading tool 2600.

Once the mounted assembly 2560 is placed into the loading tool 2600, the travel subassembly 2650 is raised or lowered so that the side doors align with the "V" formed by the bevels or "V" of the mounted assembly. The side doors 2631 are then closed, bringing the tapered front portions of the side doors into contact with the "V" and urging apart the left atrium and right atrium discs of the mounting tool. The main doors 2660 are then closed against the side doors 2631.

Figure 36:
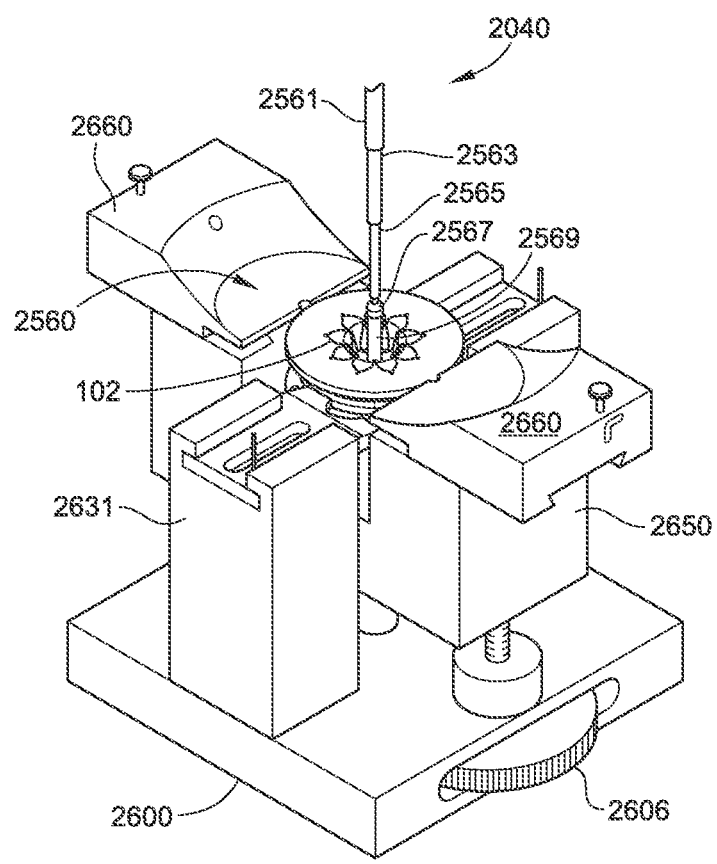
FIG. 36 depicts the prosthesis being loaded into a catheter.

Once this has been accomplished, a delivery catheter 2040 is assembled to the prosthesis, as depicted in FIG. 36. A clear loading tube 2561 is moved over the outer sheath 2563 and the tip (not shown in FIG. 36) of the catheter 2040 is inserted through the central bore of the mounted assembly 2560. Visible in FIG. 36 is the inner sheath 2565, inner control wire 2569 and right atrium ball 2567. As seen in the figure, the right atrium ball 2567 should be aligned with the right atrium flange 102. The thumbwheel 2606 is then adjusted so that the main doors 2660 are above the side doors 2631, such that the main doors 2660 can close. As the closed main doors are raised using thumbwheel 2606, the right atrium disc 2521 will rise, and the right atrium flange 102 will begin to lengthen axially and compress radially. It may be advantageous to insure that no legs or struts of the flange are intermingled or caught in the disc or the doors as the doors rise. Thumbwheel 2606 is used to raise the main doors while the catheter is held in a position that allows the right atrium flange to close around the right atrium ball 2567. When this operation has been correctly accomplished, the legs or struts of the flange are evenly and tightly spaced around the right atrium ball or flange.

The prosthesis is now brought into the catheter. In one embodiment, the following procedure is used. The RA ball acts as a compression device, compressing the right atrium flange. After the right atrium flange is firmly compressed around the right atrium ball, the outer sheath 2563 is held firmly while the inner sheath 2565 and control wire 2569 are pulled back. This pushes outer sheath 2563 over the right atrium flange and ball 2567. The ball 2567 should be pulled into the outer sheath 2563 so that it, and the right atrium flange, are no longer visible. The travel assembly 2650 is now lowered, using the thumbwheel, until it just touches the side doors 2631 (not shown in this view). Both sets of doors are opened and the catheter 2040 and left and right atrium discs 2631, 2621 are removed from the loading tool 2600. The left and right atrium discs are then removed from the catheter by pulling them apart.

The left atrium flange is now lengthened axially and compressed radially. In one embodiment, the clear loading tube 2561 has a larger diameter than the outer sheath 2563. The clear loading tube 2561 is slid over the left atrium flange 103, pushing the left atrium flange legs together. The clear loading tube should be slid forward or distally until it completely covers the prosthesis. The control wire 2569 is then pulled proximally, pulling the inner sheath 2565 and pulling the prosthesis into outer sheath 2563. The clear loading tube 2561 is then removed. The above mounting and loading procedures are accomplished in a sterile environment. Alternatively, the devices and components may be sterilized or re-sterilized after assembly.

Figure 37:
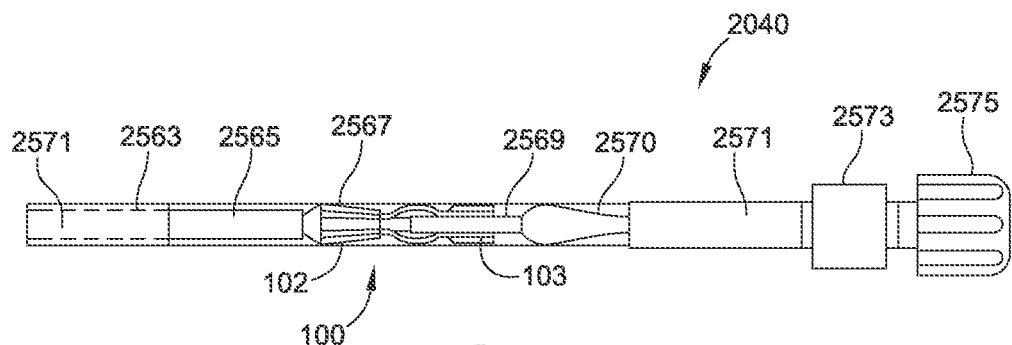
FIG. 37 depicts the loaded catheter with protective packaging.

Any other desired components, such as an outer shipping sheath, may then be added. In one embodiment, an outer shipping sheath is added in a sterile manner, as shown in FIG. 37, over the outer sheath 2563. Sterile outer shipping sheath 2571 with connector 2573 and visible cap 2575 is added over the outer sheath 2563 in such a way that inner sheath 2565, right atrium ball 2567 and right atrium flange 102, the central portion of prosthesis 100, left atrium flange 103, inner control wire 2569 and tip 2570 are visible from the outside of sheath 2571. In the embodiment shown, the prosthesis, including the right atrium flange 102 and right atrium ball 2567, has been advanced using the control wire 2569, or the outer sheath 2563 has been retracted, to allow visibility from the outside of the device. The catheter 2040, with the prosthesis loaded and ready for inspection and deployment, is now ready for shipment to a hospital or other care-giving institution.

Implanting and Deploying the Prosthesis

With this embodiment, and in this configuration, a physician can immediately inspect the prosthesis and determine whether the prosthesis is suitable for implantation into a patient. For example, the physician can immediately inspect, without even opening the outer package, whether the legs or struts of the right atrium flange are intertangled. The physician can also determine whether the left atrium flange or center portion are also suitable for implantation into the patient.

As noted, the shipping sheath is advanced over the outer sheath 2653 of the delivery of deployment catheter 2040. Accordingly, the prosthesis 100 remains within the outer sheath at all times during shipping and during removal of the shipping sheath. In some embodiments, the outer catheter is connected at its proximal end to an irrigation system, described below, suitable for irrigating the outer sheath, and thus the prosthesis, with sterile fluid, a radiopaque dye, or other desired solution. A physician can thus remove the shipping sheath, flush the prosthesis with sterile solution using the irrigation system, and move the prosthesis back and forth within the outer sheath. This allows the physician to remove any possible bubbles from the device and the catheter, at the same time allowing the physician to test the level of effort required to advance and retract the prosthesis or the outer sheath with respect to each other.

Control Systems for Deploying the Prosthesis

Figure 38A:
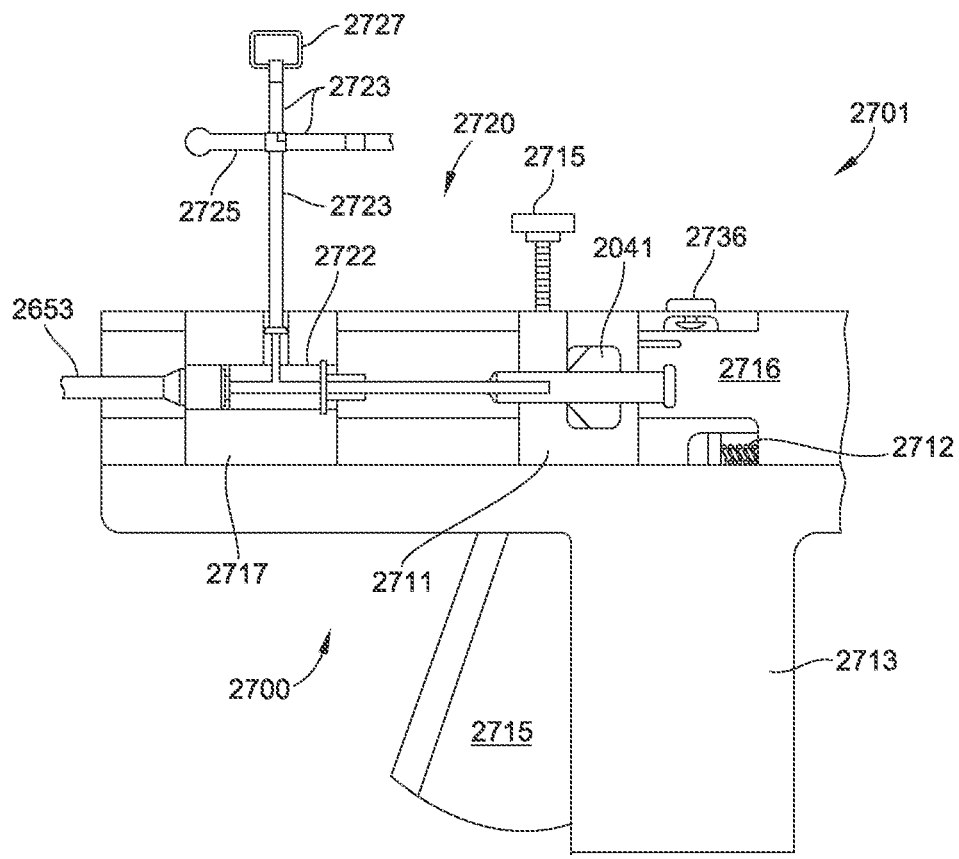
FIGS. 38A and 38B depict an additional embodiment of a control device or handle for deploying the prosthesis.
Figure 38B:
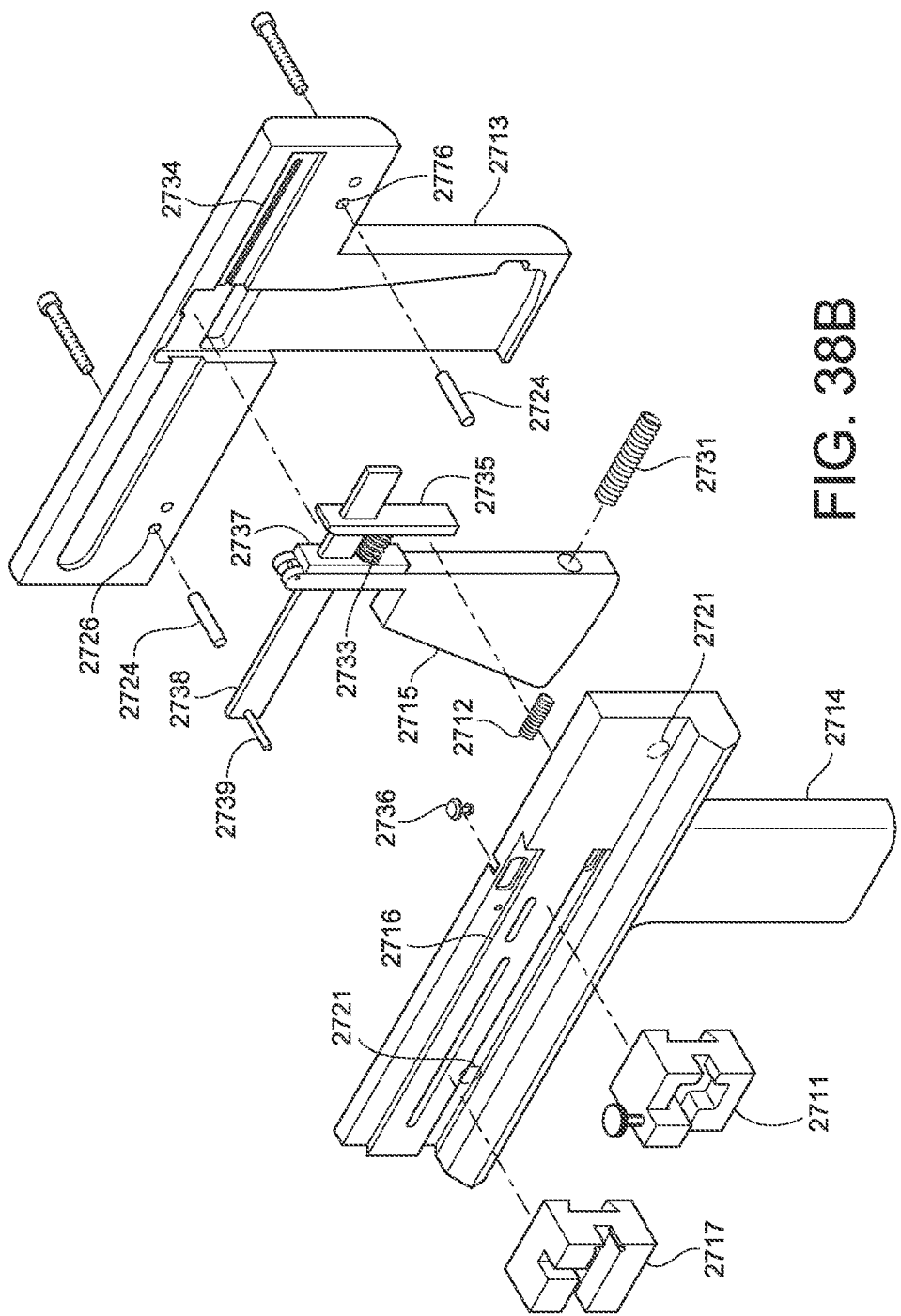

A control system, including a control device or handle, and an irrigation system, may also be usefully employed with the catheter described above. One example of a control system or handle was given above in FIG. 12, and also explained. Another example is depicted in FIGS. 38A and 38B, control system 2700, including control handle 2701 and irrigation system 2720. The control handle 2701 includes a housing or grip 2713 and a control trigger 2715 for a user to retract the outer sheath or advance the inner control wire. The tension or pull required for the trigger 2715 is set with trigger spring 2731. Thus, spring 2731 controls the force needed by the user to deploy the prosthesis, i.e., the force required to release the implant onto the septal wall.

The inner control wire is grounded to the control handle through first plate 2711 via the flange 2041 of the inner control wire and may also be secured with adjustment screw 2715. The position of the first plate within the handle is set by a pin and bore, or set screw or other arrangement (not shown). The second plate 2717 is connected to the outer sheath and the irrigation system, which are secured to the second plate via connector 2722. The second plate is connected via a slot (not shown) on its rear face to a pin (see FIG. 38B) on the actuation mechanism within the handle. The first and second plates 2711, 2717 have slots or mortises on their rear faces for riding on a tenon or shelf 2716 on the side of the front grip cover 2714.

FIG. 38B depicts the internals of the trigger mechanism. Grip 2713 also includes a front cover 2714. The front cover 2714 is assembled to the grip 2713 through fasteners 2724 and orifices 2726 in the grip 2713 and mating parts 2721 in the cover 2714. The mating parts may be molded-in nuts, threaded surfaces, or other appropriate joining components.

The internals of the trigger mechanism are largely contained within the grip 2713. These include a trigger spring 2731, grounded between the trigger 2715 and a pocket in grip 1713. As noted, spring 2731 determines the pull required to activate the trigger. This spring also provides a return for the trigger to its resting or neutral position after each pull by the user. Mounted within a channel 2734 in grip 2713 are a vertical braking/release bar 2735, vertical driving bar 2737 and a driven horizontal bar 2738. Trigger 2715 also has an internal rectangular bore (not shown) for accommodating driven horizontal bar 2738.

Driven bar 2738 in one embodiment has a rectangular cross section, while the driving and braking/release bars 2735, 2737 have bores with rectangular cross sections and are mounted around the driven bar via the rectangular bores. Bar 2738 has a square cross section in one embodiment, as do the matching bores in the braking and driving bars. Other configurations may also be used for the bars 2735, 2737 and 2738, and the corresponding bores. Driven bar 2738 includes a pin 2739, which is connected directly to a bore (not shown) on the rear of the second plate 2717. Biasing spring 2733 is grounded between the driving bar 2737 and braking/release bar 2735, which is somewhat longer than driving bar 2737. Biasing spring 2733 maintains compression and separation between the braking and advancing bars. Trigger 2715 is also mounted around the driven bar 2738 via a rectangular bore in this embodiment. Other embodiments may include different geometries for driven bar 2738 and the corresponding bores in the trigger, the driving bar and the release/braking bar. These shapes may include rounded rectangular, ovate and others.

Compression spring 2712 biases the braking/release bar 2735 to a braking position by maintaining contact between the braking/release bar 2735 and driven bar 2738. Release pin 2736 protrudes above the top of the grip 2713 and is used by the operator to release the driven bar from the braking and driving bars. When a user wishes to return the second plate 2717 to a forward position, or to select a position for the second plate, the user simply presses on pin 2736. Pressing on pin 2736 has the effect of pushing the release/braking bar 2735 to the rear by overcoming the compression of spring 2712. Releasing the braking bar 2735 enables easy manual movement of the driven bar 2738 and thus second plate 2717 and the outer sheath of the catheter.

The trigger mechanism works in this manner, although many other embodiments are also possible, as also discussed in U.S. Pat. No. 7,699,297. When the user activates the control mechanism by pulling the trigger, the driven bar 2738 moves to the rear, to the right in FIGS. 38A and 38B, as does the connected second plate 2717. The outer sheath is also connected to the second plate, and as the second plate moves to the right or rear, the outer sheath does also, thus pulling the outer sheath in a proximal direction and exposing more of the prosthesis and the inner control wire. The distance traveled by the activating bar is determined by outer dimensions of the driven bar, the height of the bore in driving bar 2737, the distance between the driving bar 2737 and the braking/release bar 2535, and length of the vertical distance in the bore of trigger 2715. These lengths or distances determine the angles between the various components and thus limit the distance that is traveled by the trigger, the driving bar and the driven bar, on each pull of the trigger. Thus, each pull of the trigger moves the driven bar 2738, the second plate 2717 and the outer sheath of the catheter 2653 a predetermined distance. This makes it straight-forward for the medical professional to deploy the prosthesis. Each pull of the trigger will retract the outer sheath or advance the control wire a known and repeatable distance.

Returning to FIG. 38A, the outer sheath 2653 is grounded to the second plate 2717 via connector 2722, which provides both a mechanical connection to the control device through second plate 2717 and also a fluid connection to irrigation system 2720. The connector 2722 connects to the irrigation system 2720 through tubing 2723 to a three-way valve 2725. The valve may also include other tubing connections 2723 or to one or more connectors (not shown), and one or more optional caps 2727. As noted above, the irrigation system may be used by the physician to flush the prosthesis and outer sheath with sterile fluid before use, and to check for and remove any bubbles in the catheter and in the prosthesis. Such fluid will exit at the far end of the outer sheath 2653 after connector 2573 and cap 2575 are removed.

In one embodiment, the control system 2700 includes an internal mechanism that determines the amount of movement of the first or second plate when the trigger is pulled, and thus when the outer sheath is retracted or in the control wire and prosthesis is advanced. As noted, the amount of force needed for a single trigger actuation may be set by spring 2731. The remaining internal mechanisms, as discussed above, sets the distance traveled. The catheter is advanced to a point where the catheter and the prosthesis are in the desired location within the patient, as determined by the radiopaque methods described above, or by other desirable, reliable method.

The tip of the catheter is advanced through a surgically-created opening in the atrial septum. The tip is thus in the left atrium at the start of the deployment process. When the trigger is pulled, the outer sheath is retracted a distance sufficient to remove the outer sheath from around the left atrium legs and flange. In embodiments, this distance is about 7 mm. At this point, the left atrium legs are deployed inside of the left atrium, similar to FIG. 27, step 6000, which shows the left flange legs deployed from the outer sheath of catheter 111 into the left atrium. The entire catheter system is then pulled back such that the left atrium legs contact the septal wall, as seen in FIG. 27, step 6010. At this point, the central portion of the interatrial vent and the right atrium legs and flange are still retained by the outer sheath. The central portion, still retained, is located in the septal opening. The right atrium legs, still retained, are located in the right atrium. A second pull of the trigger retracts the outer sheath a distance, about 7 mm, to remove the outer sheath from around the central portion and the right atrium legs, thus deploying the central portion and also deploying the right atrium legs in the right atrium.

While 7 mm is a central value, the actual value may vary from about 3 mm to about 11 mm. In other embodiments, other travel ranges may be used. It will also be understood that this distance may vary, due to tolerance stack ups of the several components, including those of the catheter and the control device.

At this point, the prosthesis has been deployed, and the physician will normally inspect the deployment by one or more of the non-invasive techniques described above to insure correct placement. If deployment is satisfactory, the physician may remove the catheter and all components, including the tip, the outer sheath, the control wire, and so forth, and finally the guide wire used.

During implantation, the physician may use the catheter fluid system to determine the precise placement of the end of the outer sheath and thus the prosthesis. After the device has been advanced through the patient to a point near to the desired implantation point, the radiopaque markers on the left or right atrium flanges or the catheter may be used, along with fluoroscopy, echosound or other non-invasive means, to determine the location of the device within the patient. In addition to, or instead of the radiopaque markers, the irrigation system may use a radiopaque solution, such as a barium solution or other radiopaque solution.

The control device or handle of FIGS. 38A and 38B is merely one example of a delivery or deployment device and control device, as discussed herein, for use with a delivery catheter. Other control devices may also be used, such as additional examples depicted in FIGS. 39A, 39B and 40.

Figure 39A:
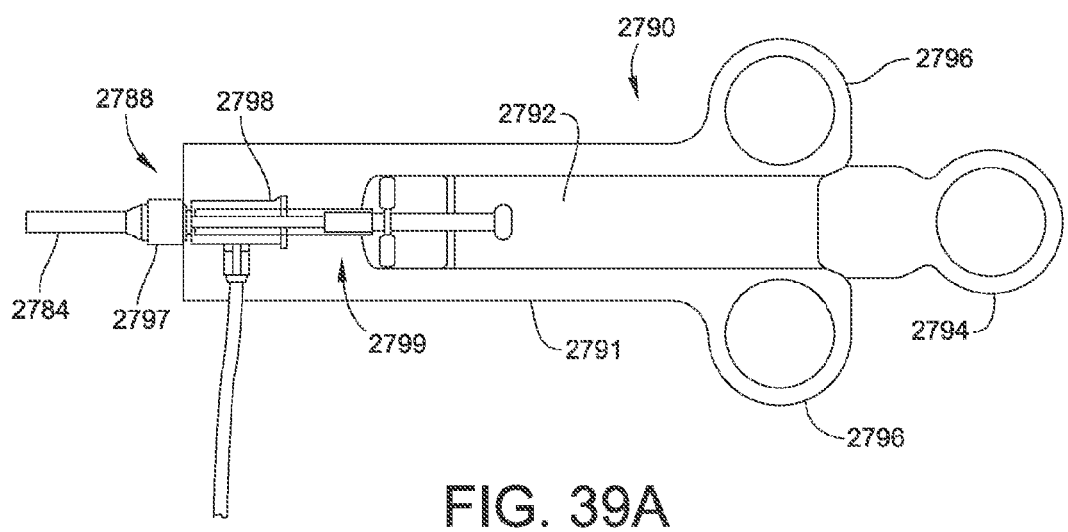
FIGS. 39A and 39B depict another embodiment of a control device for deploying the prosthesis.
Figure 39B:
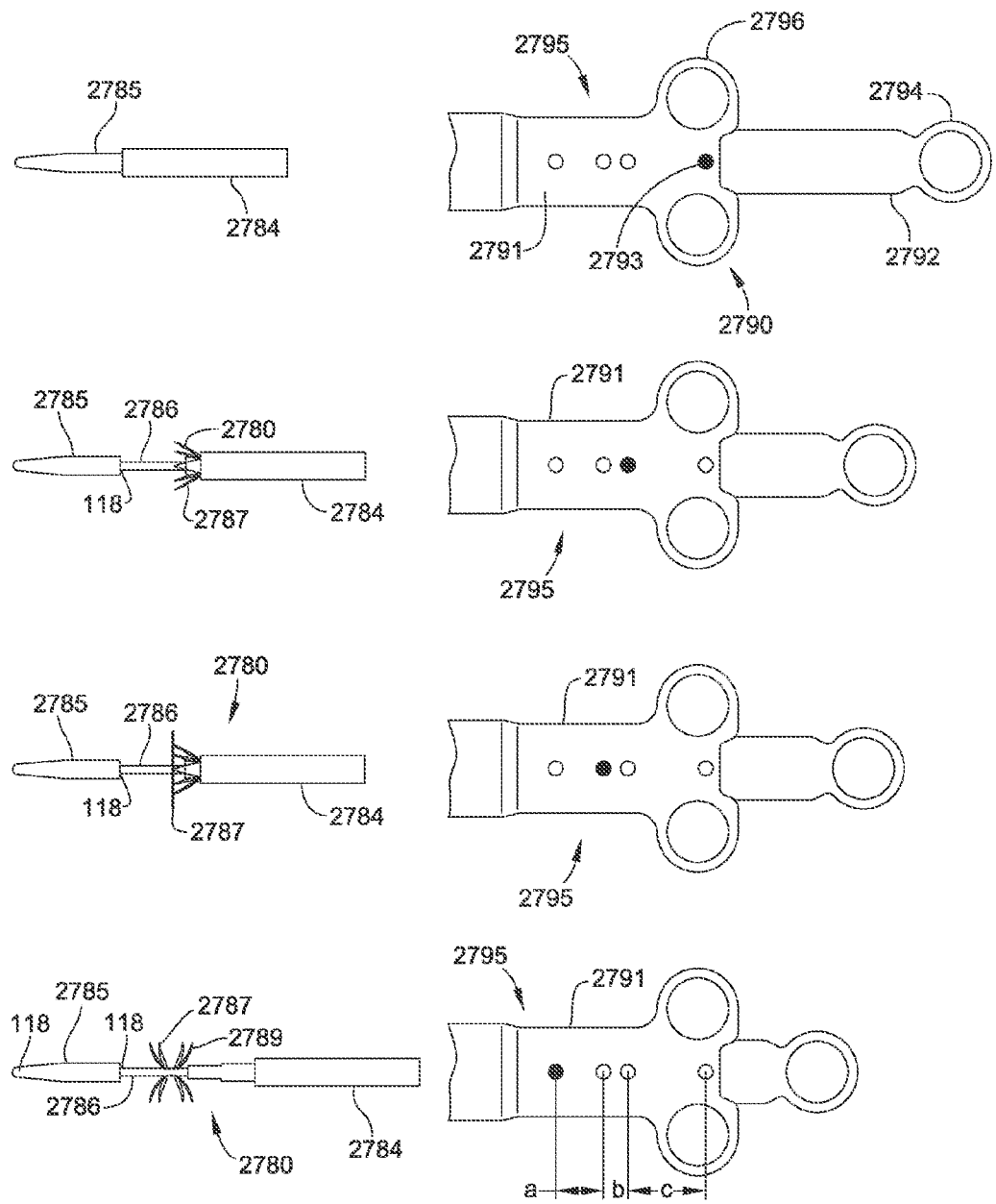

Another embodiment of a control device is depicted in FIGS. 39A and 39B. In this embodiment, as seen in FIG. 39A, control device 2790 connects to delivery catheter 2788 for delivering a prosthesis. Control device 2790 includes a control body 2791 and a control handle 2792. The control body 2791 is attached or connected to the outer sheath 2784 via connector 2797. The moveable control handle 2792 is attached or connected to an inner control wire 2786 (not visible in FIG. 39A) via connector 2799, and as seen in FIG. 39B, connected to the deployable prosthesis 2780. Connector 2798 is a fluid connector for supplying fluid to the inside of catheter 2788 and the inside of outer sheath 2784. The fluid may be sterile fluid, or may be a sterile radiopaque fluid. Control handle 2792 is equipped with a thumb ring 2794, while the control body 2791 includes two finger rings 2796. Handle 2792 is also equipped with a protruding bump or tab 2793, which is sized and designed for sequential positioning in orifices 2795.

In the sequence depicted in FIG. 39B, control body 2791 remains stationary, as does outer sheath 2784, while the control handle 2792 moves progressively to the left, i.e., in a distal direction, in a series of discrete steps, as shown. As the tab 2793 moves to the left, from the first of the orifices 2795, on the right to the last orifice on the left, the tab is visible in one orifice after another, as shown. At the same time, distal tip 2785 also moves progressively to the left, distally, to sequentially deploy more and more of prosthesis 2780. In the middle two views, left atrium flange 2787 is first partially deployed and then fully deployed. In the final view, both left and right atrium flanges 2787, 2789 are deployed. The final view also allows a close-up of the delivery catheter details, including tip 2785 and non-invasive imaging markers 118 on the tip 2785, just proximal to the tip, and just distal of the deployed prosthesis 2780.

In this handle, the control handle 2792 advances control wire 2786 and thus the prosthesis 2780 in a sequenced manner that is controlled by the spacing a, b, c, between the orifices 2795 of the control body 2791. In one embodiment, the distances are 16 mm, 5 mm and 11 mm, respectively. Other embodiments may use other discrete distances. These distances help the medical professional who deploys the prosthesis to more accurately position the prosthesis within the patient. The device and sequence shown in FIGS. 39A-39B uses a stationary outer sheath and a moving inner control wire and prosthesis. It is understood that the handle 2792 could alternately be attached to the outer sheath, so that the tab 2793 begins in the most distal position, as shown in the last movement of the sequence, and then the handle and tab move proximally to retract the outer sheath, thus deploying the prosthesis.

In addition, of course, non-invasive imaging is used to position the catheter outer sheath 2784 and distal tip 2785 to a desired position within the patient, i.e., with the distal top 2785 through an opening in the atrial septum of the patient. Differences between patients may also be studied, and the position of the control handle 2792 may be adjusted slightly for optimal prosthesis placement. As noted in other embodiments, markers for x-ray or echogenic imaging may be placed on the prosthesis, on the delivery device, or both, to assist in accurate placement. Using these markers, the medical professional or surgeon implanting the device may make adjustments to the position of the outer sheath, the prosthesis and the relative distances between them. The prosthesis may then be deployed as desired and the implanting catheter, with its tip, inner control wire, and so forth, retracted from the patient.

Figure 40:
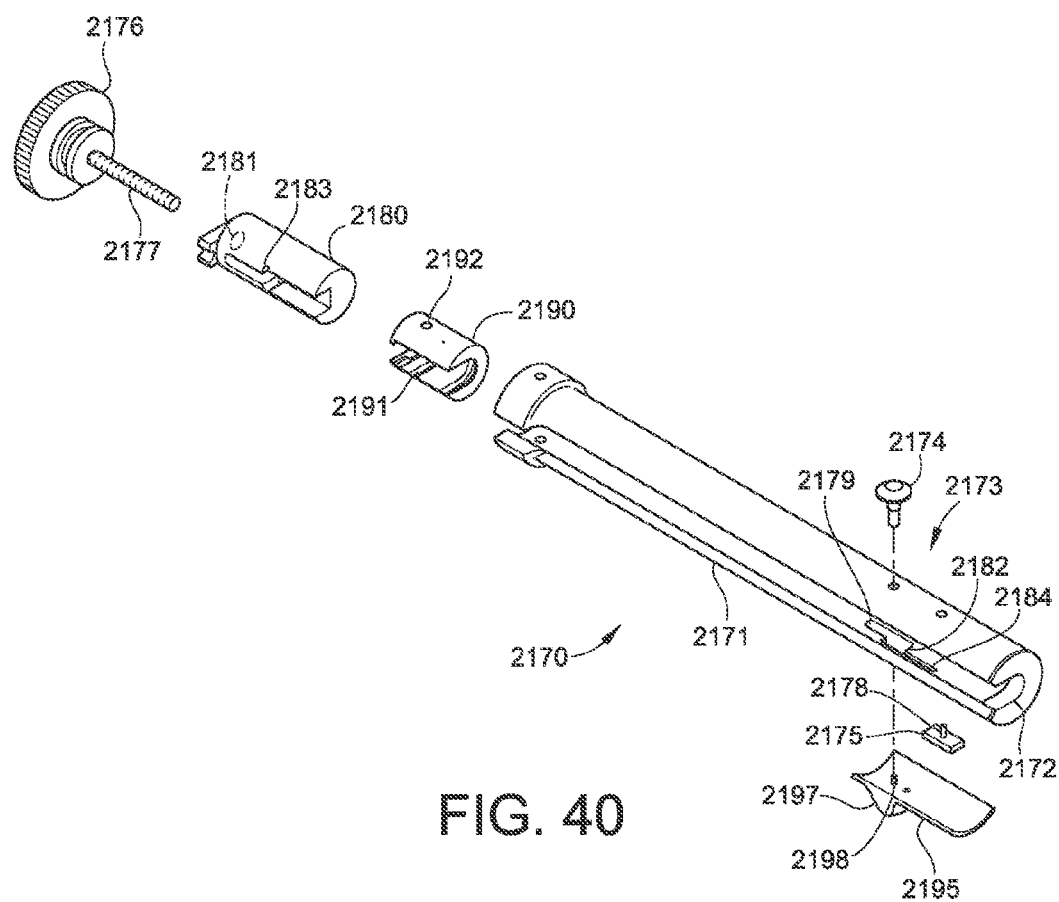
FIG. 40 depicts another embodiment of a control device or handle.

In FIG. 40, another control device 2170 includes a hollow cylindrical body 2171, with a central channel 2172. There is a series of bores 2173 for use with a set pin 2174 to set the position of a front slider 2190 with a hollowed-out portion 2191 for retaining an outer sheath or outer portion of the deployment device. The outer sheath is anchored within slider 2190 and its motion is controlled by a hand actuator 2195 with a thumb grip 2197 for use in moving the slider backward or forwards. The slider 2190 is connected to the hand actuator 2195 via an adapter 2175 and pin 2178. Thus, the slider, and the position of the outer sheath may be retained in place using a bore 2192 in the slider and retaining pin 2174, along with the hand actuator 2195.

Adapter 2175 and pin 2178 connect slider 2190, and an attached outer sheath, to the hand actuator 2195. Pin 2198, also known as a member, on the bottom surface of hand actuator 2195, restrains the movement of the hand actuator to the paths molded into the outer surface of the control device body 2171. These paths include forward track 2184, intermediate track 2182, and rear track 2179. The lengths of the forward and rear tracks are thus fixed or predetermined distances. The forward and rear tracks 2184, 1289 are generally parallel and are separated by intermediate, transverse track 2182.

The control wire of the catheter is connected to a rear retainer 2180 with one or more hollowed-out portions 2183 for securing the control wire or inner portion of the deployment device. The rear retainer 2180 is easily held in place securely and movably by a molded-in retaining nut 2181 and a threaded rod 2177. The handwheel 2176 itself fits snugly into the proximal, enlarged portion of the cylindrical body 2171. The handwheel may be pinned in position and may rotate in place to allow translation of the rear retainer 2180 and thus the inner control wire. The handwheel 2176 and the threaded rod 2177 allow fine adjustments to the position of the control wire with respect to the position of the outer sheath.

In use, the physician or other medical professional will advance the catheter using the non-invasive imaging techniques already described. The prosthesis is advanced to the point where the catheter tip is in the left atrium, while all portions of the prosthesis remain within the outer sheath. The slider 2190 is fixed in a distal position using pin 2174, the forward or most distal orifice of the series of orifices 2173, and orifice 2192 of the slider 2190. At this point, the hand actuator is at its most distal position, and pin 2198 is all the way forward, to the right in right track 2184, i.e., the most distal position.

At this point, the left flange is positioned within the patient's left atrium, still remaining with the outer sheath, and the retainer 2180 is locked in position and not moved further. The outer sheath is then retracted using the slider 2190 and hand actuator 2195, similar to step 6000 in FIG. 27. In one embodiment, the outer sheath is retracted by sliding the hand actuator 2195 straight to the rear and proximally, or to the left in FIG. 40. This movement is allowed by the rearward movement of member or pin 2198 in right track 2184. This movement is a fixed distance, until the pin strikes the rear of the long portion 2184 and the start of transverse portion 2182 of the molded-in paths and can go no further. The length of the long portion 2184 is fixed when the long portion is molded or machined into hollow cylindrical body 2171. The distance is that needed to deploy the left flange of the interatrial pressure vent or prosthesis. The distance may also be that needed to deploy the left flange and the central or valve portion. In one embodiment, this distance is about 7 mm. In other embodiments, the distance may be 5 mm, 6 mm, 8 mm, 9 mm or other desired distance.

After the desired portion has been deployed, the physician may use fluoroscopy or echosound to determine the exact position of the prosthesis with the patient before proceeding. If an adjustment is needed, the prosthesis can readily be retracted into the outer sheath for removal or redeployment at this stage, as will be seen in some of the improved designs for retrieval and redeployment described below.

If continuation is indicated, the surgeon or medical professional will then prepare to deploy the remainder of the interatrial pressure vent or prosthesis. The first step is to rotate the hand actuator 2195 a few degrees to the right so that pin 2198 is now in the other long track 2179. The transverse portion 2182 is only about twice as wide as pin 2198. Rotation of the hand actuator thus does not cause the prosthesis within the patient's heart to translate proximally or distally. The surgeon then moves the hand actuator in a proximal direction, to the left in FIG. 40, further retracting the outer sheath and deploying the right atrium flange into the right atrium of the patient's heart. The length of track 2179 is also a fixed distance, the distance fixed when the track is molded into the hollow cylindrical body 2171. In one embodiment, the distance is 8 mm, a little longer than the length of track 2184. In other embodiments, the distance may vary, as noted above. The distances, or the length of the tracks, may be tailored to fit the patient's anatomy, for example, by determining ahead of time the width of the patient's septum or the dimensions of the patient's heart.

In another embodiment, not shown, the two tracks of predetermined length may be a single length with a pin or other obstacle inserted at a desired point along the length of the track. The pin will prevent further movement of pin 2198 in a proximal direction and will stop the movement of the hand actuator 2195 after it has moved a fixed or predetermined distance, e.g., 7 mm. After the pin is removed, the surgeon or other medical professional may continue to move the hand actuator in a proximal direction along the remainder of the predetermined or fixed length of the track.

Retrieval of the Prosthesis

In some rare situations, the deployment may not be satisfactory for any of a number of reasons, and the prosthesis may be removed from the patient. This very unusual situation may become apparent before the procedure has been completed. In some cases, the need for removal may become apparent while the guidewire with which the procedure was begun is still in place, such, for example, the embodiments described in connection with FIG. 19A. In other cases, it may be necessary to introduce a guidewire to begin a removal procedure, while in other cases a guidewire is not used. If the prosthesis has not been fully deployed, removal is typically accomplished by retracting the control wire attached to the prosthesis, or by advancing the outer sheath over the prosthesis. Removal is then accomplished by merely withdrawing the outer sheath and all its components. Once the prosthesis has been deployed, different techniques may be needed, as depicted herein.

Figure 41:
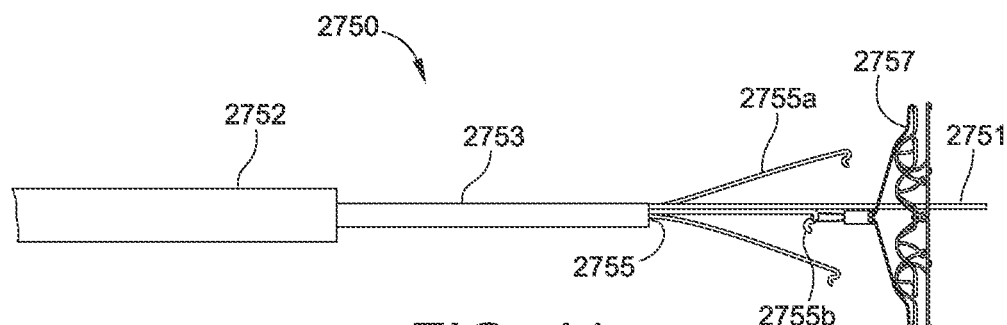
FIG. 41 depicts a retrieval device useful for retrieving a deployed prosthesis.
Figure 42:
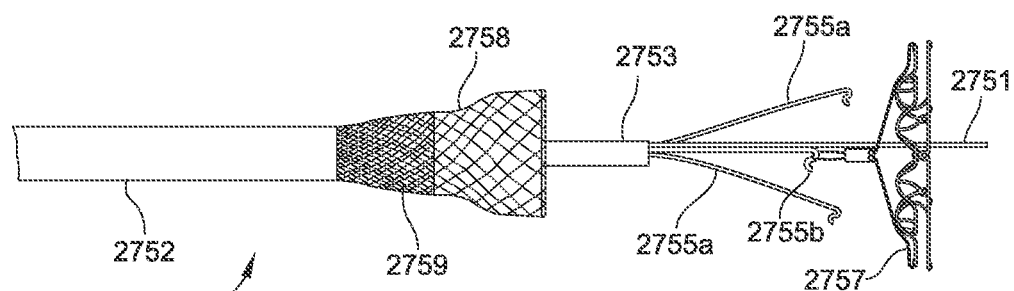
FIG. 42 depicts the retrieval device of FIG. 41 with a retrieval basket deployed.
Figure 43:
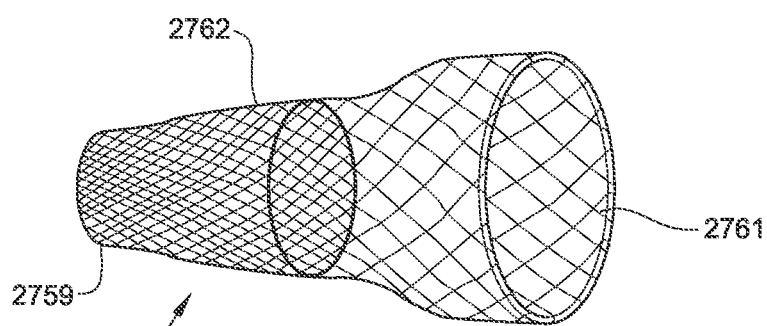
FIG. 43 depicts a closer view of the basket of FIG. 42.

Retrieval of the fully deployed prosthesis is depicted in FIGS. 41 and 42, while the tools used for retrieval are depicted in FIGS. 41, 42 and 43. The retrieval device 2750 is advanced to the desired location within the patient along a guidewire 2751. Components of the retrieval device 2750 include an outer sheath 2752, an inner sheath 2753 and a grasper 2755, such as the three-prong grasper depicted in FIG. 41. In one embodiment, the outer sheath has an outer diameter of about 21 Fr (about 7 mm) while the inner diameter is about 6.7 mm. In the figure, the grasper 2755 has caught the prosthesis 2757 with one of the three prongs 2755a and its protruding hook or tab 2755b. As noted, the tab 2755b may be useful for insertion into an orifice of a prosthesis leg or strut, as seen in FIG. 2A, for retrieval of the prosthesis. In FIG. 2A, legs 103x of the flanges meet at a juncture, an apex or an end of two of the legs. Each flange of the prosthesis includes two or more legs, usually in pairs, each pair also forming an apex where the legs meet.

It will be recognized that one or more components of the retrieval device may include radiopaque components or markers for better visibility by non-invasive techniques, such as fluoroscopy, echo-sound, and so forth. In one embodiment, one or more of the prongs of the grasper may be made of a radiopaque metal or material, such as the metals themselves or alloys of gold, platinum, palladium, tungsten and tantalum. In another embodiment, the prongs of may include one or more markers, e.g., a small dot or implant of a radiopaque material or echogenic material that will be easily detected by x-ray, fluoroscopy, echosound or other suitable non-invasive imaging technique.

In use, the retrieval device is advanced to the desired location within the patient, using non-invasive techniques and radiomarkers, echogenic markers, or other indicators on the device. The user has three controls to manipulate the device, in addition to advancing and retracting the entire device 2750, e.g., while the internal portions are contained within the outer sheath 2752. The inner sheath 2753 has a control wire (not shown) as does the grasper 2755 (control wire not shown). The retrieval basket 2758, depicted in FIGS. 42 and 43, also is advanced and retracted using its control wire (not shown), as will be understood by those with skill in minimally-invasive surgery arts. The grasper 2755, as the innermost component and nearest the guide wire, may have a micro-rail, i.e., a lumen or longitudinal cavity, to follow precisely the path of the guide wire. In other embodiments, it is possible to assemble the retriever so that an inner sheath is not used. For example, if the basket is assembled proximally from the grasper, and the grasper sufficiently distal from the basket, an inner sheath and its control wire may not be needed.

The user advances the device 2750 and outer sheath 2752 near the desired point and verifies the location. The user may then advance the inner sheath 2753 out from the outer sheath 2752. The user may then advance the grasper 2755 from the inner sheath and maneuver the grasper and the inner sheath, or the grasper or the sheath separately as desired, to grasp the prosthesis 2757 with the prongs of the grasper. There is no separate closing control for the grasper. The user simply maneuvers the grasper in such a manner that when the grasper is retracted, the prongs approach each other in a manner to grasp and retrieve the prosthesis. The control wire or control handle for the grasper in one embodiment has a locking feature that allows the surgeon to close the grasper and not be concerned about further manipulation of the grasper, except for withdrawal. In one embodiment, the grasper is a three-pronged Hobbs forceps, available from Hobbs Medical, Stamford Springs, Conn., USA. In another embodiment, the grasper or the retrieval device may also have a fluid channel for irrigating the retrieval site, much as the deployment catheter has a fluid channel.

Other graspers or retrievers may be used instead, such as those with four prongs, or even other retrieval devices, such as a single prong or tab. The single tab or prong may be in the form of a short cylinder, suitable for insertion in an orifice of the struts or legs of a flanged atrial septum implantable device, as shown in FIGS. 2A and 7B. The user maneuvers the grasper or tool so that the implantable device is hooked by one or more of the orifices, and then uses this connection to retrieve the implantable device.

In other embodiments, the implanted device may have one or more legs of the right atrium flange longer than most legs of the flange, making it easier to grasp one or more of the legs or struts, as shown above in FIGS. 7B and 7C. In these embodiments, the grasper may more easily approach the implanted device and grasp it, whether a multi-prong grasper is used, or whether a single tab or prong is used to grasp the longer leg. In other embodiments, the implanted device may have a flange more suited for retrieval, such as the conical flanges depicted in FIGS. 22 and 23. In these embodiments, it is relatively easy for a user to grasp the conical apex 450 for retrieving the implant via a grasper, as discussed above. Retrieval is more user-friendly also, since the shape of the implant lends itself to being pulled in the proximal direction, i.e., towards the outside of the body of the patient.

The inner sheath and the grasper are then retracted, as shown in FIG. 42, and the basket 2758 is deployed by advancing its control wire (not shown). Basket 2758 may be made from metal mesh, such as Nitinol or other medically-acceptable, shape-memory material. Nitinol is a good choice because it can be trained to assume the desired basket form as it deploys from the outer sheath. There may also be a barrier layer 2759 to help prevent any undesired piercings by wires or components of the prosthesis. The barrier layer may be made of a suitable medically-acceptable cloth, such as polyester (Dacron®, for example), or other material. Once the prosthesis is grasped and the basket deployed, the grasper 2755 and the prosthesis may be retracted into the basket by advancing the basket or retracting the grasper and prosthesis, or both. The basket, grasper and prosthesis are all withdrawn into the outer sheath, which may then be safely removed from the patient with the retrieved prosthesis.

As noted, basket 2858 may be made from metal mesh, such as a mesh made from Nitinol or other wires. In one embodiment, Nitinol wires may be 0.003 inches in diameter (about 0.08 mm in diameter); in another embodiment, the wires may be 0.020 inches in diameter (about 0.51 mm in diameter). Other embodiments may use flat wires or ovate-shaped wires. Basket 2759 is made from a single layer of Nitinol mesh. Other embodiments, such as the one depicted in FIG. 43, may use a basket 2760 having two layers, i.e., a basket including an inner layer 2761 folded over to form a second, outer layer 2762. The two-layer basket may be better at preventing objects within the basket from protruding outside the basket.

Retrieval Devices with Dilators

It is clear that the outer sheath of a retrieval device, and all components, should be as small and as thin as possible for patient comfort. Accordingly, in one embodiment, the outer sheath has an outer diameter of about 18-20 Fr. In one embodiment, the deployed basket has a largest outer diameter of about 20 mm, which is quite large compared to a 20 Fr outer catheter outer diameter. In other embodiments, the sizes may be larger or smaller, as needed. It is clear from inspection of the basket in FIGS. 42 and 43 that the space used to accommodate devices for retrieving the prosthesis will be somewhat greater than the space typically used to deploy the prosthesis.

Figure 44:
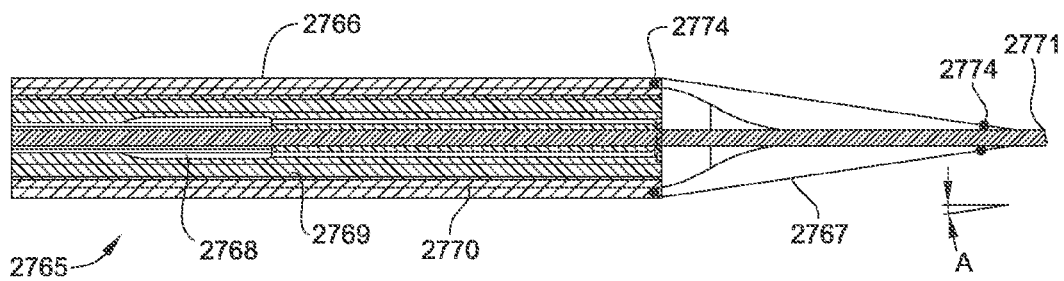
FIGS. 44 and 45 depict retrieval devices using dilators.
Figure 45:
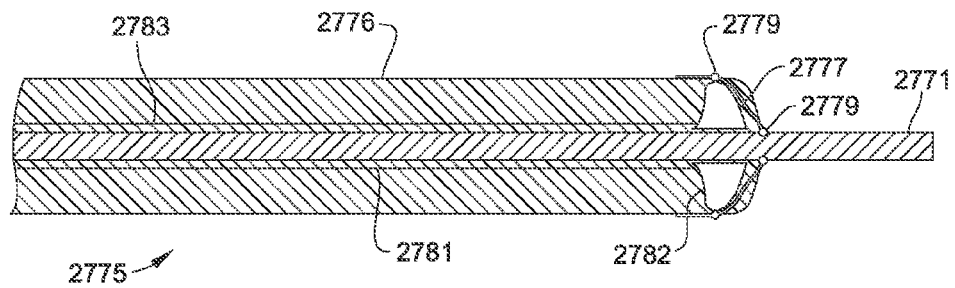

In order to ease the transition, a retrieval device may use a dilator on its distal end. While the tip is nominally termed a dilator, it does not expand, rather its purpose is to maintain the dimension of its widest portion while the forceps or other device within the sheath is deployed behind the tip. Two embodiments are depicted in FIGS. 44 and 45. In FIG. 44, retrieval device 2765 includes an outer sheath 2766 and device tip 2767. The device is introduced into the patient via a guidewire 2771. Retrieval device 2765 includes a grasper or forceps 2768, a jacket or outer covering 2769, as discussed above, and a braided capture sleeve 2770, such as a capture sleeve made from Nitinol mesh. Retrieval device 2765 also includes X-ray or echogenic markers 2774 in useful locations, such as at the distal end of the outer sheath 2766 or the dilator 2767.

In use, the device tip is deployed when the user pushes the forceps 2768 distally, or withdraws the outer sheath 2766 in a proximal direction. The device tip is constrained to move axially along the guidewire 2771, and its location will thus remain in the control of the medical professional deploying or retrieving the prosthesis.

The embodiment of FIG. 44 features a device tip with a rather long transition section. When the user has advanced the retrieval device to the desired location within the patient, the sheath is withdrawn in a proximal direction, or the forceps is advanced in a distal direction to deploy the forceps and the basket. Because the device tip has a very gradual transition, the movement and the disruption to the patient are minimal. In this embodiment, the angle A of the device tip may range from about 10 degrees to about 30 degrees. Other angles may be used. The length of the transition section may vary from about 15 mm to about 25 mm. Other lengths may be used.

Another embodiment is depicted in FIG. 45. In this embodiment, the retrieval device 2775 also has an outer sheath 2776 and a separable device tip 2777. As shown in this view, the angle of the device tip is much greater than the previous embodiment, while the length of the device tip is much shorter. Retrieval device 2775 includes an inner sheath 2781 and a balloon 2782 and an inflation/deflation lumen 2783. Retrieval device 2775 also includes X-ray or echogenic markers 2779 in useful locations, such as at the distal end of the outer sheath 2776 or the dilator 2777. The length of the transition section may vary from about 5 mm to about 120 mm. Other lengths may be used.

In this embodiment, the retrieval device is used with the device tip and the internal balloon that is inflated to create a space for the retrieval device. In this embodiment, the retrieval device 2775 does not include a retrieval forceps at the outset. After the device tip is deployed and the balloon is expanded to create a space, the balloon is deflated and retracted and a retrieval forceps and basket are exchanged along the guidewire for the balloon and the inflation equipment. The balloon may be expanded by inflating the balloon to a pressure from 6 atm to 20 atm.

Designs for Retrievability and Redeployability

FIGS. 46-49 depict additional embodiments of interatrial implantable prostheses which have been designed for easier retrieval and also for redeployment once they have been retrieved. A first improved embodiment 100a is depicted in FIGS. 46A-46B. The drawings depict several views of body element 100a, showing how the ends of flange segments 102a-102h, 103a-103h are rounded at their distal ends 115 and 116 to reduce stress concentrations against the interatrial septum after placement. These distal ends, or apices where the strut legs intersect, include bores 109a, 109b, 110a, 100b into which radiopaque or echogenic markers 118a, 118b and 119a, 119b can be positioned. Using these markers, the device may more easily be visualized using radiographic imaging equipment such as with x-ray, fluoroscopy, magnetic resonance, ultrasound or other imaging techniques. Markers as disclosed herein may be applied to the ends of any segments, not just those with holes or eyelets therein. Radiopaque or echogenic markers 118a, 118b, 119a, 119b can be swaged, riveted, adhered, or otherwise placed and secured into the bores and dimensioned to be flush with the contours of the segments. As noted previously, suture rings 117a, 117b may be used to secure the left atrium flange segments 103a-h to the right atrium flange segments 102a-h.

The retrieval legs described herein may be made from nitinol wire, stainless steel wire (such as grades 304, 304L, 316 and 316L, among others), nylon sutures (e.g., polyamide), polypropylene sutures (e.g., Prolene®), or any other material that is medically acceptable and resistant to stretching. Materials that assume a known shape are desirable, as are materials that are visible under echographic or x-ray imaging conditions. The legs may thus take on a filamentary, thread, suture or wire shape, and may comprise a single thread or wire, or more than one suture, filament or wire. Wires made from nitinol or other metals may have a thickness from about 0.004 to 0.025 inches (about 0.11 to 0.64 mm). Sutures may range from about 8-0 to 7 (U.S.P. designations), i.e., from about 18 to 40 AWG, or even a little thinner than 40 gauge. The diameters of such sutures will range from about 0.04 mm to about 0.8 mm, and may apply to collagenous materials, synthetic absorbable materials, and synthetic non-absorbable materials.

Figure 46A:
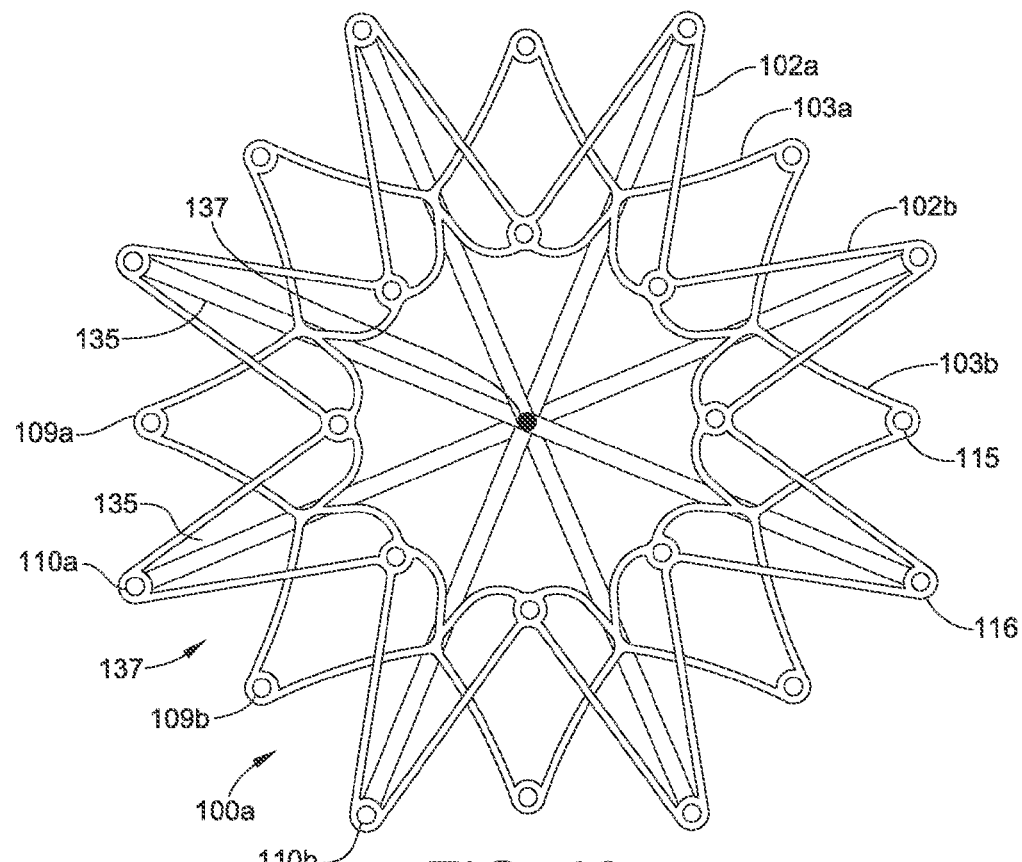
FIGS. 46-49 depict additional embodiments of an implantable prosthesis with retrieval and redeployment features.

FIG. 46A depicts several retrieval legs 135 joined to a central nub 137. The retrieval legs may be made of nitinol wires or of sutures and may extend from the bores 109 of right atrium flange legs 102a-h to a central juncture or nub 137. Portions of the sutures or wires may be made from radiopaque materials or MR-visible materials so that the nub 137 is visible using non-invasive imaging techniques. At a juncture, the retrieval legs may be joined into a short tube 175 and crimped into tube 175. A single suture or wire loop 177, or more than one loop, may then extend above the crimp for joining to the inner catheter control wire, or for grasping by a retrieval device. A typical crimp tube is visible under x-ray or echographic (sound) imaging. Thus, the tube may be stainless steel or radiopaque plastic. One embodiment of the tube has a 0.035 inch i.d. (0.90 mm), 0.008 in (about 0.2 mm) wall thickness, and about a 0.050 inch (1.3 mm) o.d. Other embodiments may be used.

Figure 46B:
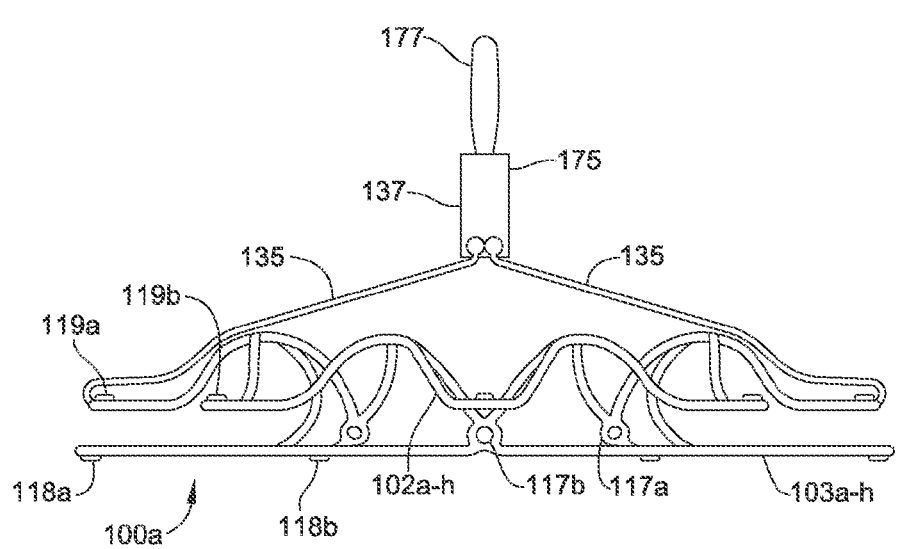

Retrieval loop 177 may be radiopaque or echograpically visible, or may include one or more threads that are radiopaque or echo-visible, such as a gold or platinum thread. The retrieval legs of this design do not interfere with the function of the prosthesis but do extend a short distance proximally, as shown in FIG. 46B. Thus, a filter, such as a thrombus filter, may be used as part of the prosthesis. In addition, the septa described above may be used in the central portion of the prosthesis. These include the bivalve of FIG. 26, or a tri-lobal valve, or other embodiments, such as those discussed above with respect to FIGS. 29A-29C.

The prosthesis of FIGS. 46A-46B was deployed from a catheter, as described above, and is retrieved in a similar manner, described below. The retrieval device secures suture or wire 177 from the central tube or crimp 175 with an appropriate end-effector, hook or grasper on its inner control wire. The inner wire of the retrieval device is then withdrawn proximally, drawing the sutures or wires into a catheter, collapsing the right atrium flange, and then drawing the remainder of the prosthesis into the catheter. The device may then be withdrawn from the patient, or may also be redeployed, perhaps in a better position.

Figure 47A:
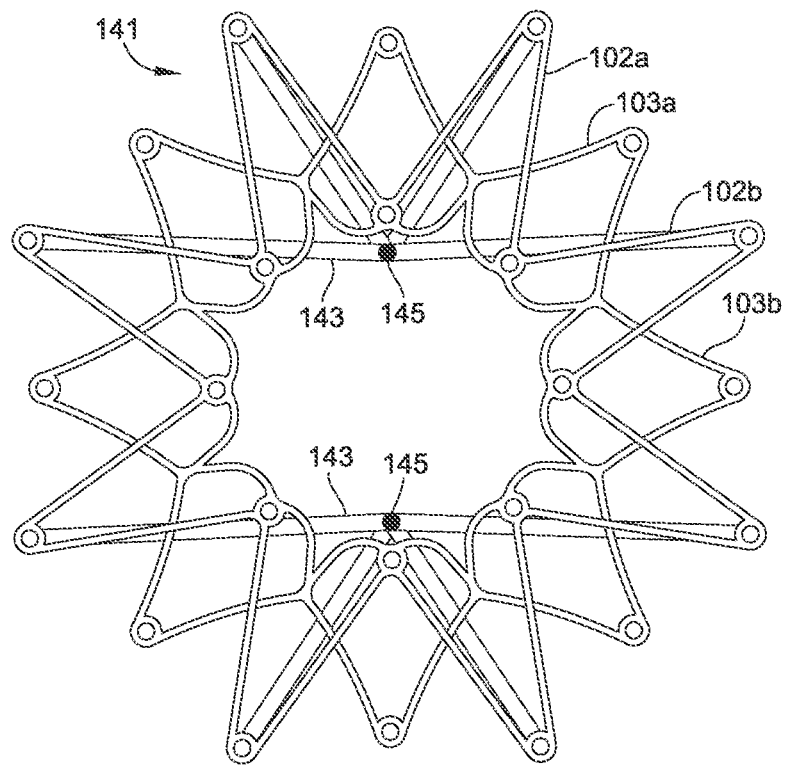
Figure 47B:
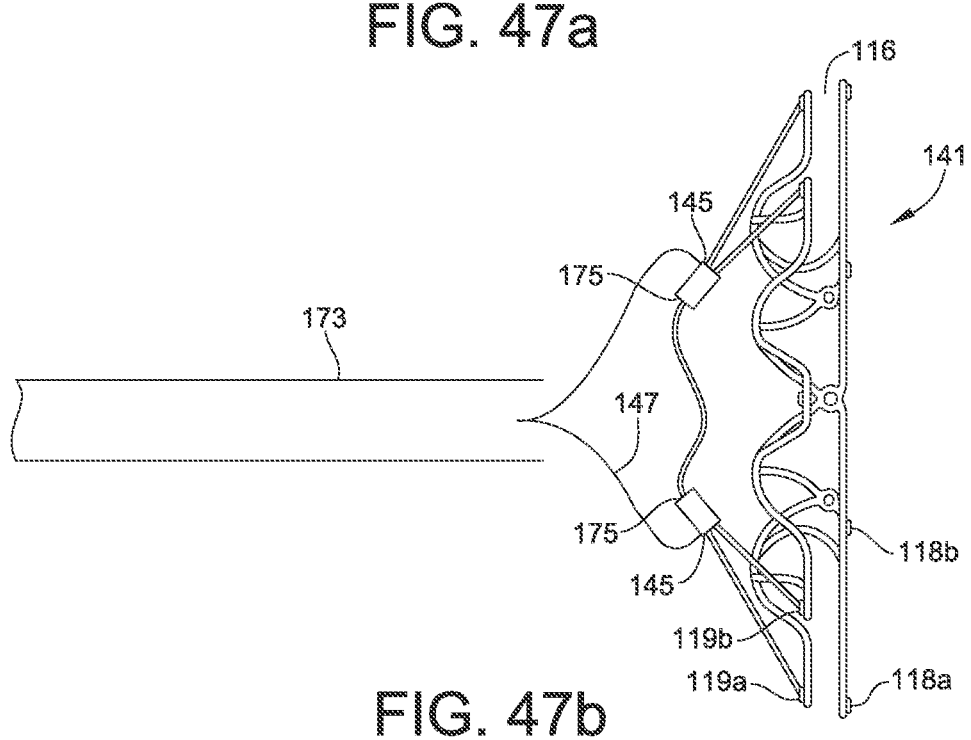

A second design specifically for retrievability is depicted in FIGS. 47A-47B. Prosthesis 141 is similar to prosthesis 100a of FIGS. 46A-46B. FIG. 47A is a top view, depicting prosthesis 141 with retrieval wires or sutures 143 connected to the apices 102a-h of the right atrium flange. In this embodiment, there are two central nubs or points 145, each for about 180 degrees of the flange. The retrieval wires 143 are tied together to form a nub 145 on each side of the right atrium flange. As seen in FIG. 47B, the nubs 145 are then joined with a crimp tube 175, with a loop 147 of one or more retrieval wires or sutures joining the two crimp tubes 175 and sides of the prosthesis for removal. The retrieval wires or sutures, and the nubs, may be made from the materials described above. As depicted in FIG. 47B, the wires or sutures avoid the central area of the prosthesis when deployed from catheter 173 and thus do not interfere with the functioning or deployment of the valve. The wires or sutures are available to assist in withdrawal and removal or redeployment of the prosthesis if needed. Retrieval loop 147 may be radiopaque or echographically visible, or may include one or more threads that are radiopaque or echo-visible, such as a gold or platinum thread.

Figure 48A:
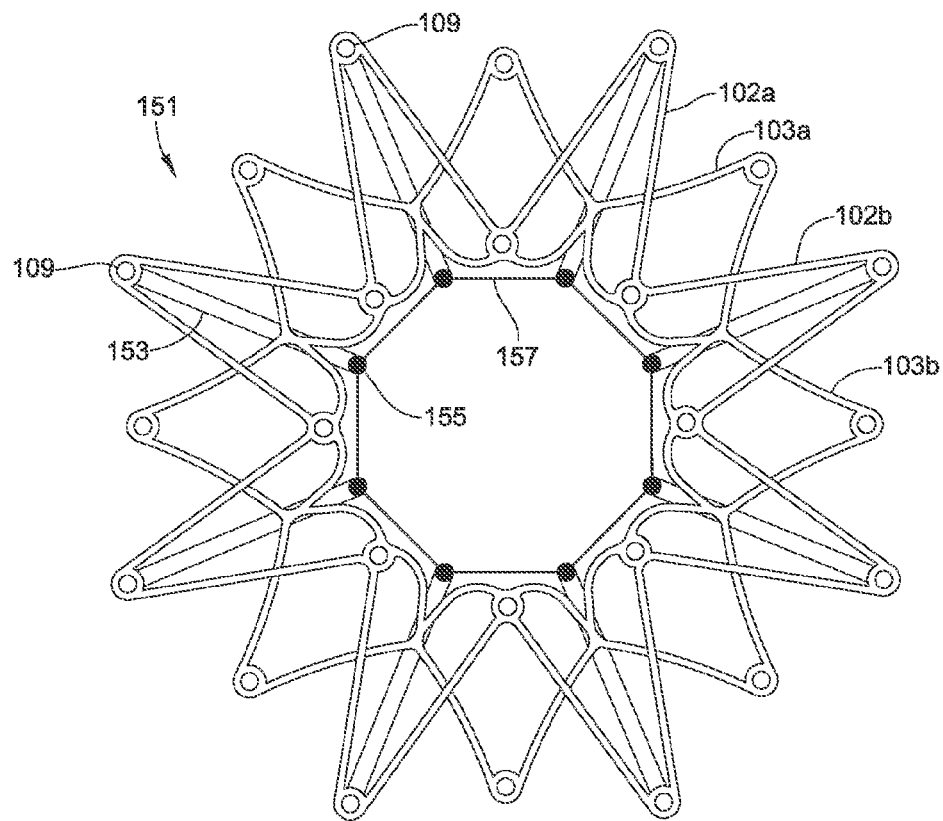
Figure 48B:
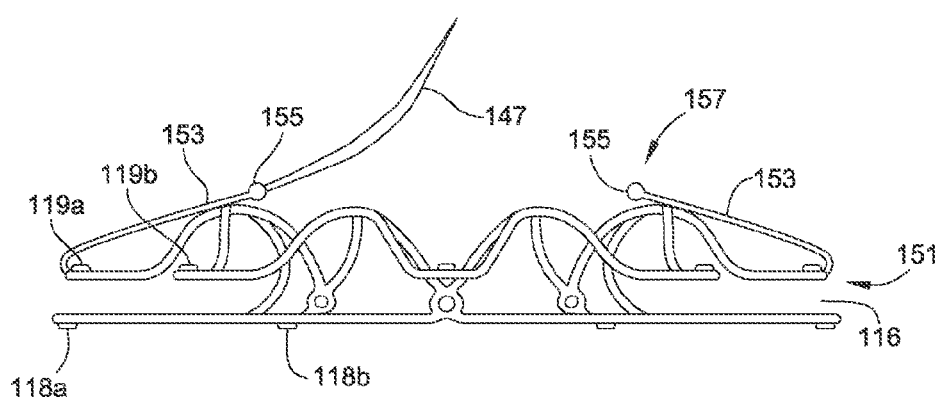

A third embodiment of a design for retrieval is depicted in FIGS. 48A and 48B. In this embodiment, prosthesis 151 is very similar to prosthesis 141 above, including retrieval sutures or wires 153 from bores 109 of the right atrium flange apices 102a-h, to a central annular retrieval suture or wire 157. Each retrieval suture or wire 153 is joined to the central retrieval thread 157 at a juncture 155. The junctures may simply be suture tie-offs; alternatively, the junctures could be orifices in central wire 157 for joining retrieval sutures or wires 153. In some embodiments, an additional retrieval suture or wire 147, suitable for non-invasive imaging, may be tied to the central thread at least at one point for grasping by a retrieval device.

Figure 49:
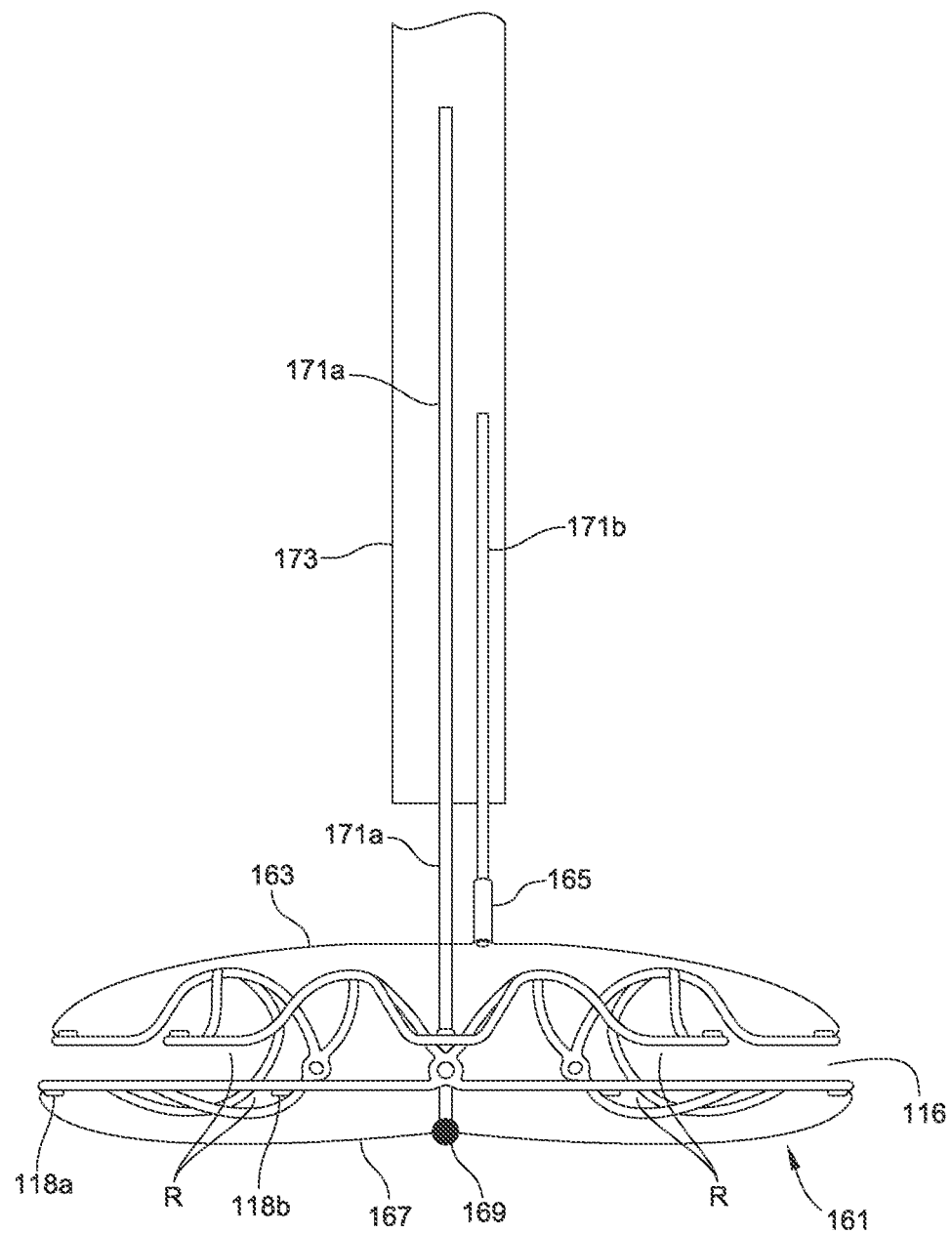

A fourth embodiment of a prosthesis 161 designed for retrieval and redeployment is depicted in FIG. 49. Prosthesis 161 is similar to prosthesis 100a, described above. In the fourth embodiment, there is a retrieval wire or suture 163 secured to each apex 102a-h of the right atrium flange and there is a retrieval wire or suture 167 secured to each apex 103a-h of the left atrium flange. The right atrium flange retrieval wires or sutures are joined to a central point or nub 165 and secured to an inner control wire 171b of a catheter 173. Central nub 165 may be a crimp tube and retrieval suture or wire, as described above. The left atrium flange retrieval wires or sutures are also joined to a central nub 169 and secured to an inner control wire 171a. Central nub 169 may be a crimp tube and retrieval suture or wire, as described above. To deploy the prosthesis 161, the medical professional positions the prosthesis in the correct position within the patient and then releases the left atrium flange, disengaging the inner control wire from nub 169, and also releases the right atrium flange, disengaging the inner control wire from nub 165.

If retrieval is desired, the grasper or retrieval device grasps or engages both nubs 165, 169, preferably separately, with inner control wires 171a, 171b, or with graspers attached to them, to collapse the respective flange and withdraw the prosthesis, as described below. In one embodiment, left atrium flange legs 103a-h have a greater radius R at their root and may even approach the septum wall at an obtuse angle, i.e., as shown in FIG. 49. This larger radius will make it easier to collapse the legs and struts of the flange. Once the prosthesis is withdrawn, it may be redeployed to a better position within the patient. Prosthesis 161 is capable of having both its left and right atrium flanges collapsed. If separate control wires are used, one for each flange, the flanges may be collapsed separately in time, thus requiring less force to withdraw.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the invention unless otherwise claimed. No language in the specification should be construed as indicating any non-claimed element as essential to the practice of the invention.

While embodiments have been disclosed and described in detail, it is understood that various modifications and improvements thereon will become readily apparent to those skilled in the art. Accordingly, the spirit and scope of the present disclosure is not limited by the foregoing examples, but is better understood by the claims below.

What is claimed is:

1. A device for implantation into an atrial septum of a patient, the device comprising:
   a cylindrical core defining a passage through the atrial septum;
   a flow control element comprising a valve within the passage;
   a first flange connected to the cylindrical core and adapted to engage a first surface of the atrial septum, wherein said first flange comprises a plurality of struts and apices, wherein each apex further comprises a bore;
   a plurality of retrieval legs extending from each apex and joined together; and
   a second flange connected to the cylindrical core and adapted to engage a second surface of the atrial septum.

2. The device according to claim 1, wherein each retrieval leg comprises at least one metallic wire or filamentary suture.

3. The device according to claim 1, wherein the plurality of retrieval legs are joined at a nub or a crimp tube.

4. The device according to claim 1, wherein the plurality of retrieval legs comprises a first plurality and a second plurality, each of the first and second pluralities joined at a separate nub or tube.

5. The device according to claim 4, further comprising a retrieval filament joining the separate nubs or tubes.

6. The device according to claim 1, wherein the plurality of retrieval legs are joined together with an annular retrieval filament.

7. The device according to claim 1, wherein the second flange further comprises a plurality of struts and apices, wherein each apex of the second flange further comprises a bore, and further comprising a plurality of retrieval legs extending from each apex of the second flange and joined together.

8. The device according to claim 7, wherein the plurality of legs from the second flange apices are joined together for connection to a control wire of a deployment catheter.

9. The device according to claim 1, wherein the retrieval legs are selected from the group consisting of metal, nitinol, sutures and combinations thereof.

10. The device according to claim 1, further comprising a radiopaque or echogenic marker.

11. A device for implantation into an atrial septum of a patient, the device comprising:
    a cylindrical core defining a passage through the atrial septum;
    a flow control element comprising a valve within the passage;
    a first flange connected to the cylindrical core and adapted to engage a first surface of the atrial septum, wherein said first flange comprises a plurality of struts joined at apices, each apex comprising a bore;
    a plurality of retrieval legs extending from each apex and joined together;
    a second flange connected to the cylindrical core and adapted to engage a second surface of the atrial septum; and
    a radiopaque or echogenic marker attached to a bore of at least the first or second flange.

12. The device according to claim 11, further comprising a thrombus filter attached to the first flange.

13. The device according to claim 11, wherein the plurality of retrieval legs comprises a first plurality and a second plurality, each of the first and second pluralities joined at a separate tube or nub, the tubes or nubs joined with a retrieval filament.

14. The device according to claim 11, wherein at least one of the apices comprises a bore for attachment to a control wire of a delivery catheter.

15. The device according to claim 11, wherein the plurality of retrieval legs are joined together with an annular retrieval suture or wire.

16. A device for implantation into an atrial septum of a patient, the device comprising:
    a cylindrical core defining a passage through the atrial septum;
    a flow control element comprising a valve within the passage;
    a first flange connected to the cylindrical core and adapted to engage a first surface of the atrial septum, wherein said first flange comprises a plurality of struts and apices, each apex comprising a bore, and further comprising a plurality of retrieval legs extending from each apex and joined together; and
    a second flange connected to the cylindrical core and adapted to engage a second surface of the atrial septum, wherein said second flange comprises a plurality of struts and apices, and further comprising a plurality of retrieval legs extending from each apex and joined together.

17. The device according to claim 16, wherein the retrieval legs from the first flange are joined together at a first nub and the retrieval legs from the second flange are joined together at a second nub, and wherein the first and second nubs each comprises an echogenic or radiopaque material.

18. The device according to claim 16, wherein at least the first nub is connected to a control wire of a deployment catheter.

19. The device according to claim 16, further comprising a deployment catheter connected to the device.

20. The device according to claim 16, further comprising a deployment catheter connected to the device and a control handle connected to the deployment catheter.

* * * * *